United States Patent
Reddy

(10) Patent No.: US 11,542,296 B2
(45) Date of Patent: Jan. 3, 2023

(54) NEUROSTEROID COMPOUNDS AND METHODS FOR THEIR PREPARATION AND USE IN TREATING CENTRAL NERVOUS SYSTEM DISORDERS

(71) Applicant: THE TEXAS A&M UNIVERSITY SYSTEM, College Station, TX (US)

(72) Inventor: Doodipala Samba Reddy, Bryan, TX (US)

(73) Assignee: THE TEXAS A&M UNIVERSITY SYSTEM, College Station, TX (US)

( * ) Notice: Subject to any disclaimer, the term of this patent is extended or adjusted under 35 U.S.C. 154(b) by 0 days.

(21) Appl. No.: 17/049,976

(22) PCT Filed: Apr. 23, 2019

(86) PCT No.: PCT/US2019/028755
§ 371 (c)(1),
(2) Date: Oct. 23, 2020

(87) PCT Pub. No.: WO2019/209850
PCT Pub. Date: Oct. 31, 2019

(65) Prior Publication Data
US 2021/0238220 A1 Aug. 5, 2021

Related U.S. Application Data

(60) Provisional application No. 62/661,187, filed on Apr. 23, 2018.

(51) Int. Cl.
C07J 43/00 (2006.01)
A61P 25/08 (2006.01)
C07J 5/00 (2006.01)
C07J 41/00 (2006.01)

(52) U.S. Cl.
CPC ............. *C07J 43/003* (2013.01); *A61P 25/08* (2018.01); *C07J 5/0015* (2013.01); *C07J 41/0088* (2013.01)

(58) Field of Classification Search
CPC .... C07J 5/0015; C07J 41/0088; C07J 43/003; A61P 25/08
See application file for complete search history.

(56) References Cited

FOREIGN PATENT DOCUMENTS

| WO | WO 93/03732 | 3/1993 |
| WO | WO 94/27608 | 12/1994 |
| WO | WO 96/16076 | 5/1996 |

OTHER PUBLICATIONS

Chuang, S.-H, et al. "3β-Methyl-Neurosteroid Analogs Are Preferential Positive Allosteric Modulators and Direct Activators of Extrasynaptic δ-Subunit γ-Aminobutyric Acid Type A Receptors in the Hippocampus Dentate Gyrus Subfield" *J Pharmacol Exp Ther*, Jun. 2018, pp. 583-601, vol. 365, No. 3.

Hogenkamp, D. J. et al. "Pharmacological profile of a 17β-heteroaryl-substituted neuroactive steroid" *Psychopharmacology*, 2014, pp. 3517-3524, vol. 231, No. 17.

Written Opinion in International Application No. PCT/US2019/028755, Oct. 1, 2019, pp. 1-7.

*Primary Examiner* — Barbara P Badio
(74) *Attorney, Agent, or Firm* — Saliwanchik, Lloyd & Eisenschenk

(57) ABSTRACT

Described herein is the chemical structure of neurosteroid derivative compounds, methods of synthesizing the derivatives, and their uses in treating disorders, including those of the central nervous system. These compounds are readily synthesized and have improved pharmaceutical properties, including water solubility, compared to known neurosteroids.

16 Claims, 41 Drawing Sheets

21-OH GX Phosphate Disodium

21-OH GX Valine

21-OH GX Lysine

21-OH GX Succinate Sodium

21-OH GX Piperidine Diol

UCI-50027 Phosphate Disodium

UCI-50027 Diisopropyl Carbonate

UCI-50027 Valine Citric Salt

UCI-50027 Lysine bis-citric acid salt

UCI-50027 MethylPhosphite Disodium

21-OH GX Methylphosphite Disodium

21-OH GX Carbamate (A)

(A)

NEUROSTEROID COMPOUNDS AND METHODS FOR THEIR PREPARATION AND USE IN TREATING CENTRAL NERVOUS SYSTEM DISORDERS

CROSS-REFERENCE TO RELATED APPLICATIONS

This application is the U.S. National Stage Application of International Patent Application No. PCT/US2019/028755, filed on Apr. 23, 2019 which claims priority to U.S. Provisional Patent Application No. 62/661,187 filed on Apr. 23, 2018 which is specifically incorporated by reference in its entirety herein.

GOVERNMENT FUNDING

This invention was made with government support under grant U01-NS083460 awarded by the National Institutes of Health. The government has certain rights in the invention.

FIELD

The disclosure relates generally to neurosteroid compounds. The disclosure relates specifically to individual neurosteroid compounds and their use in treating central nervous system disorders. The disclosure further relates to derivative neurosteroid compounds of ganaxolone (GX) and its 17-isooxazole analog (UCI-50027), and CNS selective GABA-A receptor modulators, to the preparation thereof and to the therapeutic use thereof.

BACKGROUND

Diseases of the central nervous system (CNS) are very complex in nature, invoking, for example, combinations of organs (e.g., the brain), nerve systems and pathways, ligand-receptor interactions, and molecular communication processes. Because of their complex mechanisms of action as well as the wide impact of these diseases on health and well-being, including seizures, epilepsy, cognition, consciousness, behavior and neurological effects, the study of the development of new therapeutic approaches to management of these diseases is of high interest.

Epilepsy is a chronic neurological disorder characterized by recurrent and unprovoked seizures. A seizure is an abnormal electrical discharge in the brain that causes an alteration in consciousness, sensations, and behaviors. The symptoms that occur depend on the parts of the brain affected during the seizure. Common signs of seizures include staring, unusual feelings, twitching, unconsciousness, and jerking in the arms or legs.

According to recent estimates, around 65 million people are affected by epilepsy across the world [Jacobs M P, Leblanc, G G et al. Curing epilepsy: progress and future directions. Epilepsy Behav 2009; 14: 438-445; Hesdorffer D C and Begley C E. Surveillance of epilepsy and prevention of epilepsy and its sequelae: lessons from the Institute of Medicine report. Curr Opin Neurol 2013; 26: 168-173]. According to World Health Organization (WHO) estimates, nearly 80% of them are found in developing regions, including about 7 million in India. Epilepsy affects an estimated 3 million people in the United States and around 2 million patients in Europe in a variety of ways. About 150,000 new cases of epilepsy are diagnosed in the United States annually [Zack M M and Kobau R. National and State Estimates of the Numbers of Adults and Children with Active Epilepsy—United States, 2015. MMWR Morb Mortal Wkly Rep. 2017; 66:821-825]. Children and elderly are the fastest growing segments of the population with new cases of epilepsy. As a result of injuries from the recent armed conflicts and combat operations, Veterans and adult armed forces members are more prone to the condition. The Institute of Medicine (TOM) released a consensus report in 2012 on public health dimensions of the epilepsies focusing on promoting health and understanding epilepsy [Austin J K, Hesdorffer D C, Liverman C T, Schultz A M; Testimony Group. Testimonies submitted for the Institute of Medicine report: epilepsy across the spectrum: promoting health and understanding. Epilepsy Behav. 2012; 25:634-661]. The IOM report, Epilepsy Across the Spectrum: Promoting Health and Understanding, provided many recommendations which include one key recommendation on prevention of epilepsy. A recent study by the Epilepsy Foundation estimates that the annual financial cost of this disorder is $12.5 billion in the U.S. alone.

Epilepsy is a collective designation for a group of brain disorders consisting of a complex spectrum of different seizure types and syndromes. Epileptic seizures are classified into partial (simple and complex partial seizures) and generalized seizures (absence, tonic-clonic, myoclonic, and atonic seizures). Accurate diagnosis of seizure type and epileptic syndrome is critical for determining appropriate drug therapy and prognosis. The International League Against Epilepsy (ILAE) provided a definition of "seizure" and "epilepsy" [Falco-Walter J J, Scheffer I E, Fisher R S. The new definition and classification of seizures and epilepsy. Epilepsy Res. 2018; 139:73-79]. A seizure is defined as "a transient occurrence of signs and/or symptoms due to abnormal synchronous neuronal activity in the brain". Epilepsy is defined as "a disorder of the brain characterized by an enduring predisposition to generate epileptic seizures". A single seizure, therefore, does not constitute epilepsy. The diagnosis of epilepsy requires the occurrence of recurrent (two or more) epileptic seizures separated by at least 24 hours, unprovoked by any immediate identified cause [Scheffer I E et al. Classification of the epilepsies: New concepts for discussion and debate—Special report of the ILAE Classification Task Force of the Commission for Classification and Terminology. *Epilepsia Open* 2016; 1:37-44]. "Electrographic or EEG seizures" refer to any seizure that was recorded electrically, which was virtually all of the seizures. These electrographically recorded seizures could either be "nonconvulsive seizures" or "convulsive motor seizures."

Antiepileptic drugs (AEDs) are the mainstay for controlling seizures. Current drug therapy with several drugs (phenytoin, carbamazepine, levetiracetam, lamotrigine, topiramate, valproate, rufinamide, gabapentin, clonazepam, oxcarbazepine, and phenobarbital) is symptomatic in that available drugs inhibit seizures, but are neither effective prophylaxis nor cure is available. The goal of the therapy is to eliminate seizures without interfering with normal function [Gluaser T, Ben-Menachem E, Bourgeois B, et al. ILAE treatment guidelines: evidence-based analysis of antiepileptic drug efficacy and effectiveness as initial monotherapy for epileptic seizures and syndromes. *Epilepsia* 2006; 47: 1094-1120]. Despite many advances in epilepsy research, presently an estimated 30% of people with epilepsy have "intractable seizures" that do not respond to even the best available medication. Many epilepsy patients suffer from at least one anticonvulsant related side-effect (e.g., mood changes, sleepiness, or unsteadiness in gait). Furthermore, although seizures represent the most dramatic hallmark of epilepsy, many epilepsy patients develop comorbidity with neurological or psychiatric disease (memory impairment, depression).

Epilepsy is a chronic condition with many possible causes. Epilepsy may develop because of an abnormality in neural connectivity, an imbalance in inhibitory and excitatory neurotransmitters or some combination of these factors. Primary epilepsy (50%) is idiopathic ('unknown cause'). In secondary epilepsy (50%), seizures may result from a variety of conditions including brain injury, trauma, anoxia, metabolic imbalances, tumors, encephalitis, drug withdrawal, and neurotoxicity [Reddy D S. Role of hormones and neurosteroids in epileptogenesis. *Frontiers in Cellular Neuroscience* 2013; 7:115, 1-20]. It is estimated that the chance of having epilepsy during a lifetime of 80 years is about 3%. Epileptic seizures may also occur in recovering patients as a consequence of brain surgery. About 1% of all people develop recurrent unprovoked seizures without obvious reason or any other neurological abnormalities. These are named idiopathic epilepsies, generalized or partial, and they are assumed to be mainly of genetic origin. Some genes, coding for protein subunits of voltage-gated and ligand-gated ion channels including GABA receptors, have been associated with forms of generalized epilepsy and infantile seizure syndromes.

Epilepsy may develop as a consequence of brain injury. Traumatic brain injury (TBI), which affects more than 1.7 million individuals annually in the U.S., is a major cause of acquired epilepsy in adults [Faul M, Xu L, Wald M M, Coronado V G. Traumatic Brain Injury in the United States: Emergency Department Visits, Hospitalizations and Deaths 2002-2006. Centers for Disease Control and Prevention, National Center for Injury Prevention and Control, Atlanta, Ga., 2010; 1-72]. The annual burden of TBI has been estimated at over $60 billion [Piccenna L, Shears G, O'Brien T J. Management of post-traumatic epilepsy: an evidence review over the last 5 years and future directions. Epilepsia Open 2017; 2:123-144]. One prevalent form of such acquired epilepsies is temporal lobe epilepsy (TLE), the most common-type and drug-resistant form of epilepsy in adults [Pitkanen A, Kyyriainen J, Andrade P, Pasanen L, and Ndode-Ekane X E. Epilepsy after traumatic brain injury, in Models of Seizures and Epilepsy, 2nd ed. Academic Press, United Kingdom, 2017; 661-681; Engel J Jr. Epileptogenesis, traumatic brain injury, and biomarkers. Neurobiol Dis. 2019; 123:3-7]. The hallmark of TLE is sclerosis of the hippocampus, which in turn may lead to cognitive dysfunction due to the critical role of this structure plays in learning and memory. The other condition, stroke is a major risk factor for epilepsy in elderly. Post-stroke epilepsy (PSE) is typified by recurrent unprovoked seizures after stroke [Reddy D S, Bhimani A, Kuruba R, Park M J, and Sohrabji F. Prospects of modeling post-stroke epileptogenesis. J Neurosci Res 2016; 95:1000-1016]. According to the American Stroke Association, in 2010, worldwide prevalence of stroke was 33 million, with 16.9 million people having a first stroke.

The molecular mechanisms underlying the development of acquired epilepsy are not very well understood. The term 'epileptogenesis' is used to describe the complex plastic changes in the brain that, following a precipitating event, convert a normal brain into a brain debilitated by recurrent seizures [Clossen B L and Reddy D S. Novel therapeutic approaches for disease-modification of epileptogenesis for curing epilepsy. Biochim Biophys Acta 2017; 1863:1519-1538; Pitkänen A, Lukasiuk K. Molecular and cellular basis of epileptogenesis in symptomatic epilepsy. Epilepsy Behav. 2009; 14 Suppl 1:16-25]. Although specific types of epilepsy may have unique pathophysiological mechanisms, a broad hypothesis in this field is that convergent neuronal mechanisms are common in different forms of acquired epilepsy.

The current hypothesis about the pathogenesis of epilepsy (epileptogenesis) involves three stages: (i) the initial precipitating event; (ii) the latent period (no seizures); and (ii) the chronic period with spontaneous seizures [Reddy D S and Kuruba R. Experimental models of status epilepticus and neuronal injury for evaluation of therapeutic interventions. Int. J. Mol. Sci. 2013, 14, 18284-18318]. Acquired epilepsy typically develops due to an initial precipitating event such as traumatic brain injury (TBI), stroke, brain infections, or prolonged seizures. The other possible precipitating triggers for epileptogenesis include febrile seizures, metabolic dysfunction, alcohol withdrawal, and status epilepticus, an emergency condition characterized by continuous seizures or repeated seizures without regaining consciousness for 30 min or more. Biomarkers are utilized to study epileptogenesis and therapeutic interventions [Reddy S D, Younus I, Sridhar V, Reddy D S. Neuroimaging Biomarkers of Experimental Epileptogenesis and Refractory Epilepsy. Int J Mol Sci. 2019; 8; 20:1-23]. Exposure to chemical organophosphates and nerve agents can cause epilepsy as a result of cholinergic neurotoxicity and status epilepticus [de Araujo Furtado M, Rossetti F, Chanda S, Yourick D. Exposure to nerve agents: from status epilepticus to neuroinflammation, brain damage, neurogenesis and epilepsy. Neurotoxicology 2012; 33:1476-1490; Reddy D S and Colman E. A comparative analysis of human organophosphate poisonings using social media. Clin Translational Sci 2017; 10:225-230). The development of epileptogenesis is thought to be a step-function of time after the brain injury, with a latent period present between the brain injury and the first unprovoked seizure. Thus, the latent period offers a critical window for effective "antiepileptogenic" interventions for inhibiting the onset of epilepsy in people at risk.

A measure of epileptogenesis is the time when a brain insult induces molecular and cellular mechanisms that lead to spontaneous recurrent seizures (the latent period). The unpredictability of subsequent spontaneous recurrent seizure and presence of a latent period suggest that epileptogenesis occurs only during the time between the insult and the first clinical seizure. A "step function" of time after brain injury can be used to describe the development of epilepsy [Williams P A, White A M, Clark S, Ferraro D J, Swiercz W, Staley K J, Dudek F E. Development of spontaneous recurrent seizures after kainate-induced status epilepticus. J Neurosci. 2009; 29:2103-12]. Other studies suggests that the development of acquired epilepsy is at least initially progressive [Bertram and Cornett, 1993, 1994; French et al., 1993; Mathern et al., 1995; Hellier et al., 1998; Tasch et al., 1999; Fuerst et al., 2001; Gorter et al., 2001; Wuarin and Dudek, 2001]. Epileptogenesis occurs during the latent period. However, others state that the end of the latent period (i.e., the first clinical seizure) is not a terminal milestone for the mechanisms of epileptogenesis. Instead stating that the process of epileptogenesis is a continuous function of time that persists long after the first clinical seizure. A sigmoid function of seizure frequency versus time after the brain insult is a suitable representation of acquired epileptogenesis.

Despite decades of research, currently there is no single FDA-approved drug that truly prevents the development of epilepsy in people at risk. A variety of intervention approaches have been tested in animal models of epileptogenesis [Reddy D S and Kuruba R. Experimental models of status epilepticus and neuronal injury for evaluation of therapeutic interventions. Int. J. Mol. Sci. 2013, 14:18284-18318; Löscher W. The holy grail of epilepsy prevention: preclinical approaches to antiepileptogenic treatments. Neuropharmacology. 2019 Apr. 10. pii: S0028-3908(19)30128-5]. A number of clinical trials show a lack of antiepileptogenic efficacy of AEDs, including phenytoin and carbamazepine, in patients at high risk for developing epilepsy [Temkin N R. Antiepileptogenesis and seizure prevention trials with antiepileptic drugs, meta-analysis of controlled trials. Epilepsia 2001; 42: 515-524; Mani R, Pollard J, and Dichter M A. Human clinical trials in antiepileptogenesis. Neurosci Lett 2001; 497: 251-256]. There is a desperate need for drugs that truly prevent the development of epilepsy ('antiepileptogenic agents') or alter its natural course to delay the appearance or severity of epileptic seizures ('disease-modifying agents'). Epilepsy surgery is proposed to intractable patients after confirmation of diagnosis in order to control seizures as well as improve quality-of-life. There is desperate need for identification of new strategies to prevent epilepsy development. Therefore, there is a strong unmet need for efficient therapies averting the epileptogenesis and pharmacoresistance along with reversing or reducing long-term neuropsychiatric comorbid consequences of epilepsy.

In addition, there is a strong unmet need for efficient therapies for CNS conditions, including but limited to epilepsy, refractory epilepsy, status epilepticus, catamenial epilepsy; Alzheimer's disease, chronic pain, alcohol dependence, infantile spasm, traumatic brain injury, post-traumatic epilepsy, Fragile-X syndrome, chemical neurotoxicity, smoking cessation, bipolar disorder, depression, post-partum depression, premenstrual disorder, essential tremor, rare epilepsies including Rett's syndrome, Darvet syndrome and PHD19 condition.

SUMMARY

An embodiment of this disclosure provides compounds of the formula (A) in the form of a base or of an addition salt with an acid which is pharmaceutically acceptable, in the form of hydrates or of solvates, and also in the form of enantiomers, diastereoisomers and a mixture thereof. The disclosure also relates to processes for preparing said compounds, to pharmaceutical compositions containing a compound of general formula (A), and to the therapeutic use of said compounds and compositions.

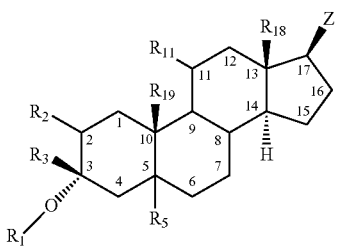

Formula (A)
wherein:
$R_1$ is hydrogen or substituted or unsubstituted $X_1$ or $X_2$ groups;
$R_2$ is hydrogen or substituted or unsubstituted alkyl or aryl or hetero groups;
$R_3$ is hydrogen or substituted or unsubstituted alkyl;
$R_5$ is hydrogen or substituted or unsubstituted alkyl;
$R_{11}$ is hydrogen or substituted or unsubstituted alkyl or hydroxyl or keto;
$R_{18}$ is hydrogen or substituted or unsubstituted alkyl;
$R_{19}$ is hydrogen or substituted or unsubstituted alkyl;
Z is a group of the formula (i) or (ii).
(i) Z is hydroxyl or substituted or unsubstituted groups according to the formula (ia) or (ib).

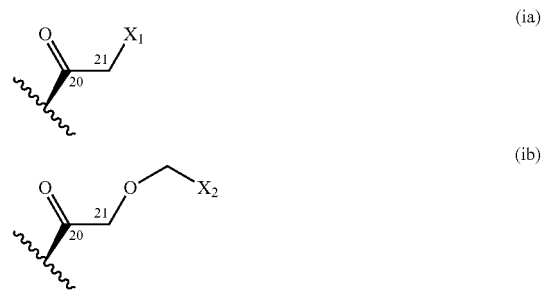

(ii) Z is substituted or unsubstituted isoxazole groups according to the formula (iia) or (iib).

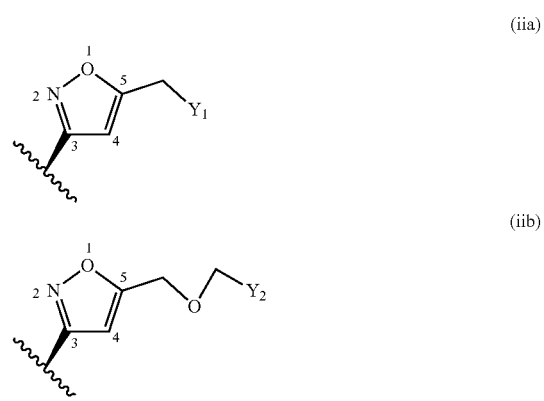

In (ia) and (ib), $X_1$ and $X_2$ are selected from a group consisting of a bond, a substituted or unsubstituted group. In Formula (iia) and (iib), $Y_1$ and $Y_2$ are selected from a group consisting of a bond, a substituted or unsubstituted group.

An embodiment of the disclosure is a compound of a structure:

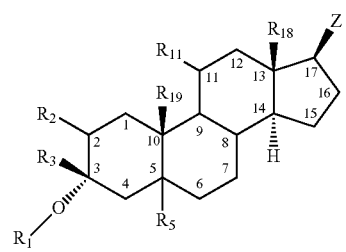

or a pharmaceutically acceptable salt, hydrate, or solvate thereof,
wherein:
$R_1$ is hydrogen or substituted or unsubstituted $X_1$ or $X_2$ groups, where $X_1$ and $X_2$ are selected from a group consisting of a bond, a substituted or unsubstituted group;

$R_2$ is hydrogen or substituted or unsubstituted alkyl or aryl or hetero groups;

$R_3$ is hydrogen or substituted or unsubstituted alkyl;

$R_5$ is hydrogen or substituted or unsubstituted alkyl;

$R_{11}$ is hydrogen or substituted or unsubstituted alkyl or hydroxyl or keto;

$R_{18}$ is hydrogen or substituted or unsubstituted alkyl;

$R_{19}$ is hydrogen or substituted or unsubstituted alkyl;

Z is hydroxyl or substituted or unsubstituted groups according to the formula (ia) or (ib):

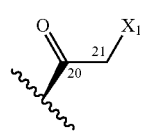
(ia)

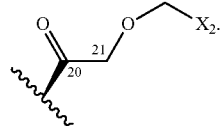
(ib)

In an embodiment, the structure is:

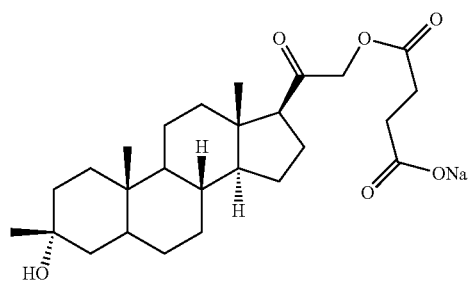
21-OH GX Succinate Sodium or a pharmaceutically acceptable salt, hydrate, or solvate thereof.

In an embodiment, the structure is:

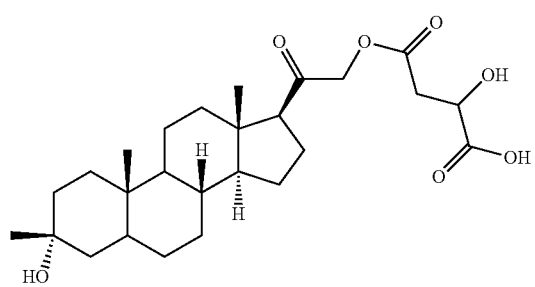
21-OH GX Malic Acid or a pharmaceutically acceptable salt, hydrate, or solvate thereof.

In an embodiment, the structure is:

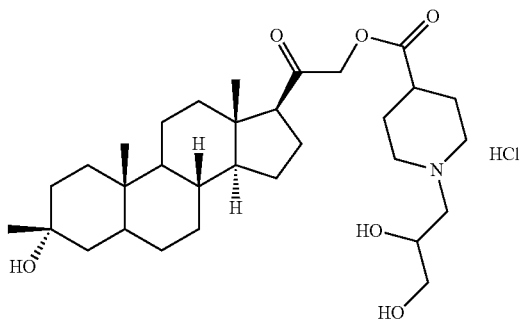
21-OH GX Piperidine Diol or a pharmaceutically acceptable salt, hydrate, or solvate thereof.

In an embodiment, the structure is:

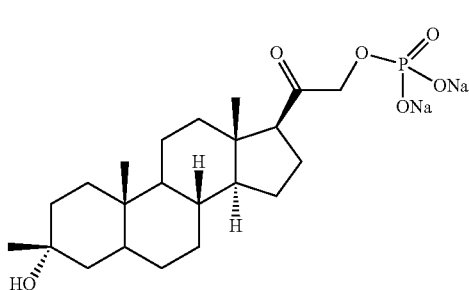
21-OH GX Phosphate Disodium or a pharmaceutically acceptable salt, hydrate, or solvate thereof.

In an embodiment, the structure is:

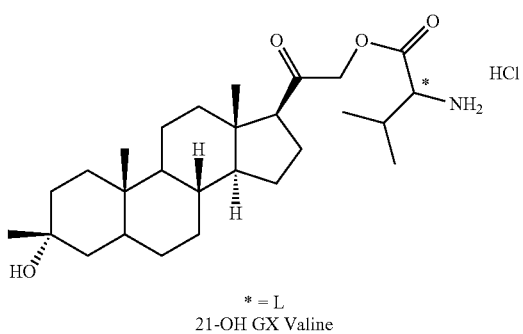
* = L
21-OH GX Valine or a pharmaceutically acceptable salt, hydrate, or solvate thereof.

In an embodiment, the structure is:

[Structure: 21-OH GX Lysine, * = L, with HCl]

or a pharmaceutically acceptable salt, hydrate, or solvate thereof.

In an embodiment, the structure is:

[Structure: 21-OH GX Methylphosphite Disodium]

or a pharmaceutically acceptable salt, hydrate, or solvate thereof.

In an embodiment, the structure is:

[Structure: 21-OH GX Carbamate]

or a pharmaceutically acceptable salt, hydrate, or solvate thereof.

An embodiment of the disclosure is a compound of a structure:

[Steroid structure with R groups labeled $R_1$, $R_2$, $R_3$, $R_5$, $R_{11}$, $R_{18}$, $R_{19}$, Z]

or a pharmaceutically acceptable salt, hydrate, or solvate thereof, wherein:

$R_1$ is hydrogen or substituted or unsubstituted $Y_1$ or $Y_2$ group, where $Y_1$ and $Y_2$ are selected from a group consisting of a bond, a substituted or unsubstituted groups;

$R_2$ is hydrogen or substituted or unsubstituted alkyl or aryl or hetero groups;

$R_3$ is hydrogen or substituted or unsubstituted alkyl;

$R_5$ is hydrogen or substituted or unsubstituted alkyl;

$R_{11}$ is hydrogen or substituted or unsubstituted alkyl or hydroxyl or keto;

$R_{18}$ is hydrogen or substituted or unsubstituted alkyl;

$R_{19}$ is hydrogen or substituted or unsubstituted alkyl;

Z is substituted or unsubstituted isoxazole groups according to the formula (iia) or (iib);

(iia)

[Isoxazole structure with $Y_1$]

(iib)

[Isoxazole structure with $Y_2$]

In an embodiment, the structure is:

[Structure: UCI-50027 Valine Citric Salt]

or a pharmaceutically acceptable salt, hydrate, or solvate thereof.

In an embodiment, the structure is:

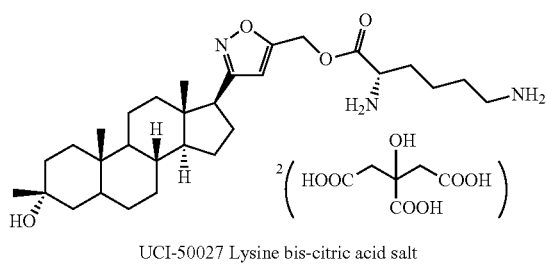

UCI-50027 Lysine bis-citric acid salt or a pharmaceutically acceptable salt, hydrate, or solvate thereof.

In an embodiment, the structure is:

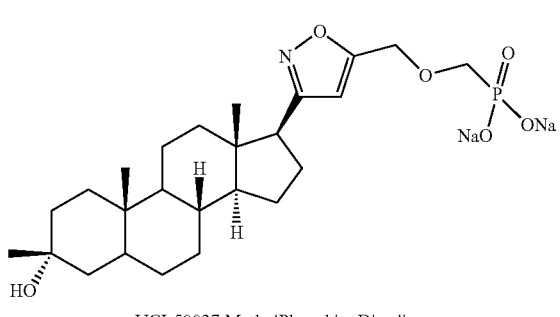

UCI-50027 MethylPhosphite Disodium or a pharmaceutically acceptable salt, hydrate, or solvate thereof.

In an embodiment, the structure is:

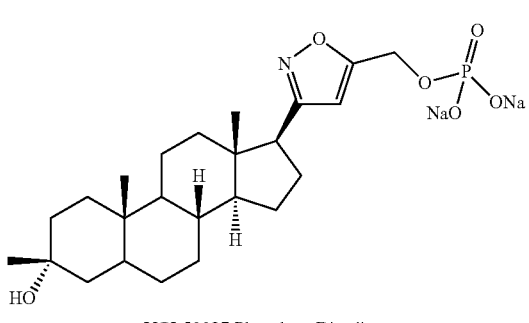

UCI-50027 Phosphate Disodium or a pharmaceutically acceptable salt, hydrate, or solvate thereof.

In an embodiment, the structure is:

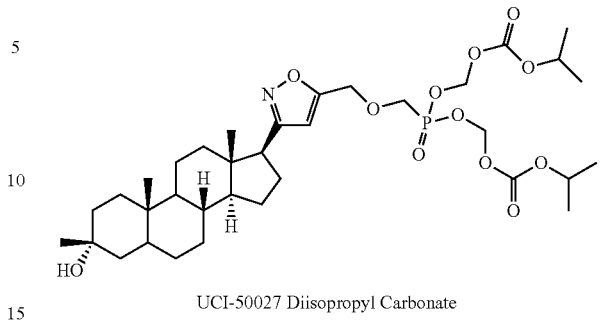

UCI-50027 Diisopropyl Carbonate or a pharmaceutically acceptable salt, hydrate, or solvate thereof.

An embodiment of the disclosure is a method for treating a disease or condition treatable by administering a neurosteroid derivative, comprising administering to a subject in need thereof a therapeutically effective amount of the compound of a structure:

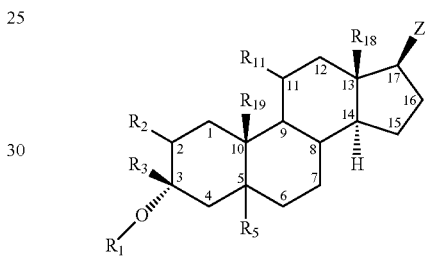

or a pharmaceutically acceptable salt, hydrate, or solvate thereof,
wherein:
$R_1$ is hydrogen or substituted or unsubstituted $X_1$ or $X_2$ groups,
where $X_1$ and $X_2$ are selected from a group consisting of a bond, a substituted or an unsubstituted group;
$R_2$ is hydrogen or substituted or unsubstituted alkyl or aryl or hetero groups;
$R_3$ is hydrogen or substituted or unsubstituted alkyl;
$R_5$ is hydrogen or substituted or unsubstituted alkyl;
$R_{11}$ is hydrogen or substituted or unsubstituted alkyl or hydroxyl or keto;
$R_{18}$ is hydrogen or substituted or unsubstituted alkyl;
$R_{19}$ is hydrogen or substituted or unsubstituted alkyl;
Z is hydroxyl or substituted or unsubstituted groups according to the formula (ia) or (ib):

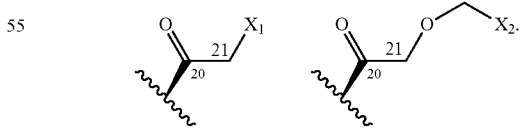

In an embodiment, the disease or condition is selected from the group consisting of epilepsy, chemical neurotoxicity, brain disorders and other dysfunction of the central nervous system.

In an embodiment, the compound is given to a patient by oral, parenteral, intravenous, transdermal, inhalation, intracerebral or topical administration in a suitable formulation.

An embodiment of the disclosure is a method for treating a disease or condition treatable by administering a neurosteroid derivative, comprising administering to a subject in need thereof a therapeutically effective amount of the compound of a structure:

or a pharmaceutically acceptable salt, hydrate, or solvate thereof,
wherein:

$R_1$ is hydrogen or substituted or unsubstituted $Y_1$ or $Y_2$ group, where $Y_1$ and $Y_2$ are selected from a group consisting of a bond, a substituted or an unsubstituted group;

$R_2$ is hydrogen or substituted or unsubstituted alkyl or aryl or hetero groups;

$R_3$ is hydrogen or substituted or unsubstituted alkyl;

$R_5$ is hydrogen or substituted or unsubstituted alkyl;

$R_{11}$ is hydrogen or substituted or unsubstituted alkyl or hydroxyl or keto;

$R_{18}$ is hydrogen or substituted or unsubstituted alkyl;

$R_{19}$ is hydrogen or substituted or unsubstituted alkyl;

Z is substituted or unsubstituted isoxazole groups according to the formula (iia) or (iib);

(iia)

(iib)

In an embodiment, the disease or condition is selected from the group consisting of epilepsy, chemical neurotoxicity, brain disorders and other dysfunction of the central nervous system.

In an embodiment, the compound is given to a patient by oral, parenteral, intravenous, transdermal, inhalation, intracerebral or topical administration in a suitable formulation.

The present disclosure is further directed to a pharmaceutically acceptable salt of the noted compounds, or alternatively to analogs or prodrugs thereof.

The foregoing has outlined rather broadly the features of the present disclosure in order that the detailed description that follows may be better understood. Additional features and advantages of the disclosure will be described hereinafter, which form the subject of the claims.

BRIEF DESCRIPTION OF THE DRAWINGS

In order that the manner in which the above-recited and other enhancements and objects of the disclosure are obtained, a more particular description of the disclosure briefly described above will be rendered by reference to specific embodiments thereof which are illustrated in the appended drawings. Understanding that these drawings depict only typical embodiments of the disclosure and are therefore not to be considered limiting of its scope, the disclosure will be described with additional specificity and detail through the use of the accompanying drawings in which.

DETAILED DESCRIPTION

Figure 1:
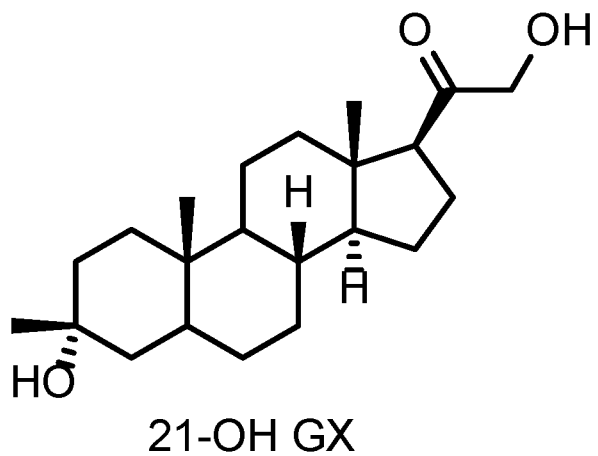
FIG. 1. Illustrates the structure of 21-OH Ganaxolone (21-OH GX).
Figure 2:
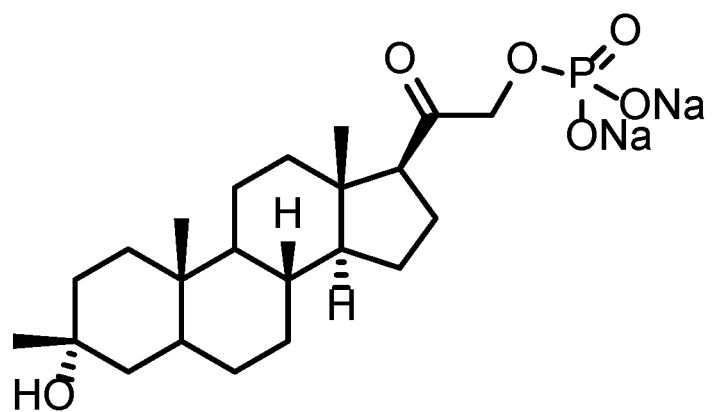
FIG. 2. Illustrates the structure of 21-OH GX Phosphate Disodium.
Figure 3:
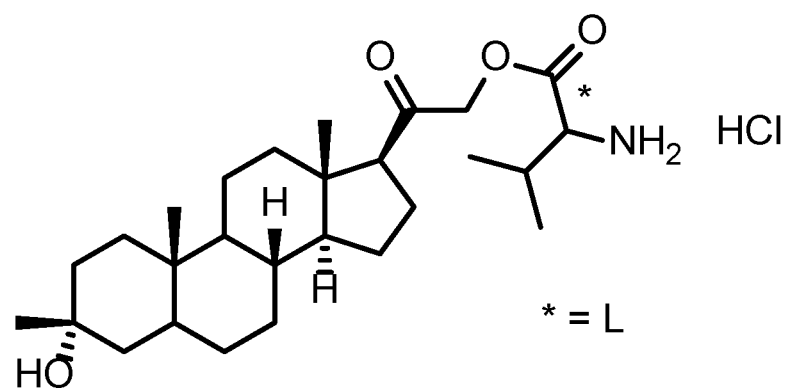
FIG. 3. Illustrates the structure of 21-OH GX Valine.
Figure 4:
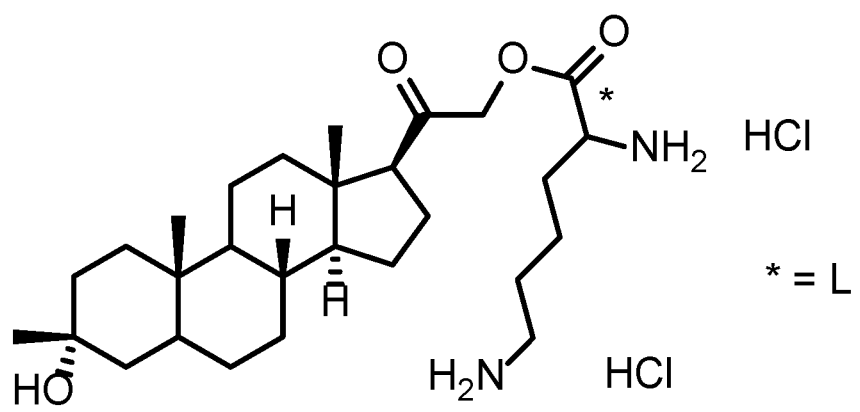
FIG. 4. Illustrates the structure of 21-OH GX Lysine.
Figure 5:
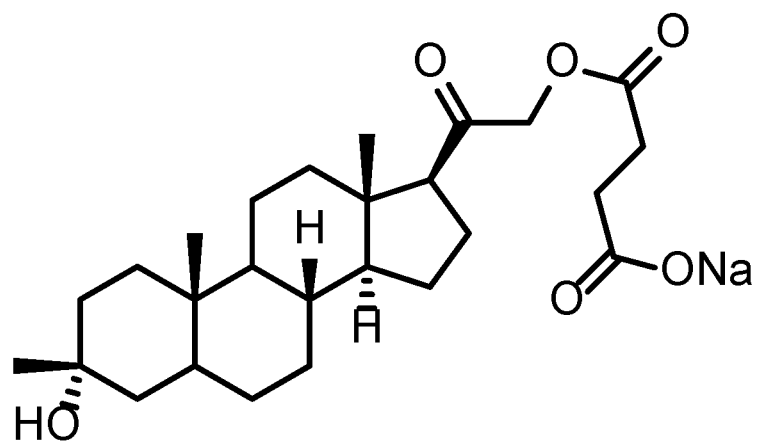
FIG. 5. Illustrates the structure of 21-OH GX Succinate Sodium.
Figure 6:
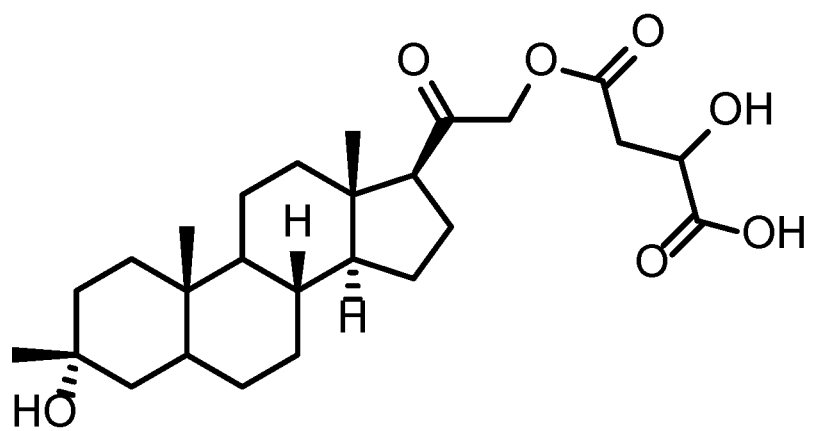
FIG. 6. Illustrates the structure of 21-OH GX Malic Acid.
Figure 7:
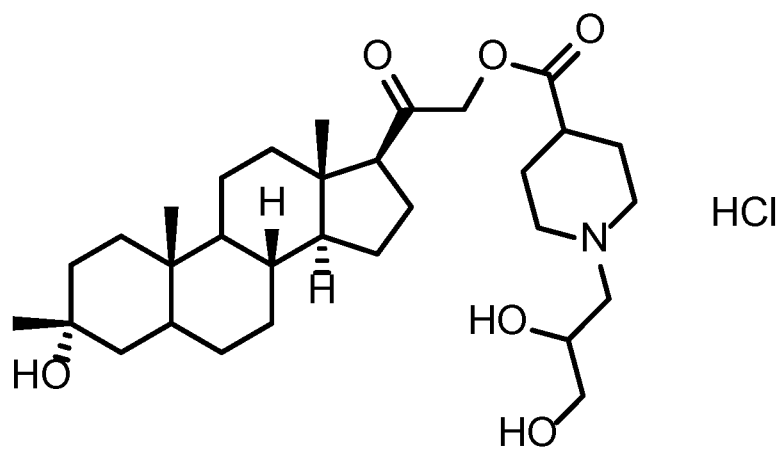
FIG. 7. Illustrates the structure of 21-OH GX Piperdine Diol.
Figure 8:
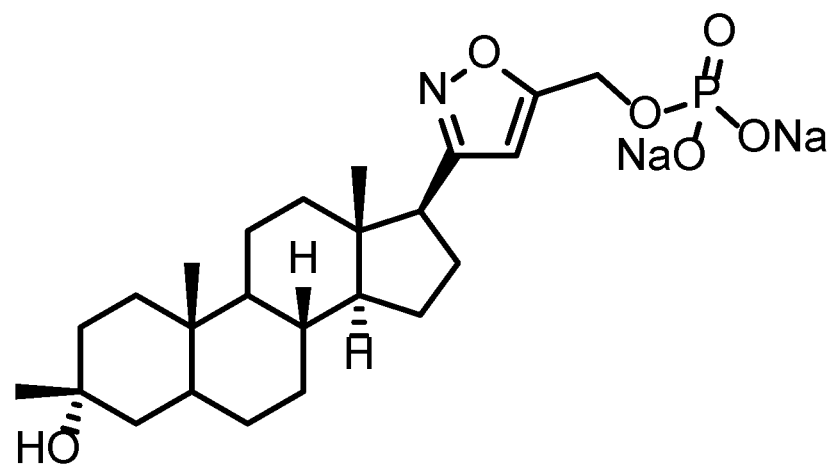
FIG. 8. Illustrates the structure of UCI-50027 Phosphate Disodium.
Figure 9:
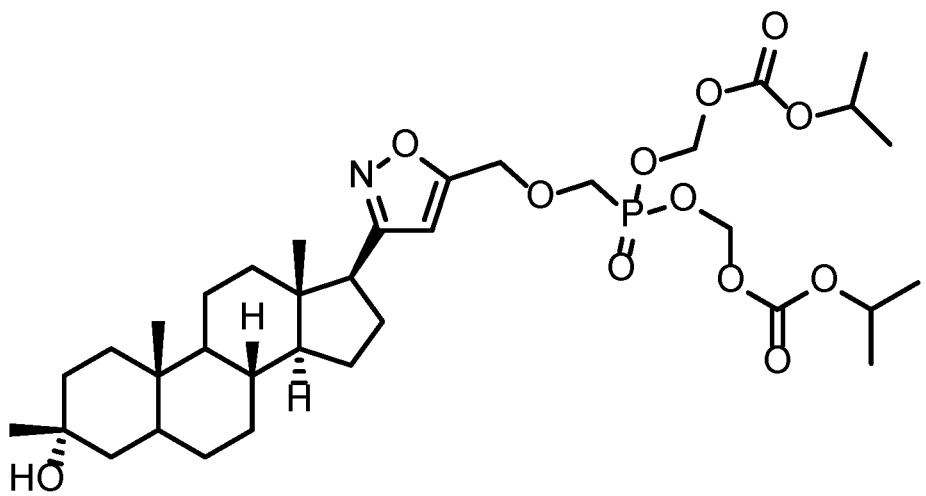
FIG. 9. Illustrates the structure of UCI-50027 Diisopropyl Carbonate.
Figure 10:
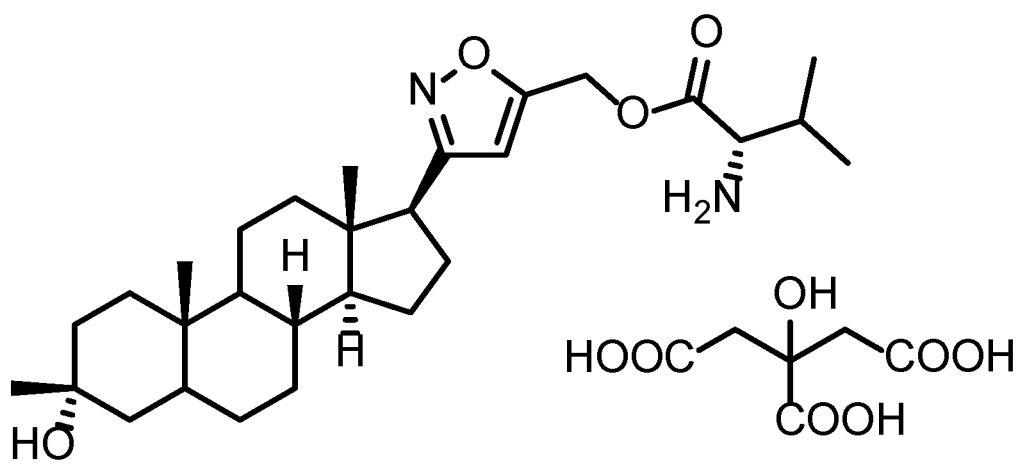
FIG. 10. Illustrates the structure of UCI-50027 Valine Citric Salt.
Figure 11:
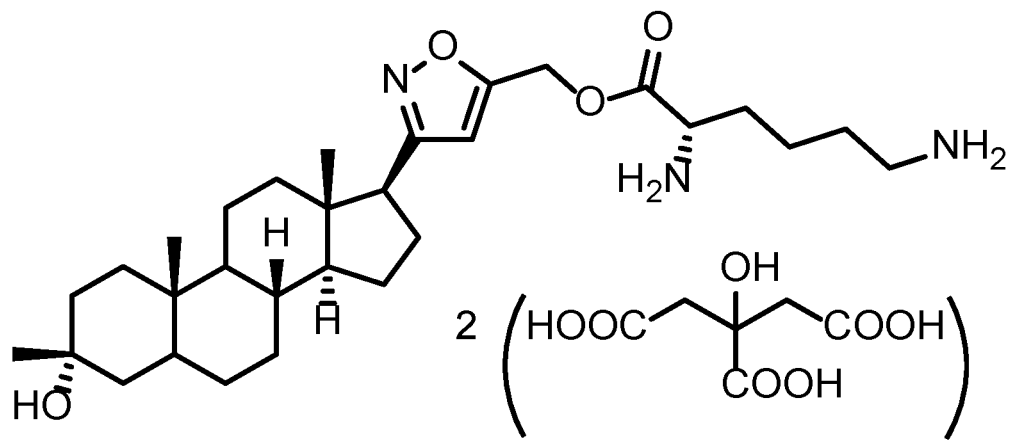
FIG. 11. Illustrates the structure of UCI-50027 Lysine bis-citric acid salt.
Figure 12:
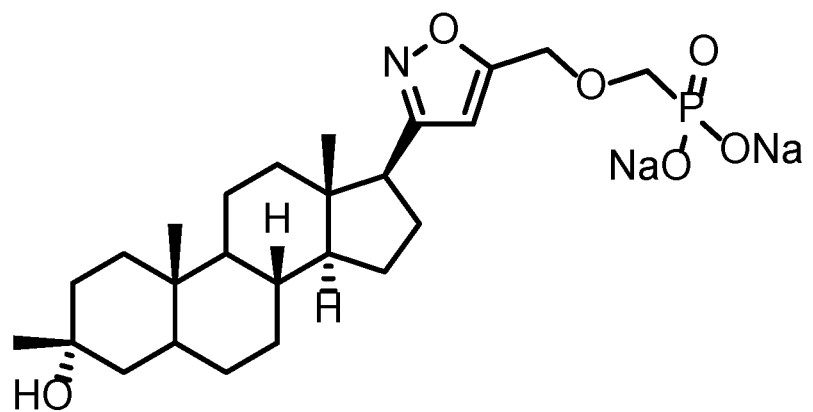
FIG. 12. Illustrates the structure of UCI-50027 MethylPhosphite Disodium.
Figure 13:
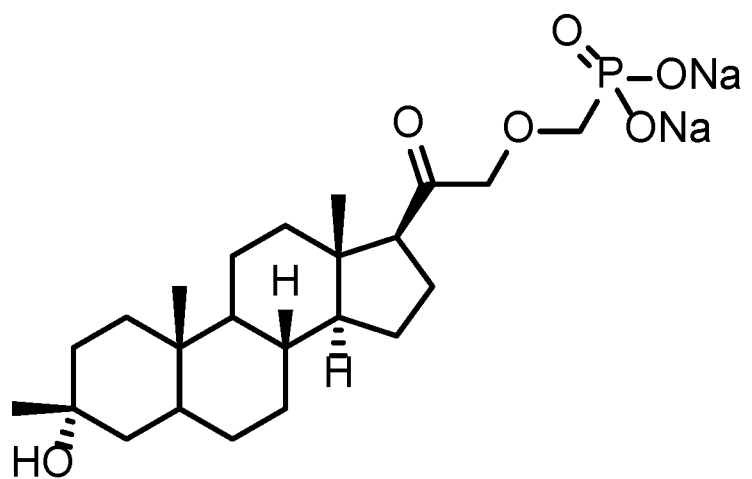
FIG. 13. Illustrates the structure of 21-OH GX MethylPhosphite Disodium.
Figure 14:
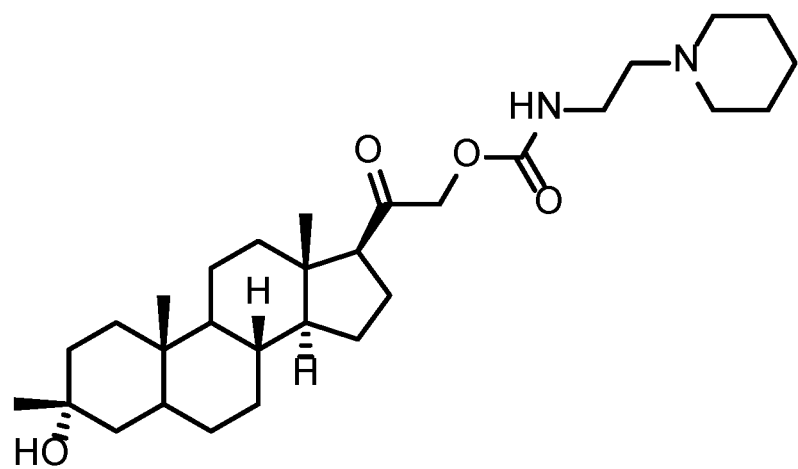
FIG. 14. Illustrates the structure of 21-OH GX Carbamate.

The particulars shown herein are by way of example and for purposes of illustrative discussion of the preferred embodiments of the present disclosure only and are presented in the cause of providing what is believed to be the most useful and readily understood description of the principles and conceptual aspects of various embodiments of the disclosure. In this regard, no attempt is made to show structural details of the disclosure in more detail than is necessary for the fundamental understanding of the disclosure, the description taken with the drawings making apparent to those skilled in the art how the several forms of the disclosure may be embodied in practice.

The following definitions and explanations are meant and intended to be controlling in any future construction unless clearly and unambiguously modified in the following examples or when application of the meaning renders any construction meaningless or essentially meaningless. In cases where the construction of the term would render it meaningless or essentially meaningless, the definition should be taken from Webster's Dictionary $3^{rd}$ Edition.

The term "halogen" means a fluorine, a chlorine, a bromine or an iodine.

The term "halo" means fluoro, chloro, bromo, or iodo, preferably fluoro and chloro.

The term "alkyl group" means a saturated, linear or branched, aliphatic group. Examples of an alkyl group include the methyl, ethyl, n-propyl, n-butyl, n-pentyl, n-hexyl, n-heptyl, 1-methylethyl, 1-methylpropyl, 2-methylpropyl, 1,1-dimethylethyl, 1-methylbutyl, 2-methylbutyl, 3-methylbutyl, 1,1-dimethylpropyl, 1,2-dimethylpropyl, 2,2-dimethylpropyl, 1-methylpentyl, 2-methylpentyl, 3-methylpentyl, 4-methylpentyl, 1,1-dimethylbutyl, 1,2-dimethylbutyl, 1,3-dimethylbutyl, 2,2-dimethylbutyl, 2,3-dimethylbutyl, 3,3-dimethylbutyl, 1,1,2-trimethylpropyl, 1,2,2-trimethylpropyl, 1-ethyl-1-methyl-propyl, 1-ethyl-2-methylpropyl, 1-ethylbutyl, 2-ethylbutyl, 1-methylhexyl, 2-methylhexyl, 3-methylhexyl, 4-methylhexyl, 5-methylhexyl, 1,1-dimethylpentyl, 1,2-dimethylpentyl, 1,3-dimethylpentyl, 1,4-dimethylpentyl, 2,2-dimethylpentyl, 2,3-dimethylpentyl, 2,4-dimethylpentyl, 3,3-dimethylpentyl, 3,4-dimethylpentyl, 4,4-dimethylpentyl, 1,1,2-trimethylbutyl, 1,1,3-trimethylbutyl, 1,2,2-trimethylbutyl, 1,2,3-tri-methylbutyl, 1,3,3-trimethylbutyl, 2,2,3-trimethylbutyl, 2,3,3-trimethylbutyl, 1,1,2,2-tetramethylpropyl, 1-ethylpentyl, 2-ethylpentyl, 3-ethylpentyl, 1-ethyl-1-methylbutyl, 1-ethyl-2-methylbutyl, 1-ethyl-3-methylbutyl, 2-ethyl-1-methylbutyl, 2-ethyl-2-methylbutyl, 2-ethyl-3-methylbutyl, 1-propylbutyl, 1-(1-methylethyl)butyl or 1-(1-methylethyl)-2-methylpropyl groups.

The term "lower alkyl" means an alkyl group having 1 to 6 carbons linear or branched.

The term "alkenyl group" means a mono- or polyunsaturated, linear or branched, aliphatic group comprising, for example, one or two ethylenic unsaturations.

The term "alkynyl group" means a mono- or polyunsaturated, linear or branched, aliphatic group comprising, for example, one or two acetylenic unsaturations.

The term "cycloalkyl group" means cyclopropyl, cyclobutyl, cyclopentyl, cyclohexyl, cycloheptyl, bicyclo[2.2.1]heptyl, cyclooctyl, bicyclo[2.2.2]octyl, bicyclo[3.2.1]octyl or adamantyl.

The term "acyl" means a radical —C(O)R', where R' is hydrogen, alkyl, alkenyl, cycloalkyl, cycloalkylalkyl, phenyl or phenylalkyl wherein alkyl, cycloalkyl, cycloalkylalkyl, and phenyl-alkyl are as defined herein. Representative examples include, but are not limited to formyl, acetyl, cylcohexylcarbonyl, cyclohexylmethylcarbonyl, benzoyl, benzylcarbonyl, and the like.

The term "alkoxyl" means a radical —OR where R is an alkyl as defined above. Representative examples include, but are not limited to methoxy, ethoxy, propoxy, butoxy, t-butoxyl and the like.

The term "aryl" means a monovalent monocyclic or polycyclic aromatic hydrocarbon radical; it includes, but is not limited to, phenyl and naphthyl.

The term "heteroaryl" means a monovalent monocyclic or bicyclic radical of 5 to 12 ring atoms having at least one aromatic ring containing one, two, or three ring heteroatoms independently selected from N, O, or S, the remaining ring atoms being C, with the understanding that the attachment point of the heteroaryl radical will be on an aromatic ring. More specifically the term heteroaryl includes, but is not limited to, pyridyl, furanyl, thienyl, thiazolyl, isothiazolyl, triazolyl, imidazolyl, isoxazolyl, pyrrolyl, pyrazolyl, pyrimidinyl, benzofuranyl, tetrahydrobenzofuranyl, isobenzofuranyl, benzothiazolyl, benzoisothiazolyl, benzotriazolyl, indolyl, isoindolyl, benzoxazolyl, quinolyl, tetrahydroquinolinyl, isoquinolyl, benzimidazolyl, benzisoxazolyl or benzothienyl, imidazo[1,2-a]-pyridinyl, and imidazo[2,1-b]thiazolyl.

The term "heterocyclic ring" means a saturated or unsaturated non-aromatic cyclic radical of 3 to 8 ring atoms in which one or two ring atoms are heteroatoms independently selected from N, O, or $S(O)_e$ (where e is an integer from 0 to 2).

The term "substituent" means hydrogen, halogen, alkyl, alkoxyl, cycloalkyl, cyano (CN), OH, acyl, haloalkyl, heteroaryl, $C(halogen)_3$, CN, $C(=O)CH_3$, $C(=O)NQ_1Q_2$, $N_3$, NCS, $NO_2$, $NQ_1Q_2$ wherein $Q_1$ and $Q_2$ each is independently selected from H and alkyl.

Methods for Using Neurosteroid Derivatives

The disclosure further relates to derivative neurosteroid compounds of ganaxolone (GX) and its 17-isooxazole analog (UCI-50027), and CNS selective GABA-A receptor modulators, to the preparation thereof and to the therapeutic use thereof, wherein said compounds are of general formulas (A). These compounds are potentially useful in treating brain disorders including, but not limited to seizures, epilepsy, anxiety, depression, cognition, behavioral and neurological effects, and central nervous system dysfunction.

In a further aspect, the present disclosure provides methods for using neurosteroid derivatives. In an embodiment, the Formula (A) neurosteroid derivatives can be used as therapeutic agents, such as for treating seizures, epilepsy, and neurobehavioral effects and dysfunction.

In an embodiment, the neurosteroid derivatives of the disclosure can be used for the treatment of disorders associated with the central nervous system, which include, but are not limited epilepsy, refractory epilepsy, status epilepticus, catamenial epilepsy; Alzheimer's disease, chronic pain, alcohol dependence, alcohol withdrawal, drug addiction, infantile spasm, traumatic brain injury, post-traumatic epilepsy, Fragile-X syndrome, chemical neurotoxicity, smoking cessation, bipolar disorder, anxiety, generalized anxiety syndrome, panic attacks, depression, postpartum depression, premenstrual disorder, essential tremor, rare epilepsies including Rett's syndrome, Dravet syndrome and PHD19 condition.

In an embodiment, for therapeutic applications, the neurosteroid derivatives of the disclosure can be formulated with a pharmaceutically acceptable carrier suitable for the desired method of administration. Pharmaceutically acceptable carriers are known in the art. Pharmaceutically acceptable carriers include, but are not limited to a cream, emulsion, gel, liposome, nanoparticle, ointment, polymeric micelle, a protein, and microspheres. In an embodiment, the neurosteroid derivatives of the disclosure can be formulated with a pharmaceutically acceptable excipient. Pharmaceutically acceptable excipients are known in the art. Pharmaceutically acceptable excipients include, but are not limited to antiadherents, binders, coatings, colors, disintegrants, flavors, glidants, lubricants, preservatives, sorbents, sweeteners, and vehicles. In an embodiment, the neurosteroid derivatives of this disclosure can be administered systemically by oral, intravenous, parenteral injections, inhalation, transdermal, intracerebral or topical administration.

Methods for Using Neurosteroid Derivatives

The disclosure further relates to derivative neurosteroid compounds of ganaxolone (GX) and its 17-isooxazole analog (UCI-50027), and CNS selective GABA-A receptor modulators, to the preparation thereof and to the therapeutic use thereof, wherein said compounds are of general formulas (A). These compounds are potentially useful in treating brain disorders including, but not limited to, seizures, epilepsy, cognition, behavioral and neurological effects, and central nervous system dysfunction.

In a further aspect, the present disclosure provides methods for using neurosteroid derivatives. In an embodiment, the Formula (A) neurosteroid derivatives can be used as therapeutic agents, including, but not limited to use for treating seizures, epilepsy, and neurobehavioral effects and dysfunction.

In an embodiment, the neurosteroid derivatives of the disclosure can be used for the treatment of disorders associated with central nervous system, which include, but are not limited to epilepsy, refractory epilepsy, status epilepticus, catamenial epilepsy; Alzheimer's disease, chronic pain, alcohol dependence, alcohol withdrawal, drug addiction, infantile spasm, traumatic brain injury, post-traumatic epilepsy, Fragile-X syndrome, chemical neurotoxicity, smoking cessation, bipolar disorder, anxiety, generalized anxiety syndrome, panic attacks, depression, postpartum depression, premenstrual disorder, essential tremor, rare epilepsies including Rett's syndrome, Dravet syndrome and PHD19 condition.

In an embodiment, for therapeutic applications, the neurosteroid derivatives of the disclosure can be formulated with a pharmaceutically acceptable carrier suitable for the desired method of administration. Pharmaceutically acceptable carriers are known in the art. Pharmaceutically acceptable carriers include, but are not limited to a cream, emulsion, gel, liposome, nanoparticle, ointment, polymeric micelle, a protein, and microspheres. In an embodiment, the neurosteroid derivatives of this disclosure can be administered systemically by oral, intravenous, parenteral injections, inhalation, transdermal, intracerebral or topical administration. In an embodiment, the neurosteroid derivatives of the disclosure can be formulated with a pharmaceutically acceptable excipient. Pharmaceutically acceptable excipients are known in the art. Pharmaceutically acceptable excipients include, but are not limited to antiadherents, binders, coatings, colors, disintegrants, flavors, glidants, lubricants, preservatives, sorbents, sweeteners, and vehicles.

Ganaxolone and its analog (UCI-17-isooxazole) are neurosteroid analogs and CNS-selective GABA-A receptor modulators that act on well-characterized targets in the brain. They both have demonstrated the anti-seizure and anxiolytic effect; however, their bioavailability are extremely low due to their high lipophilicity and low aqueous solubility. Thus, a prodrug is a viable approach to improve their bioavailability. Various types of analogs or prodrugs of ganaxolone and UCI-17-isooxazole have been synthesized in >250 mg quantity with >95% purity. Their aqueous solubility and stability were also measured. In general, great improvements were observed over the parent compounds.

Parent drugs
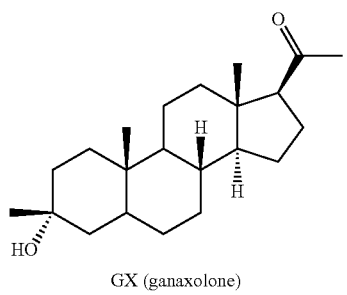
GX (ganaxolone)
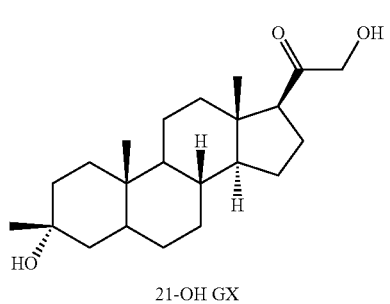
21-OH GX
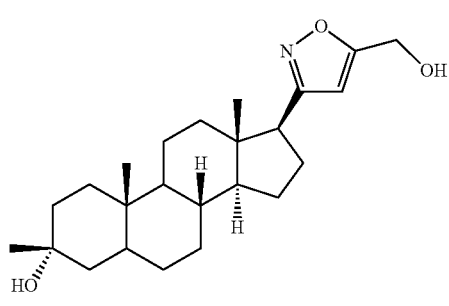
UCI-50027
Analogs or prodrugs
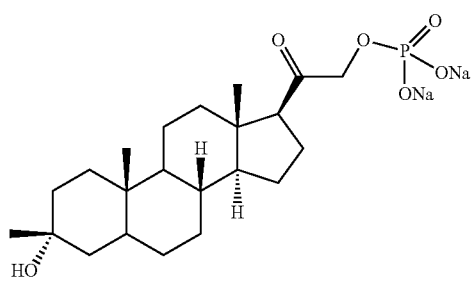
21-OH GX Phosphate Disodium
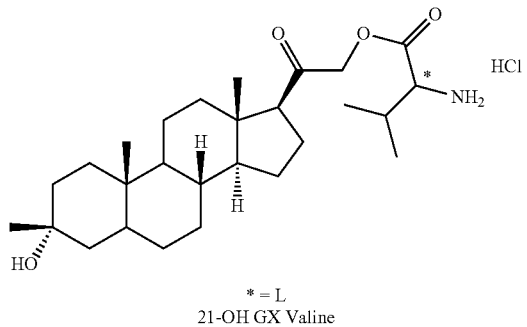
* = L
21-OH GX Valine
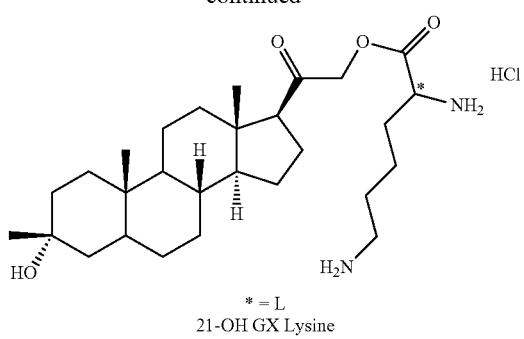
* = L
21-OH GX Lysine
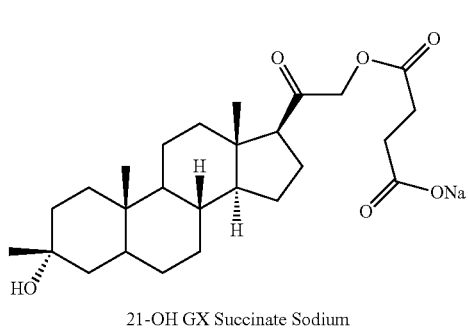
21-OH GX Succinate Sodium
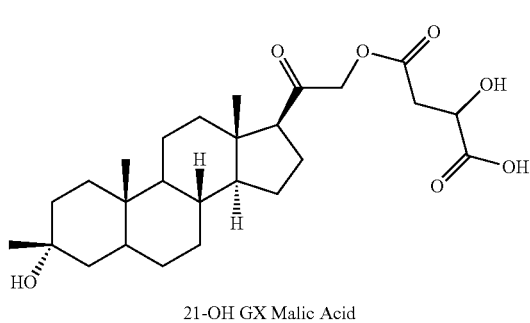
21-OH GX Malic Acid
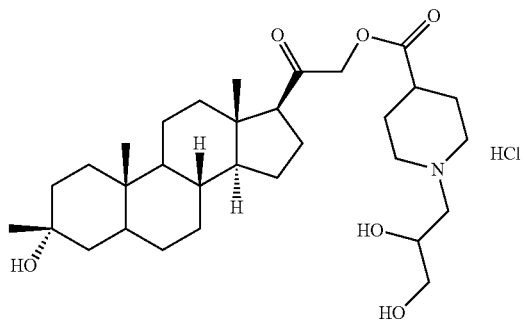
21-OH GX Piperidine Diol
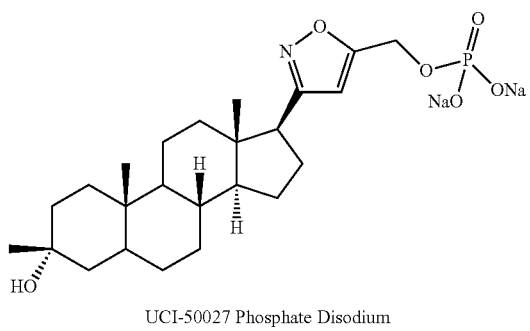
UCI-50027 Phosphate Disodium

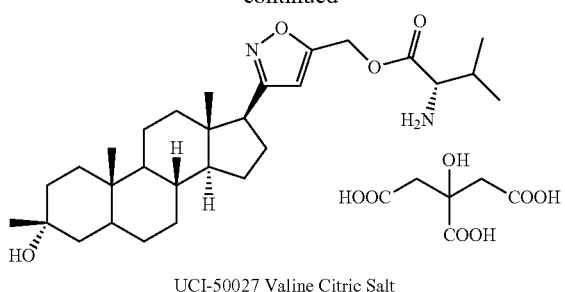

UCI-50027 Valine Citric Salt

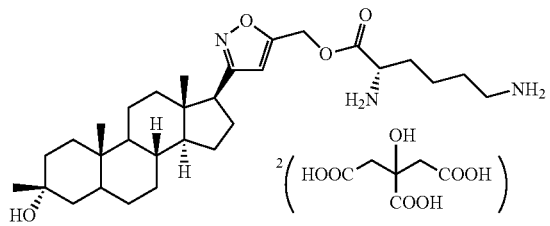

UCI-50027 Lysine bis-citric acid salt

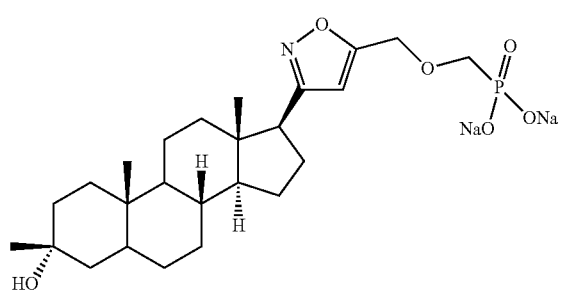

UCI-50027 MethylPhosphite Disodium

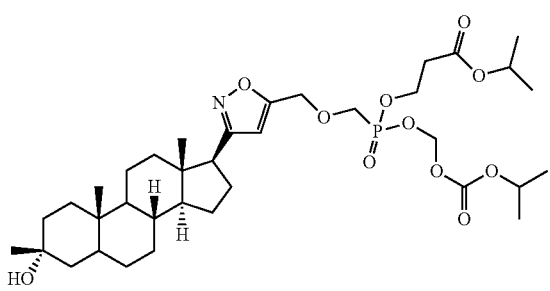

UCI-50027 Diisopropyl Carbonate

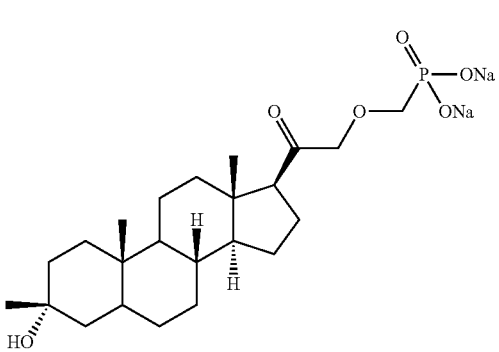

21-OH GX Methylphosphite Disodium

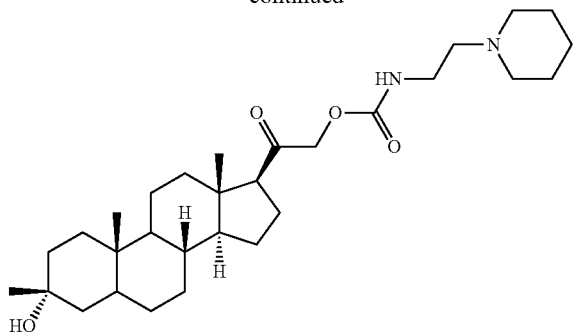

21-OH GX Carbamate

EXAMPLES

The following examples are provided for the purpose of illustrating, not limiting the disclosure.

Example 1. Preclinical Efficacy Studies of Neurosteroid Derivatives in Seizure Models Many new derivatives of neurosteroid molecules were synthesized and their effect in three standard seizure models was demonstrated: (i) hippocampus kindling seizures; (ii) 6-Hz limbic-seizures; and (iii) pilocarpine status epilepticus. For comparison, parallel experiments were conducted with ganaxolone. These results are summarized in Table 1.

TABLE 1

Anticonvulsant and protective (ED50 values, mg/kg, s.c.) of neurosteroid derivatives.

| Compound | Kindling model | 6-Hz model | Pilocarpine model |
| --- | --- | --- | --- |
| 21-OH-ganaxolone | 3.8 mg/kg | 2.6 mg/kg | 6 mg/kg |
| 21-OH-ganaxolone phosphate | 3.5 mg/kg | 2.8 mg/kg | 6 mg/kg |
| 21-OH-ganaxolone succinate | 3.5 mg/kg | 2.1 mg/kg | 6 mg/kg |
| 21-OH-ganaxolone valine | 3.3 mg/kg | 2.6 mg/kg | 6 mg/kg |
| Ganaxolone | 3.5 mg/kg | 2 mg/kg | 6 mg/kg |

Figure 15:
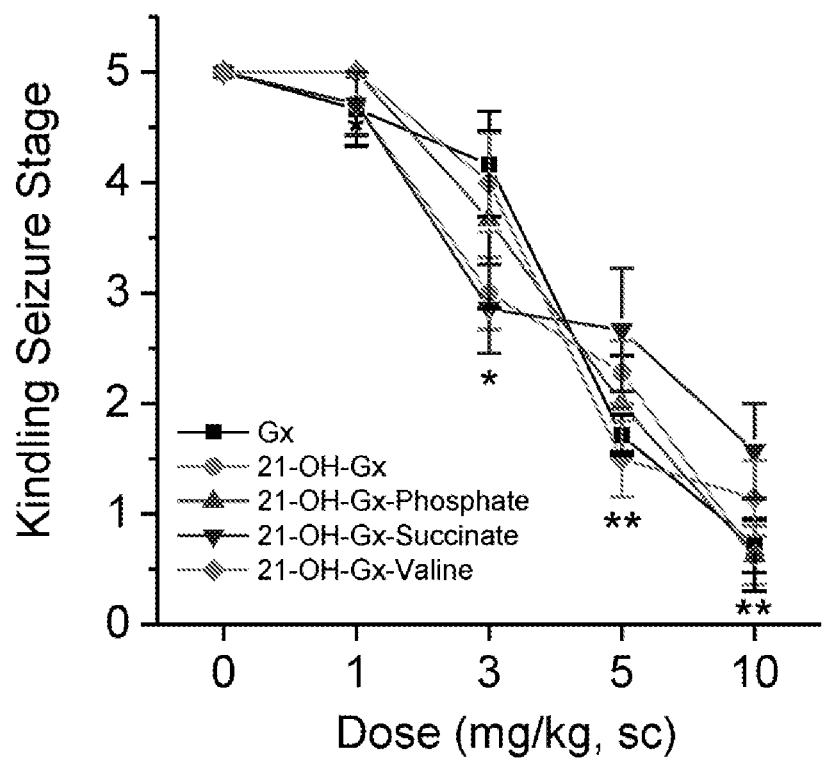
FIG. 15. Protective effect of neurosteroid derivatives in the hippocampus kindling model of epilepsy in mice: suppression of behavioral seizure activity. Mice that were fully kindled by daily stimulation until the point of consistent stage 5 (generalized) seizures were injected intraperitoneally with a test compound 15 minutes before stimulation. Each point represents the mean±S.E.M. of data from six to eight animals.
Figure 16:
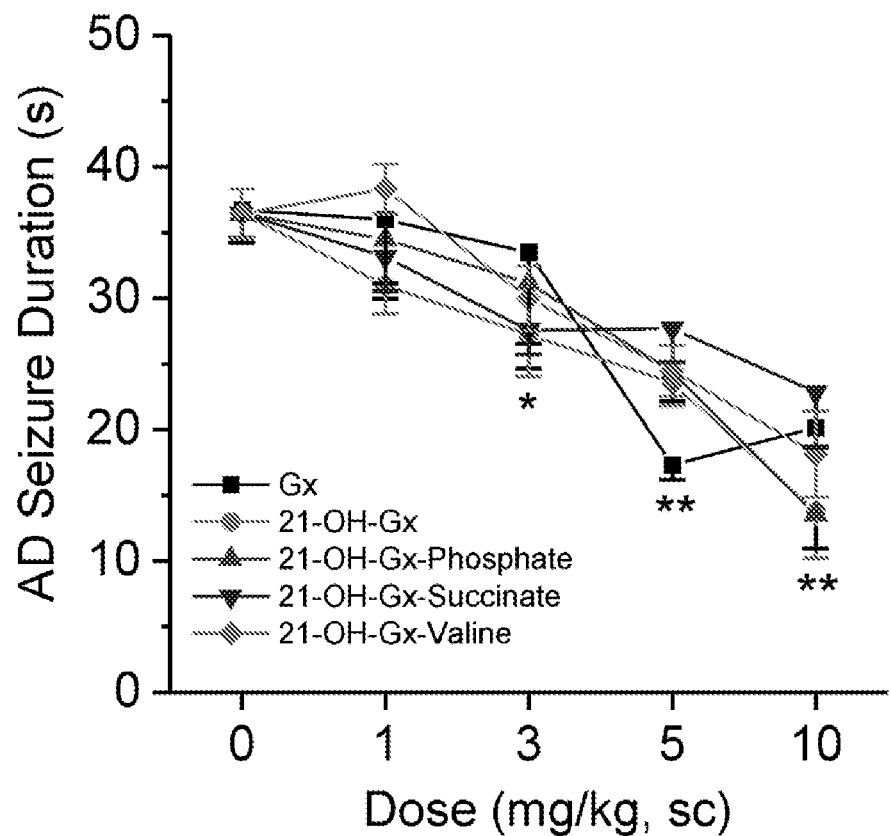
FIG. 16. Protective effect of neurosteroid derivatives in the hippocampus kindling model of epilepsy in mice: EEG after discharge duration. Mice that were fully kindled by daily stimulation until the point of consistent stage 5 (generalized) seizures were injected intraperitoneally with a test compound 15 minutes before stimulation. Each point represents the mean±S.E.M. of data from six to eight animals.

Kindling model: As shown in FIGS. 15 and 16, all four neurosteroid derivatives produced a dose-dependent suppression of behavioral seizure activity (FIG. 15) and EEG after discharge duration (FIG. 16) in the hippocampus kindling model, a model of complex partial seizures. A significant protection was evident both at 3 and 5 mg/kg within 15-min after administration. At the highest dose tested (10 mg/kg), seizures were nearly completely suppressed by all four neurosteroid derivatives. The ED50 of the neurosteroid derivatives for suppression of seizures was comparable to that of ganaxolone (see Table 1).

Figure 17:
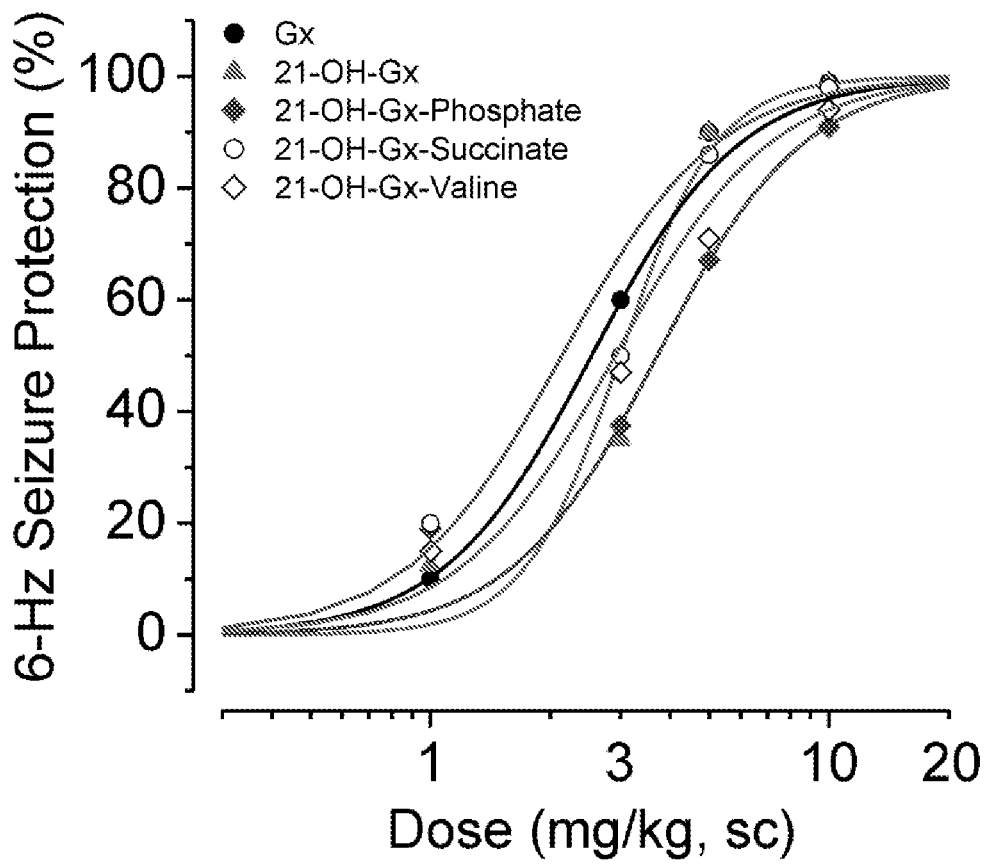
FIG. 17. Dose-dependent protective effect of neurosteroid derivatives in 6-Hz model of acute seizures. Test neurosteroid compounds were administered 15 minutes before 6-Hz stimulation. Points signify percentage of animals protected from seizures within a group of six to eight at a given dose. Percent seizure occurrence considers visible symptoms of any length or magnitude as a full seizure.

6-Hz seizure model: As shown in FIG. 17, all four neurosteroid derivatives produced powerful anticonvulsant effects in the 6-Hz model, a model of limbic partial seizures that are highly sensitive to antiepileptic drugs that act primarily at GABA-A receptors. Animals were treated with neurosteroid derivatives by SC injection and then were subjected to 6-Hz stimulation 15 minutes after test dosing. Dose-response curves were derived for each neurosteroid derivative, and potency was determined as ED50 value (Table 1). The protective potency of the neurosteroid derivatives was similar to ganaxolone (FIG. 17). In fact, all four neurosteroid derivatives exhibited greater protective effects in the 6-Hz test, which could be due to improved pharmacokinetic distribution and bioavailability in the brain.

Pilocarpine SE model: As shown in Table 1, all four neurosteroid derivatives protected pilocarpine-induced SE in a dose-dependent fashion. Also, test compounds improved the survival rate from SE-related mortality.

Figure 18A:
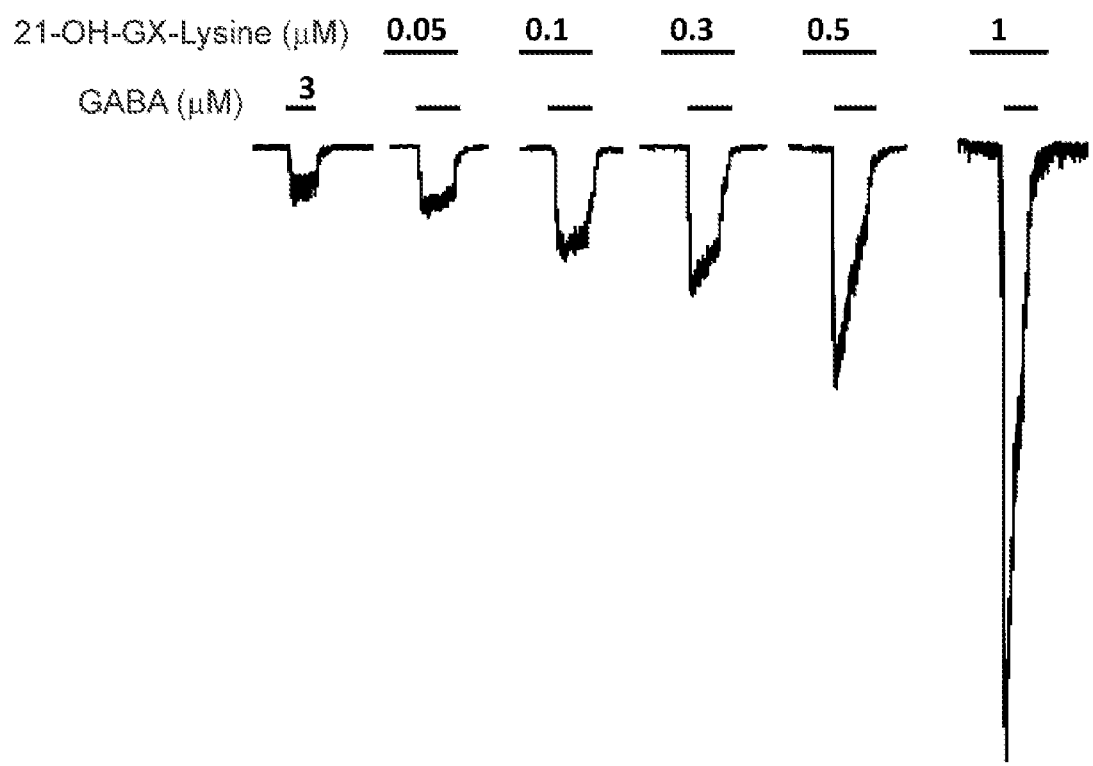
FIG. 18A-18B. Neurosteroid analogs allosteric activation of GABA-gated currents in acutely dissociated mouse dentate gyrus granule cells. Test compounds displayed a concentration-dependent effect on increasing the GABA-gated chloride currents in neurons. (18A) Representative whole-cell current recordings of 21-OH-GX-Lysine. (18B) Concentration-response of neurosteroid analog-modulated allosteric potentiation of chloride currents in dentate gyrus granule cells. Each point represents mean±SEM of data from 5 to 10 cells.
Figure 18B:
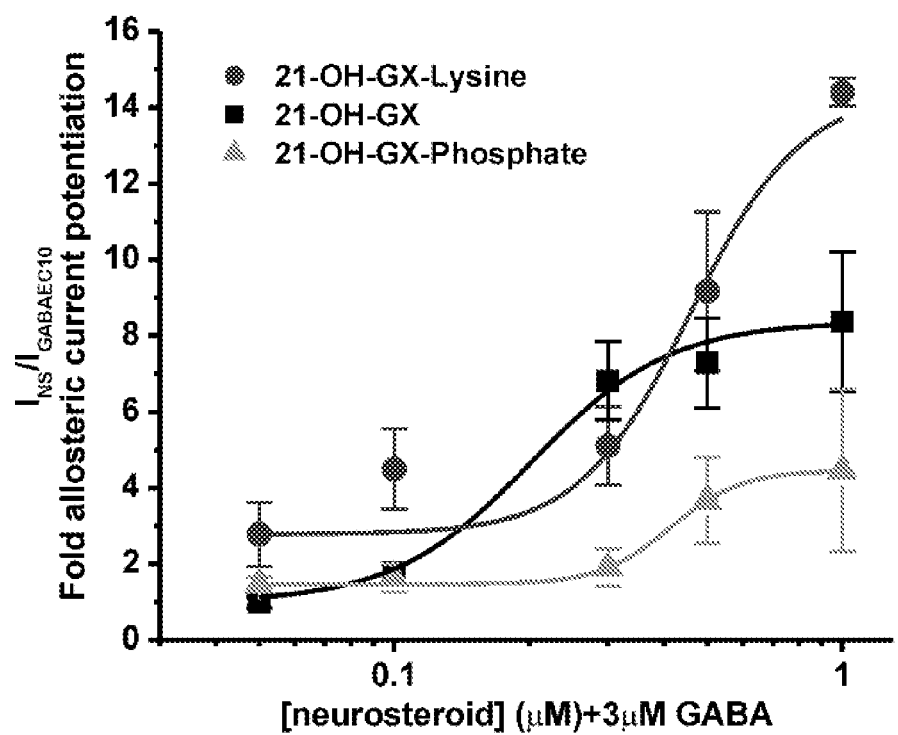

Neurosteroid derivatives were tested for their effect on synaptic and extrasynaptic GABA-A receptors in dentate gyrus granule cells (DGGCs) in the hippocampus. Since the expression of δ-subunit is higher in DGGCs than in other neurons, DG neurons were utilized for testing the effect of neurosteroid analogs on whole-cell and extrasynaptic tonic currents. To determine the modulatory effects of neurosteroid analogs on whole-cell GABA-gated currents, neurosteroid analogs were studied in native neurons using patch-clamp electrophysiology. GABA-A receptor currents were recorded from acutely dissociated, voltage-clamped DGGCs or CA1PCs from adult male mice in whole-cell mode. 3 μM GABA was utilized, which was within the range of $EC_{10}$ response for both DGGCs to determine a baseline response and allosteric activation by tested compounds. A test neurosteroid analog produced allosteric potentiation of GABA currents in a concentration-dependent manner (FIG. 18A). Concentration-response plots were generated to determine allosteric potentiation by neurosteroid analogs (FIG. 18B). Due to the lack of a response plateau, a nonlinear curve could not be fit to the data. Based on neuron responses, 1 μM GX-mediated current was denoted as the constrained maximum efficacy response for allosterically modulated activity (FIG. 18B). To verify the target specificity of test compound inhibitory activity in native neurons, the blockade of GABAergic currents with specific GABA-A receptor antagonists was studied. At 10 μM, the competitive antagonists bicuculline or gabazine (GBZ) completely blocked whole-cell GABA-gated current potentiation by GX. When the antagonists were removed by washing, the GX-potentiated GABA-gated currents returned to the same level as before the application of antagonists. These results indicate that test analog modulation of GABA-gated currents is GABA-A receptor-mediated. To confirm the role of the δ-subunit extrasynaptic GABA-A receptors for enhanced allosteric potentiation of test analogs, neurons from δKO mice were utilized, which lack δ-containing receptors. Test neurosteroid analog-potentiated GABAergic currents (1 μM) were significantly reduced in δKO neurons, which suggest that test neurosteroid analogs have higher sensitivity at neurons that have a high expression of δ-containing GABA-A receptors, possibly driving the allosteric selectivity.

Figure 19A:
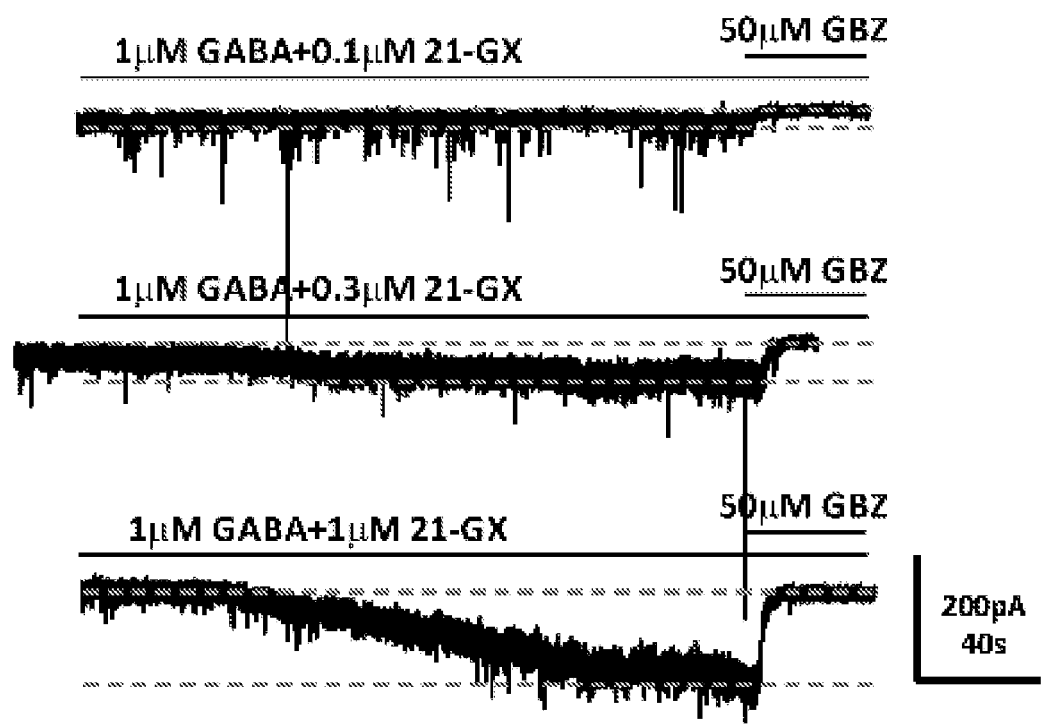
FIGS. 19A-19E. Neurosteroid analogs allosteric potentiation of GABA-A receptor-mediated tonic currents in dentate gyrus granule cells in mouse hippocampus slices. (19A-19C) Representative tonic current recordings from neurons with or without application of test compounds 21-OH-GX, 21-OH-GX-phosphate and 21-OH-GX-lysine. Qualification of tonic current shift was achieved relative to complete block by gabazine (GBZ) application. (19D) Concentration-response curves for allosteric activation of tonic current (pA) by test compounds 21-OH-GX, 21-OH-GX-phosphate and 21-OH-GX-lysine in neurons. (19E) Concentration-response curves for allosteric activation of normalized tonic current density (pA/pF) by test compounds 21-OH-GX, 21-OH-GX-phosphate and 21-OH-GX-lysine in neurons. Each point represents mean±SEM of data from six to ten neurons.
Figure 19B:
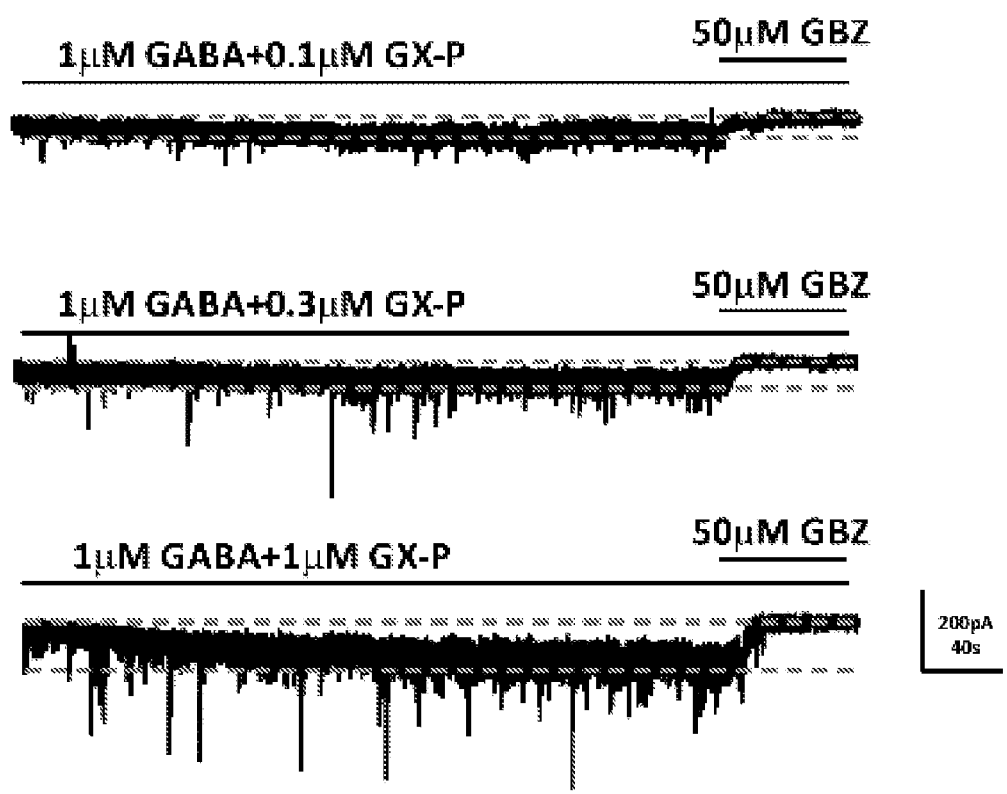
Figure 19C:
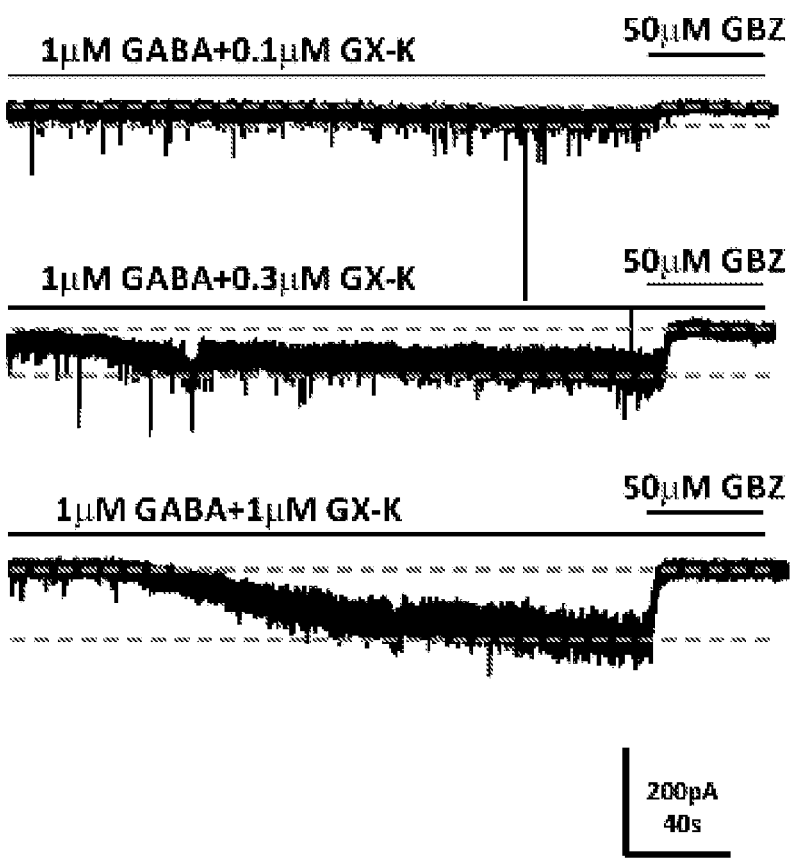
Figure 19D:
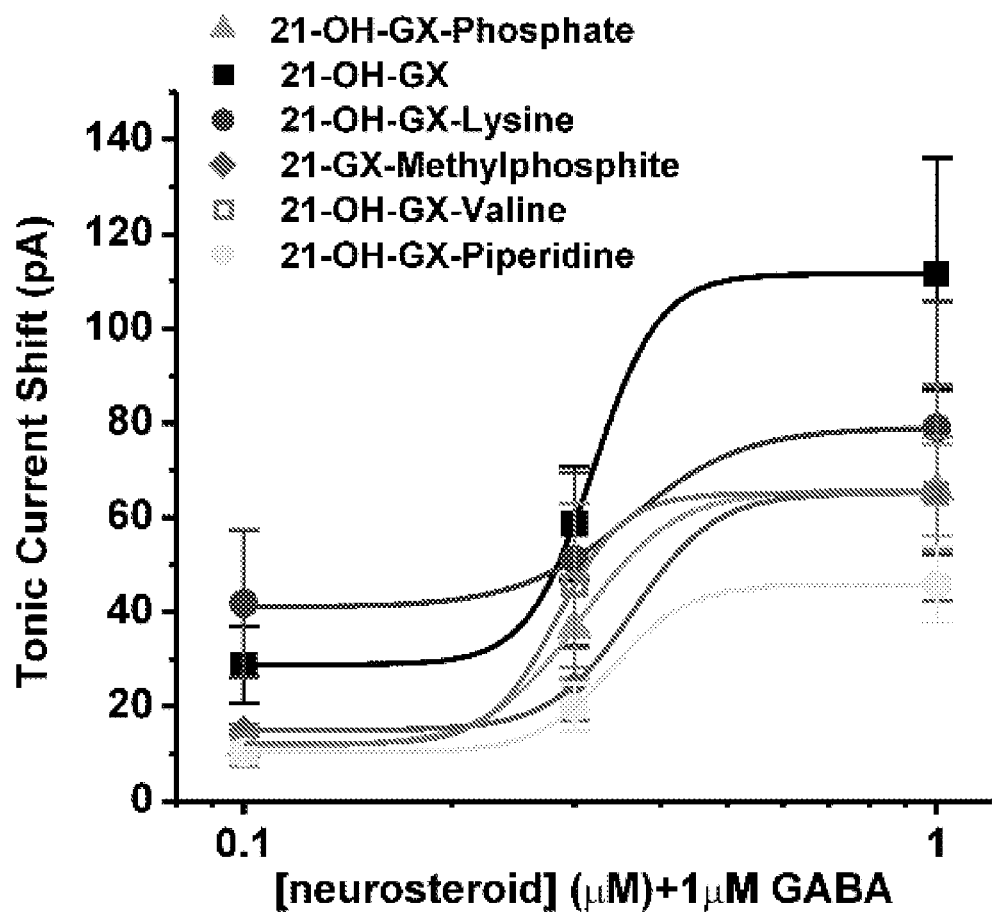
Figure 19E:
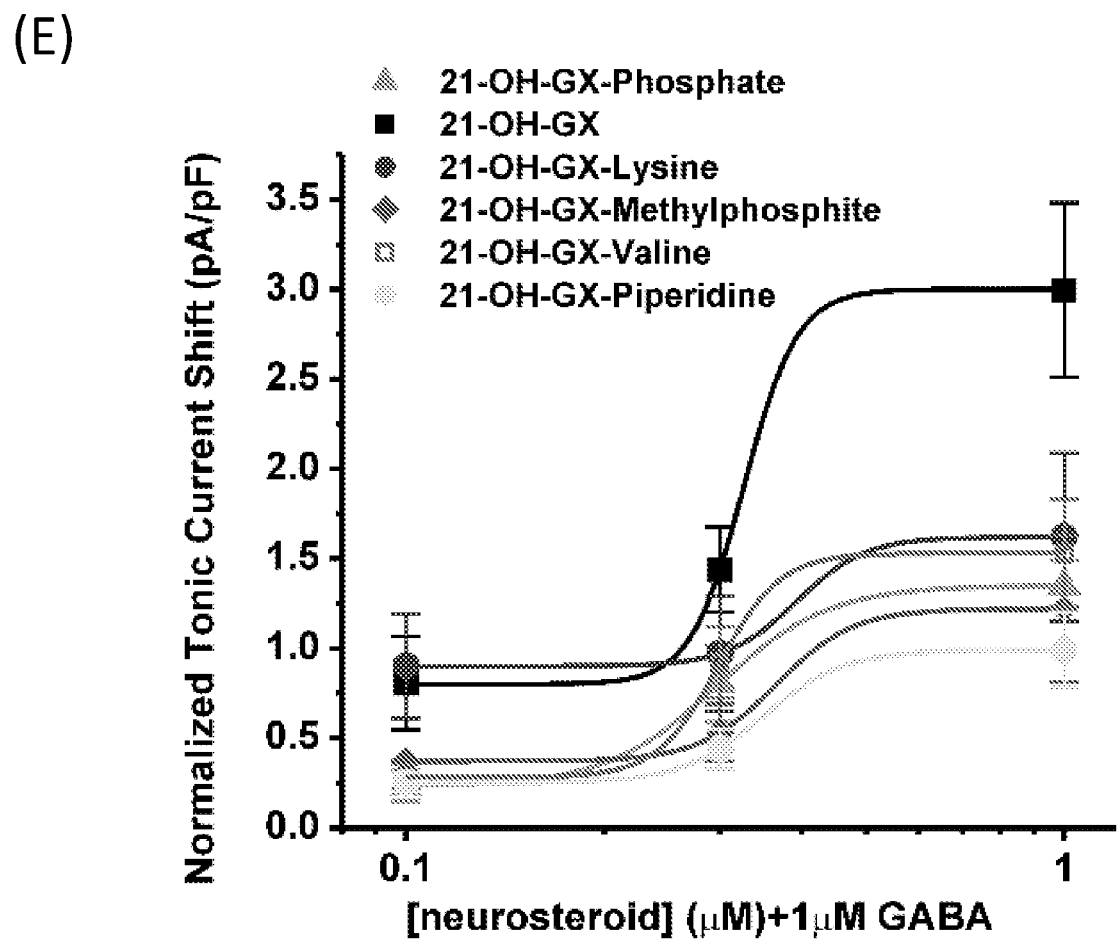

Test compounds were studied for their effect on tonic current in DGGCs in brain slices. Voltage-clamp electrophysiology was used to record enhancement of GABAergic tonic currents by neurosteroid analogs. Baseline tonic currents were derived in a bath perfusion with 1 μM GABA. Test neurosteroid analog was co-applied with 1 μM GABA and at the end of each recording, 50 μM GBZ was perfused in order to determine the total tonic current shift (FIGS. 19A, 19B, and 19C). Tonic current of each cell was normalized to the cell capacitance as a measure of current density (pA/pF). Test neurosteroid analogs produced a concentration-dependent enhancement of tonic current (FIG. 19D) and tonic conductance (FIG. 19E). Test compound potentiation of tonic inhibition was significantly attenuated in DGGCs from δKO mice, indicating their mechanistic selectivity for extrasynaptic δGABA-A receptors.

Figure 20A:
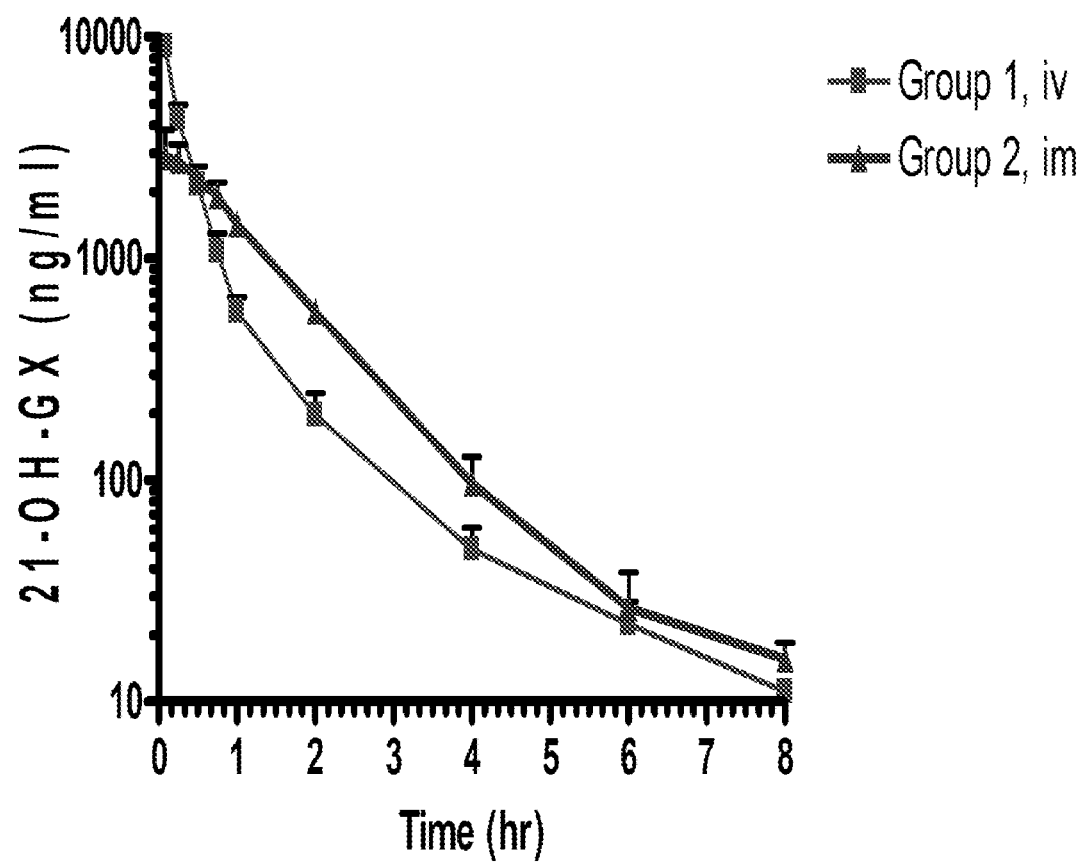
FIG. 20A-20D. Plasma concentrations of 21-OH-GX after intravenous (iv) and intramuscular (im) administration to male Sprague Dawley rats of neurosteroid analogs (20A) 21-OH-GX, (20B) 21-OH-GX phosphate, (20C) 21-OH-GX lysine, and (20D) 21-OH-GX valine.
Figure 20B:
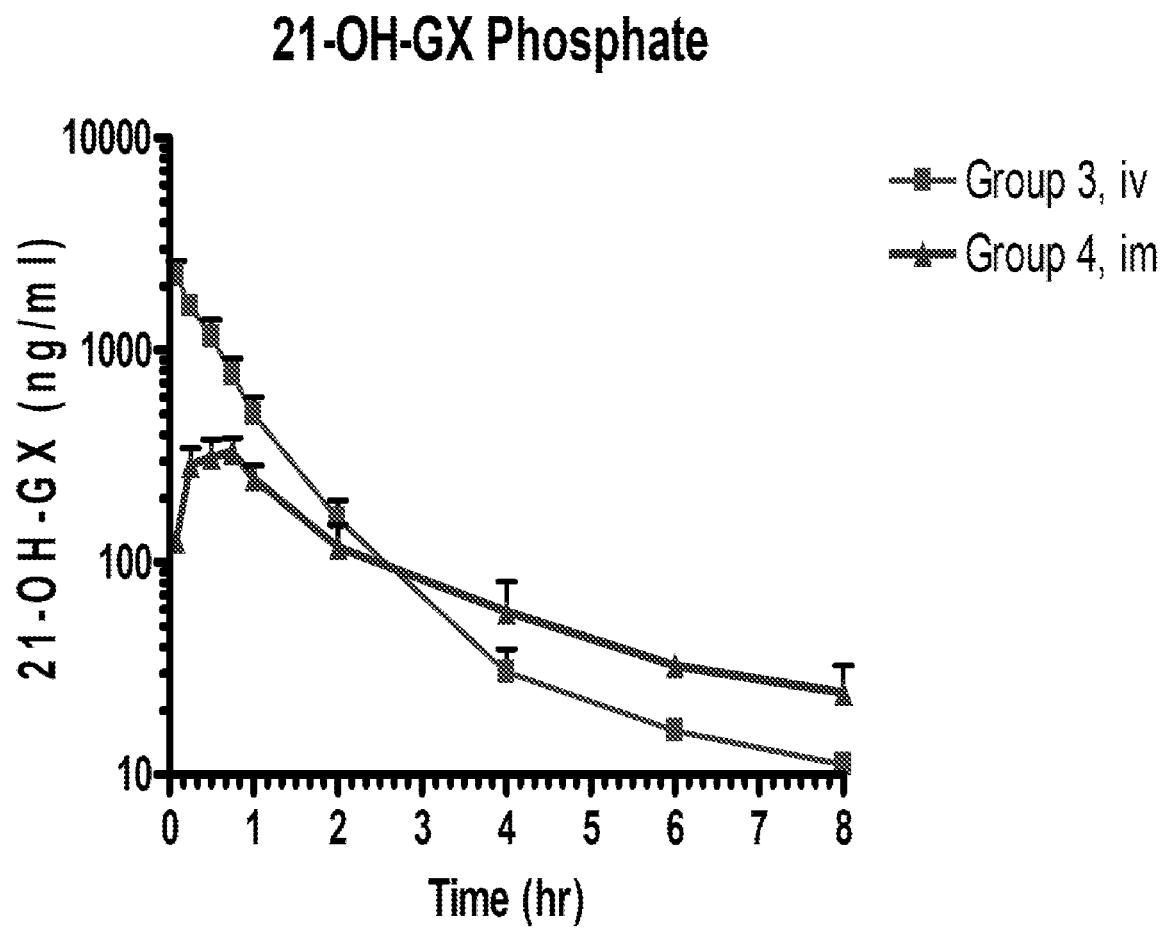
Figure 20C:
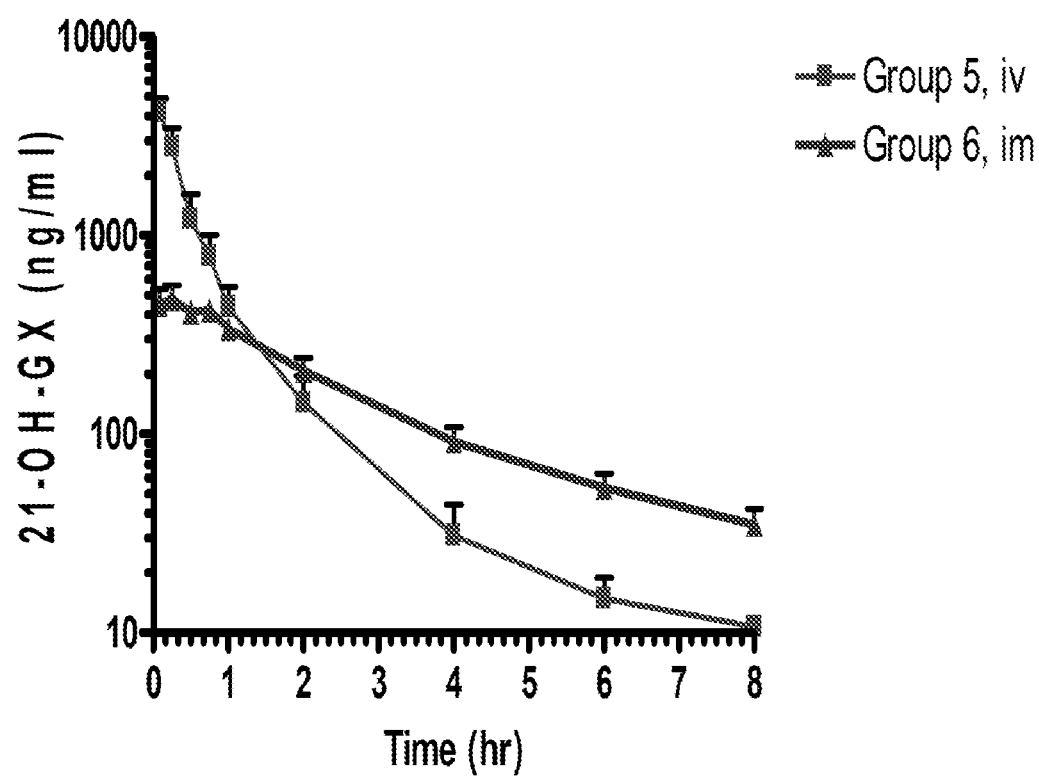
Figure 20D:
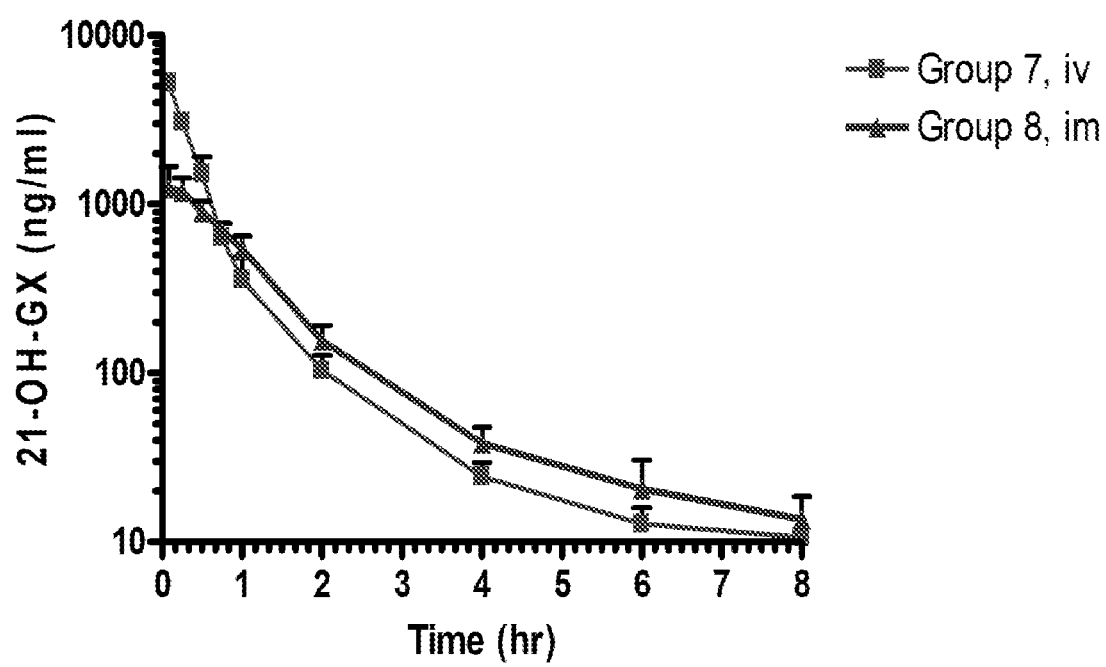

In PK studies, the plasma pharmacokinetics of ganaxolone analogs following an intravenous (iv) or intramuscular (im) dose administration. Male Sprague Dawley rats were administered a single dose of the neurosteroid analog. Rats received a single iv or im dose of 21-OH-GX, 21-OH-GX phosphate, 21-OH-GX lysine, or 21-OH-GX valine at 10 mg/kg. The pharmacokinetic parameters of four ganaxolone analogs were assessed by measuring plasma levels of the active form, 21-OH-GX, which was administered directly or as three different prodrugs by the iv and im routes. The plasma drug concentration versus time profiles for the four neurosteroid analogs were shown in FIG. 20A-20D. The peak plasma level of 21-OH-GX was achieved rapidly after dose administration by the iv route and the highest concentration observed varied depending on the specific test article that was administered. The highest plasma level of 21-OH-GX after iv administration was observed when 21-OH-GX was directly administered (FIG. 20A), followed by 21-OH-GX valine (FIG. 20D) and 21-OH-GX lysine (FIG. 20C). Plasma concentrations of 21-OH-GX after im injection were highest in samples collected at 8 hr in the 21-OH-GX lysine group (FIG. 20C). After iv administration of the four test articles, the Cmax for 21-OH-GX was observed at the first time point blood collection, 0.083 hr, for all four compounds, indicating that the prodrugs (21-OH-GX phosphate, 21-OH-GX lysine, and 21-OH-GX valine) were rapidly converted to 21-OH-GX after injection. In the im groups, the Tmax for 21-OH-GX was observed within 0.65 hr or less. The Cmax values varied as follows for the iv and im groups: 21-OH-GX>21-OH-GX valine>21-OH-GX lysine>21-OH-GX phosphate. The mean bioavailability of 21-OH-GX administered im was about 96%. The relative bioavailability for each of the prodrugs was estimated based on AUCinf of 21-OH-GX derived from the prodrugs compared to AUCinf of 21-OH-GX after direct iv administration. The ganaxolone analogs with the highest im relative bioavailability were 21-OH-GX valine (37%) and 21-OH-GX lysine (31%).

Figure 21A:
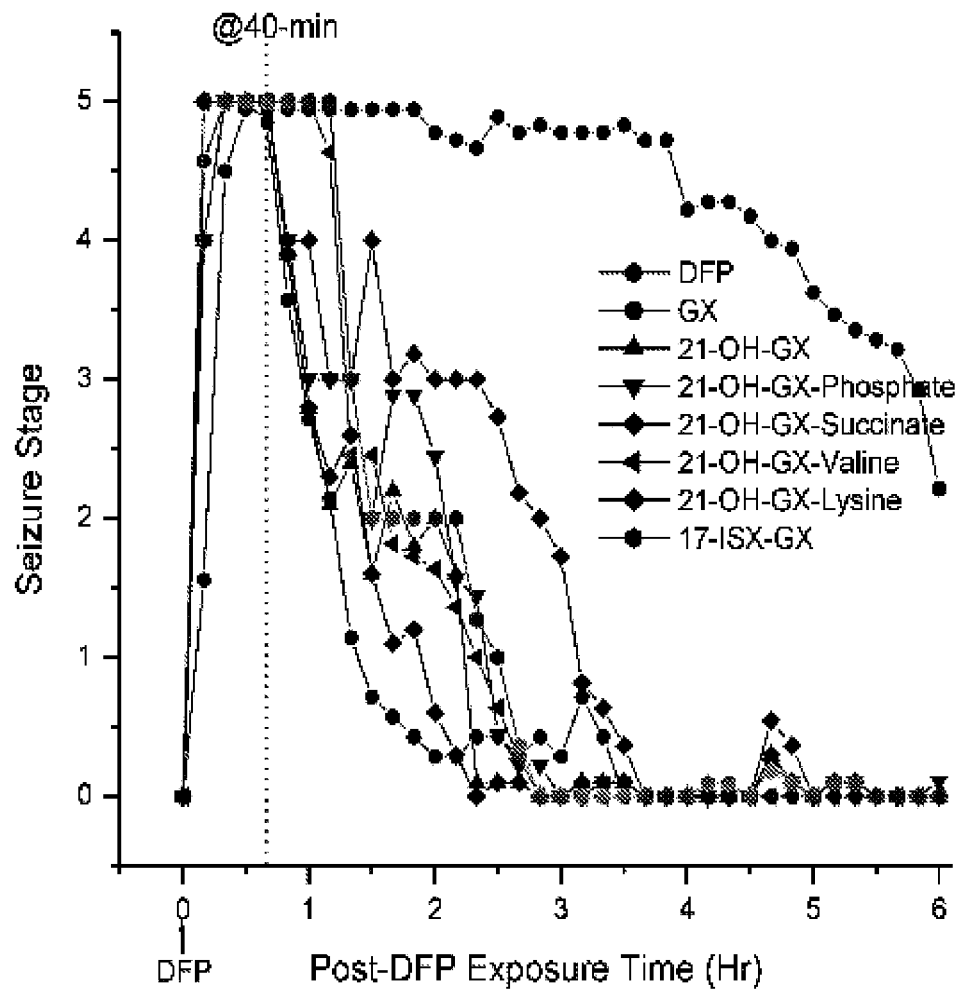
FIG. 21A-21C. Comparative anticonvulsant effect of neurosteroid analogs as compared to the parent ganaxolone on seizure suppression and survival in the DFP model in rats. Test compounds were given intramuscularly (im) 40 min after DFP. Each point or bar represent the mean±SEM of data from 8-12 animals. (21A) Seizure stage, (21B) Seizure Activity, and (21C) Percent Survival.
Figure 21B:
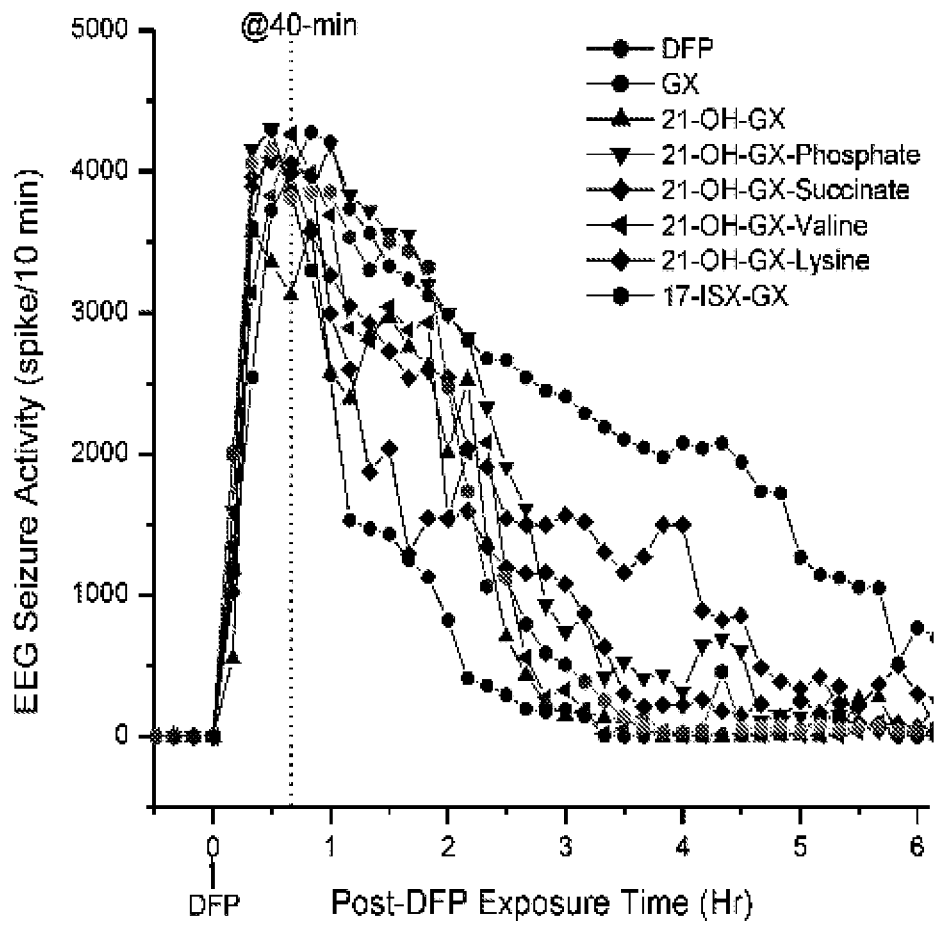
Figure 21C:
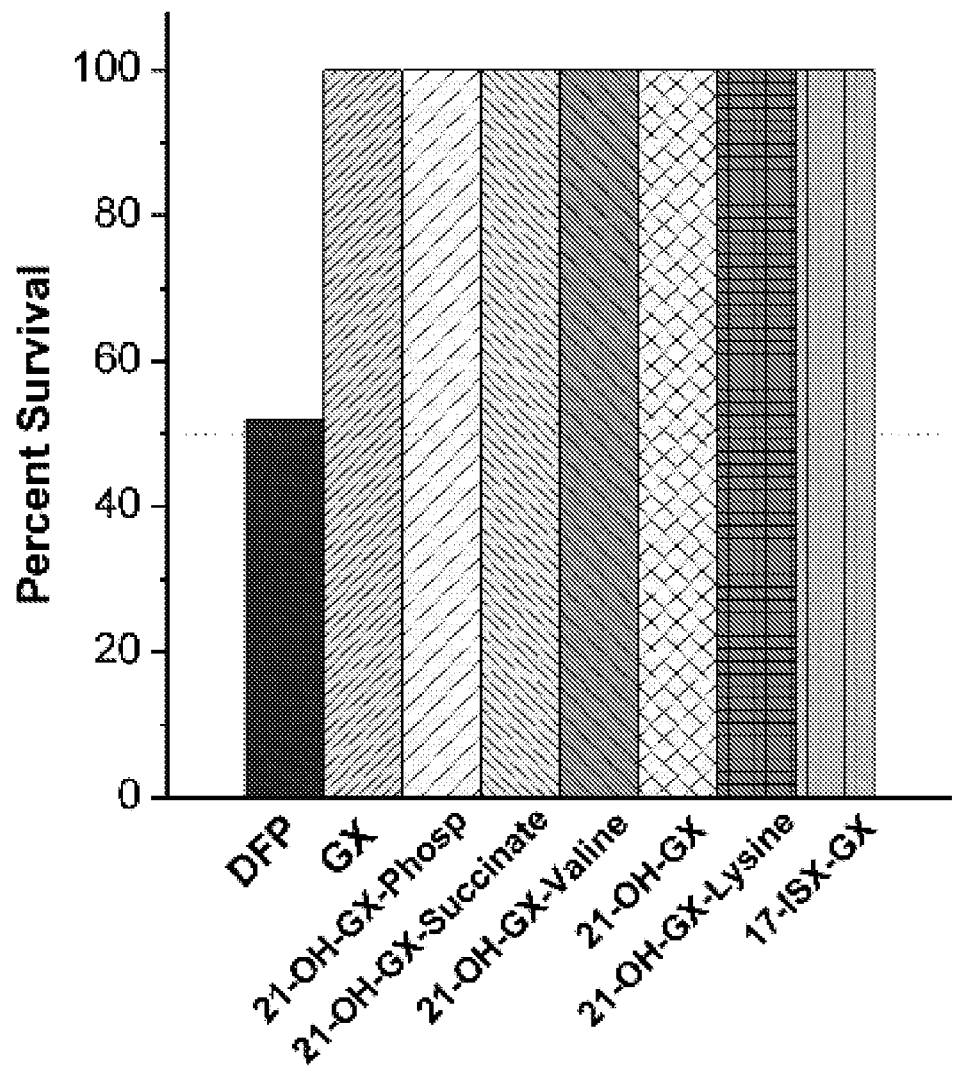

Neurosteroid analogs were tested for the anticonvulsant efficacy in the DFP model in rats. The organophosphate pesticide DFP is widely used as a model of organophosphate intoxication, which causes seizures, status epilepticus (SE) and brain injury. Test compounds were given intramuscularly (im) 40 min after DFP. Test analogs (10 mg/kg, im) produced a striking protection against DFP-induced seizures (FIG. 21A) and EEG seizure activity (FIG. 21B). Untreated animals exhibited 50% mortality; animals that received test analogs at 40-min or later all survived (FIG. 21C), indicating an almost 100% survival rate. Test compounds effectively suppressed seizures, controlled SE, and lethality; this anticonvulsant profile is almost comparable or superior to that of ganaxolone, indicating the neurosteroid analogs anticonvulsant potential for treatment of organophosphate intoxicating and benzodiazepine-resistant SE and brain injury.

Figure 22A:
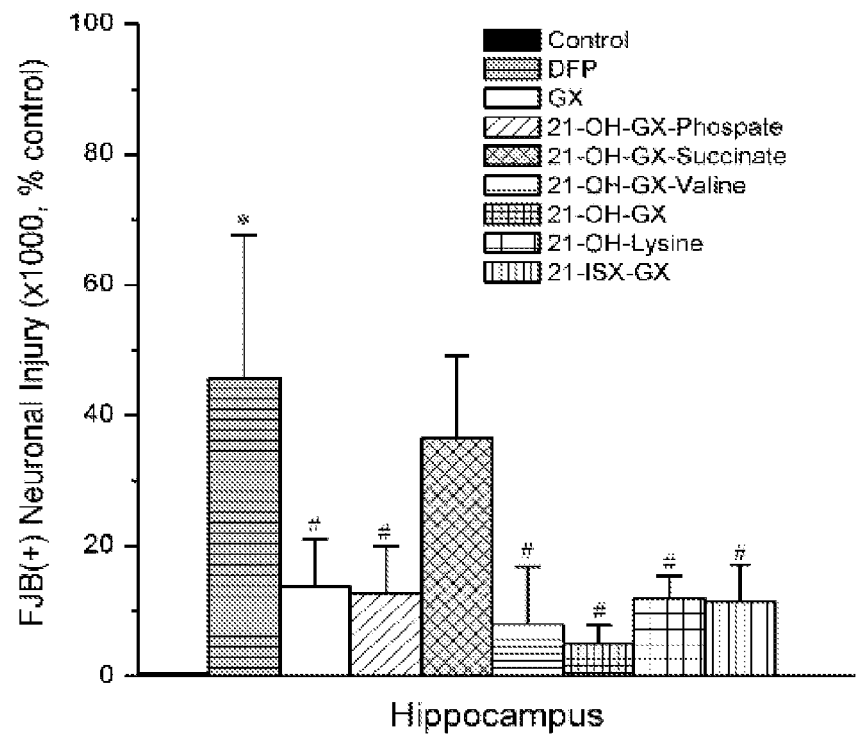
FIG. 22A-22C. Comparative neuroprotective effect of neurosteroid analogs as compared to the parent ganaxolone on neuronal injury and neurodegeneration in the DFP model in rats. Test compounds were given intramuscularly (im) 40 min after DFP. Histopathology was performed at 72 h after DFP exposure. Each point or bar represent the mean±SEM of data from 5-8 animals. *p<0.05 vs control group; #p<0.05 vs DFP group. (22A) Neuronal Injury, (22B) Neuronal Loss, and (22C) Interneuron Loss.
Figure 22B:
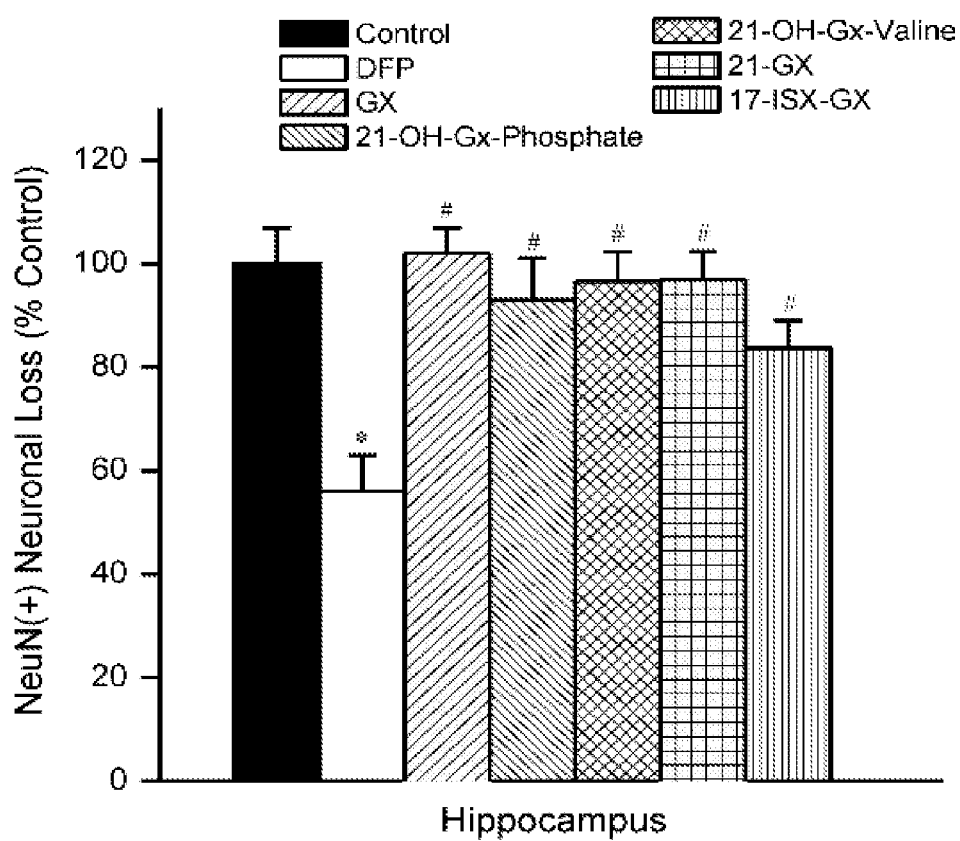
Figure 22C:
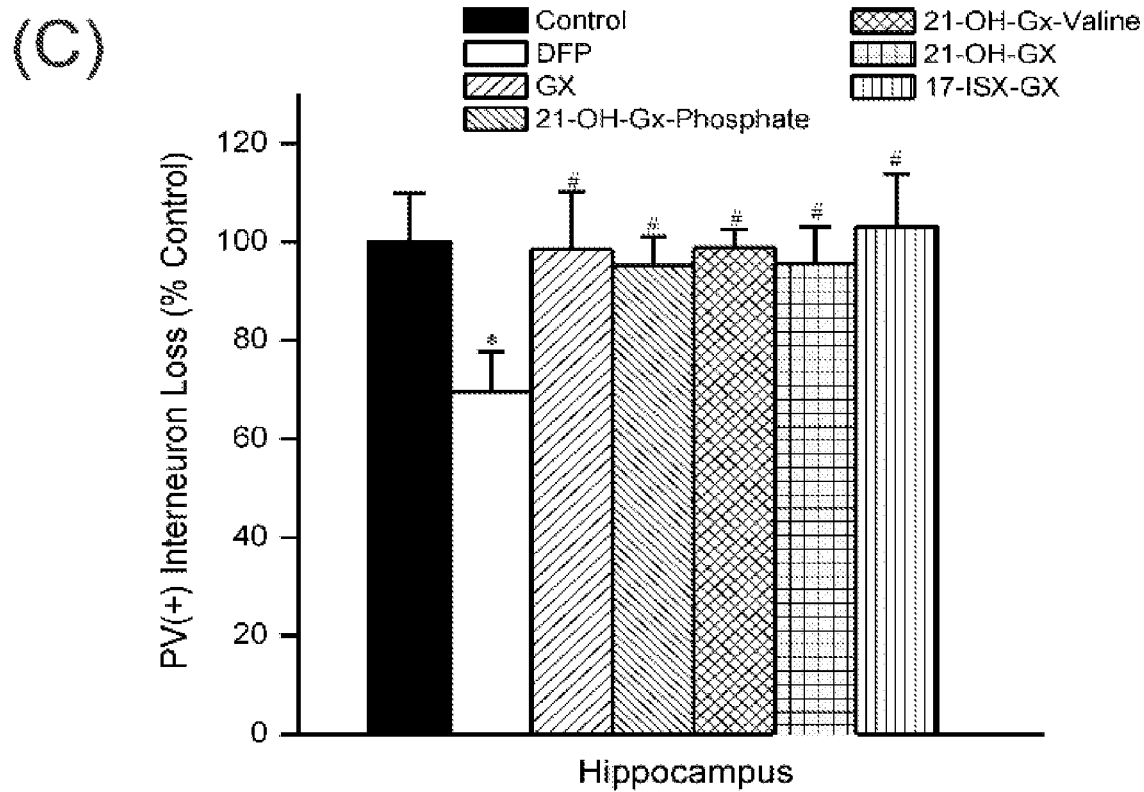

Neurosteroid analogs were tested for neuroprotectant efficacy in the DFP model in rats. Test compounds were given intramuscularly (im) 40 min after DFP. The brains were perfused and processed for histology 72 h after DFP exposure. Neurosteroid compounds significantly reduced neuronal injury assessed by FJB(+) stereology counts in the hippocampus (FIG. 22A). The test analogs elicited significant protection against DFP-induced astrogliosis and inflammation assessed by GFAP(+) immunohistochemistry (FIG. 22B). The test analogs almost completely (95%) prevented the neurodegeneration, loss of NeuN(+) principal neurons (FIG. 22C), and PV(+) interneurons (FIG. 22D) in the DFP model. Test analogs (21-OH-GX-valine; and 21-OH-GX-lysine) exhibited a profile superior to the parent ganaxolone and the standard anticonvulsant midazolam.

Figure 23A:
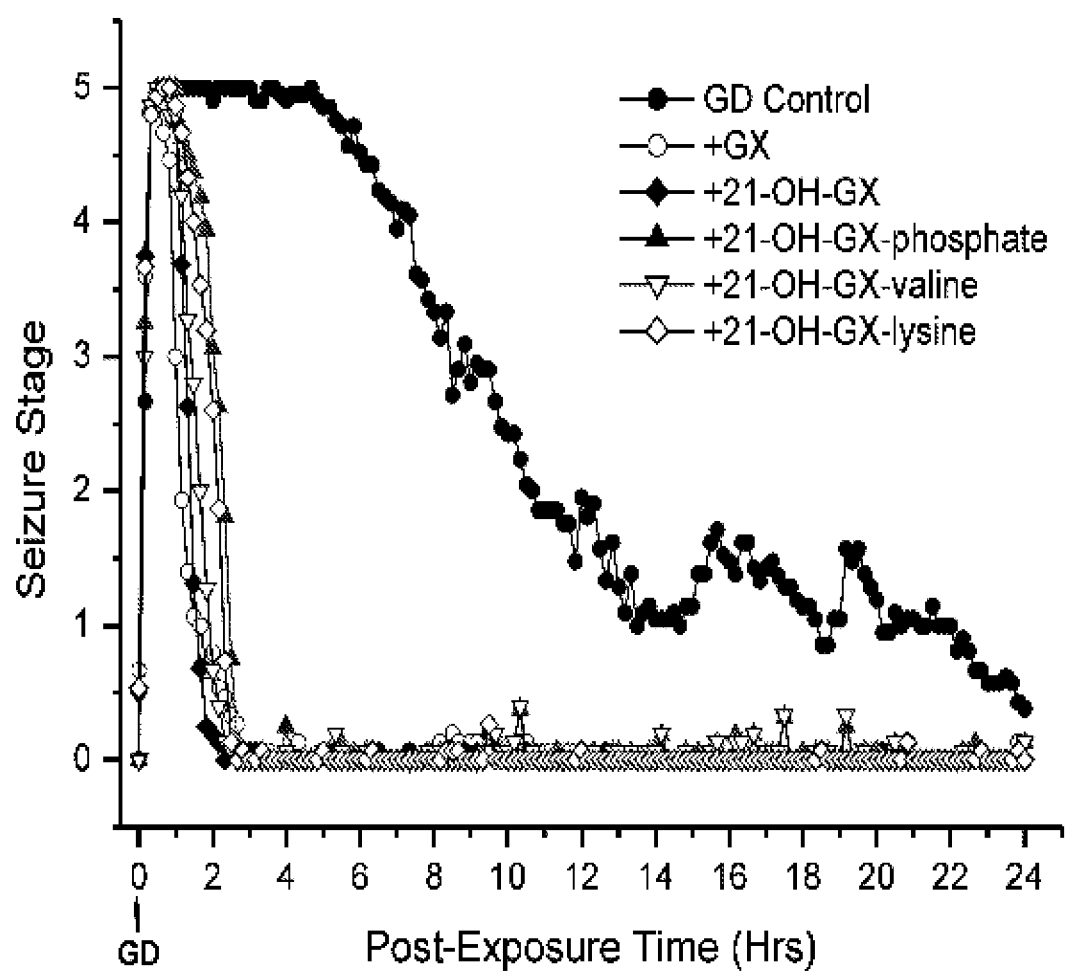
FIG. 23A-23C. Comparative anticonvulsant effect of neurosteroid analogs on seizure suppression and survival in the nerve agent Soman model in rats. Test compounds were given intramuscularly (im) 40 min after soman. Each point or bar represent the mean±SEM of data from 8-12 animals. (23A) Seizure Stage, (23B) Seizure Activity, and (23C) Percent Survival.
Figure 23B:
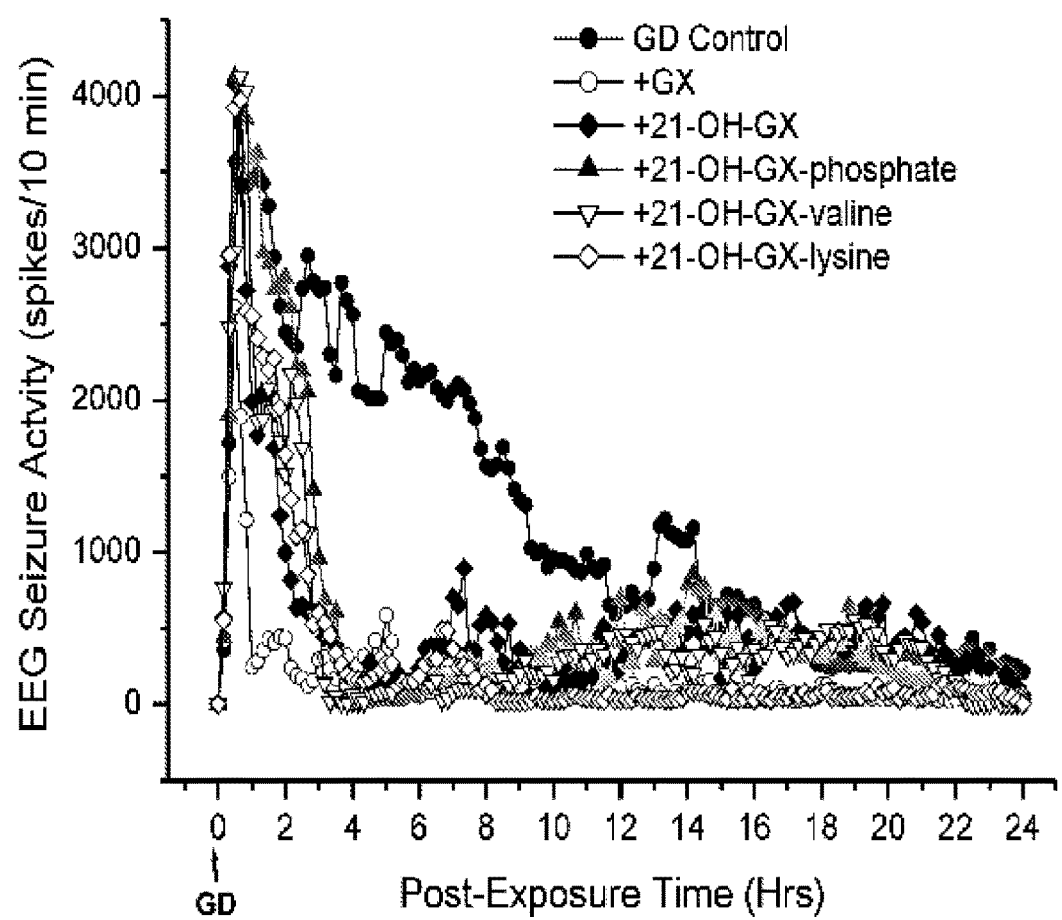
Figure 23C:
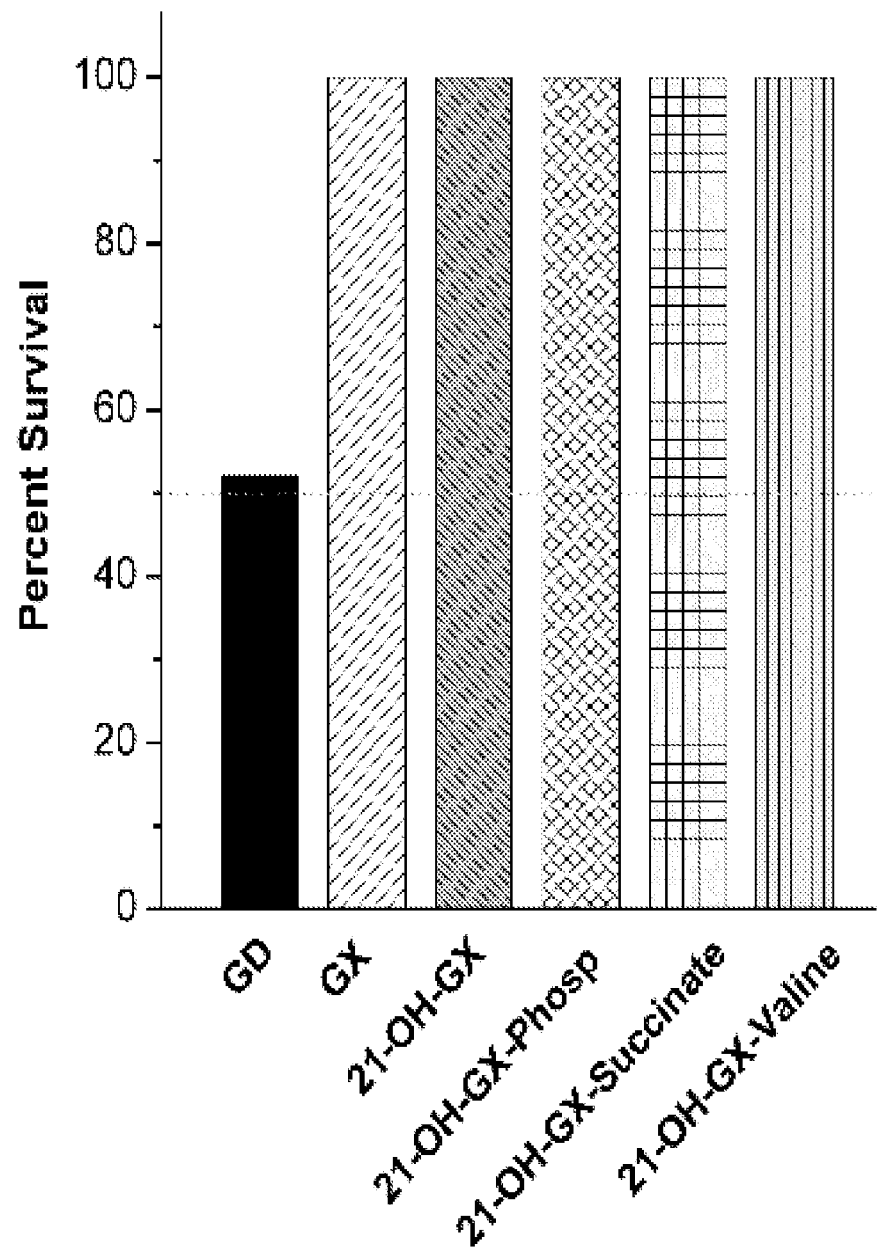

Neurosteroid analogs were tested for anticonvulsant efficacy in the nerve agent soman model in rats. The nerve agent soman causes seizures, status epilepticus (SE) and brain injury. Test compounds were given intramuscularly (im) 40 min after soman exposure. Neurosteroid analogs (10 mg/kg, im) produced a striking protection against soman-induced behavioral seizures (FIG. 23A) and electrographic and SE activity (FIG. 23B). Three of four analogs (21-OH-GX, 21-OH-GX-valine and 21-OH-GX-lysine) effectively terminated SE when given 40-min after soman, indicating their efficacy in the GD model. Untreated animals exhibited 50% mortality following soman and animals that received test analogs at 40-min or later all survived (FIG. 23C), indicating ~100% survival rate.

Figure 24A:
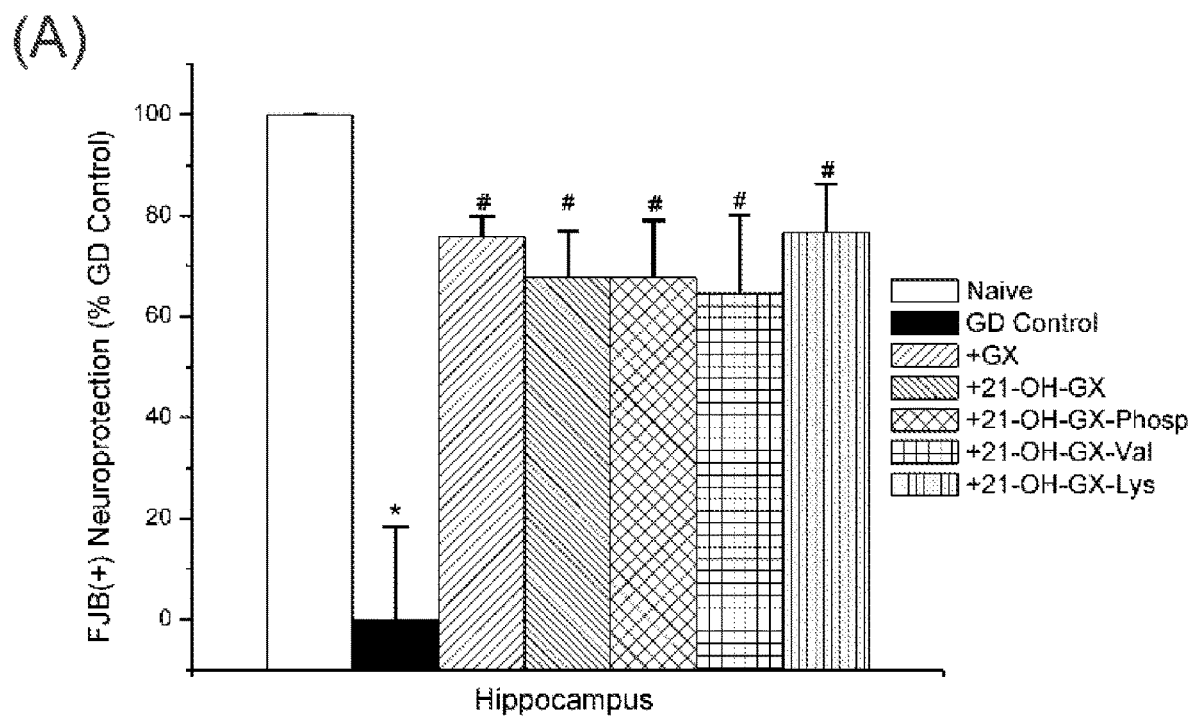
FIG. 24A-24D. Comparative neuroprotective effect of neurosteroid analogs on neuronal injury, neuroinflammation, and neurodegeneration in the nerve agent Soman model in rats. Test compounds were given intramuscularly (im) 40 min after DFP. Histopathology was performed at 24 h after soman exposure. Each point or bar represent the mean±SEM of data from 5-8 animals. *p<0.05 vs control group; #p<0.05 vs Soman group. (24A) Neuroprotection, (24B) Neuroinflammation, (24C) Neuronal Loss, and (24D) Interneuron Loss.
Figure 24B:
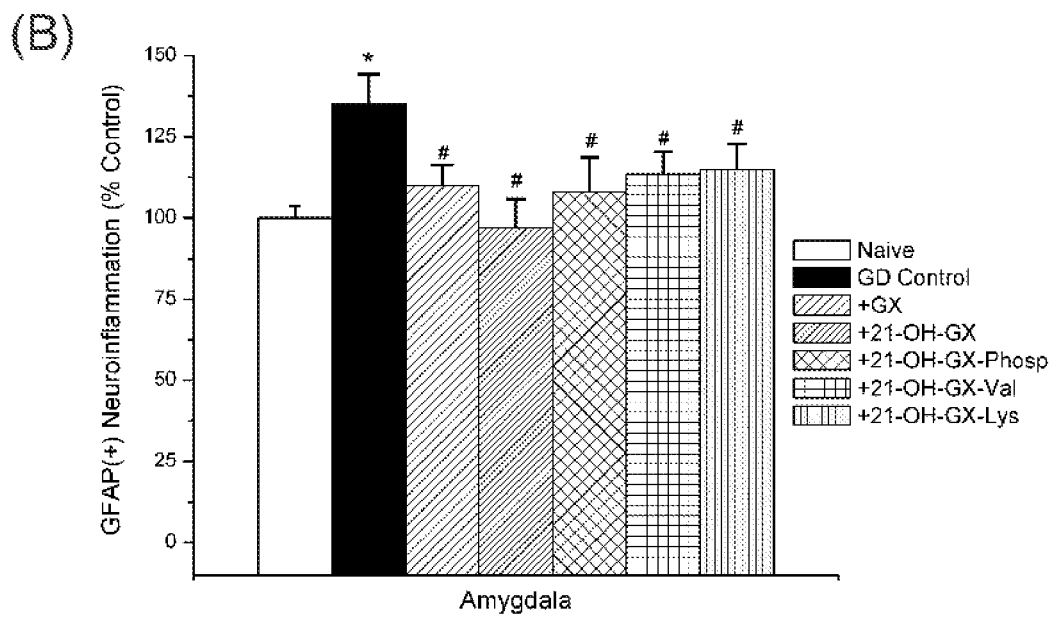
Figure 24C:
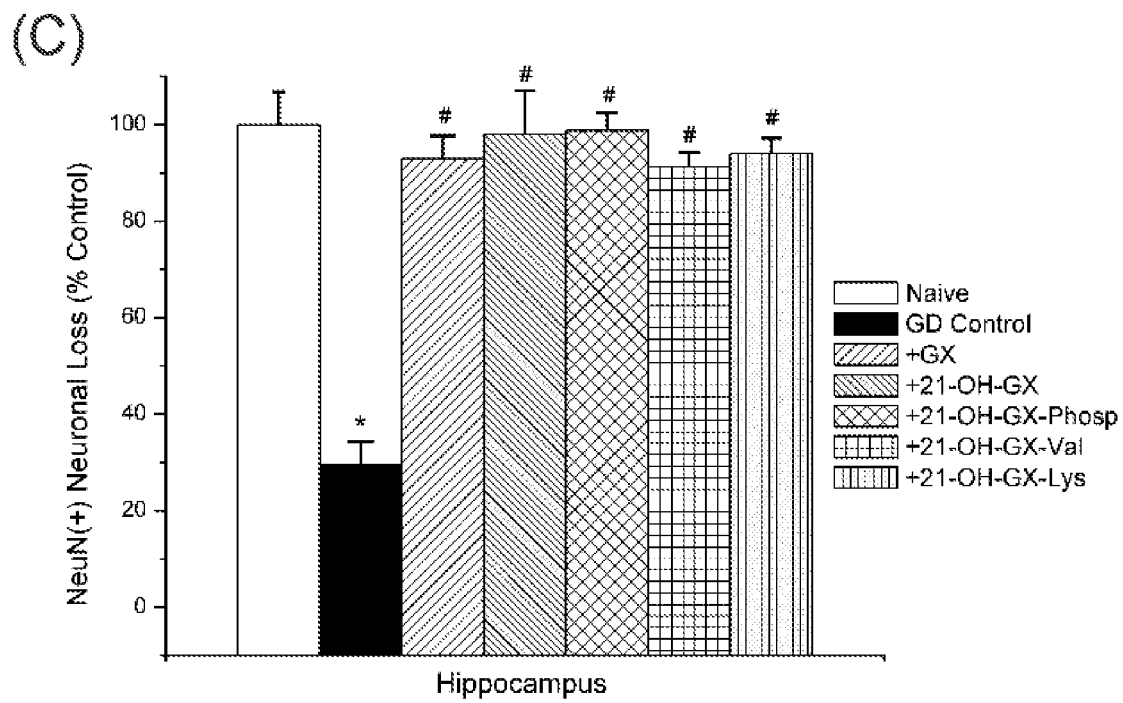
Figure 24D:
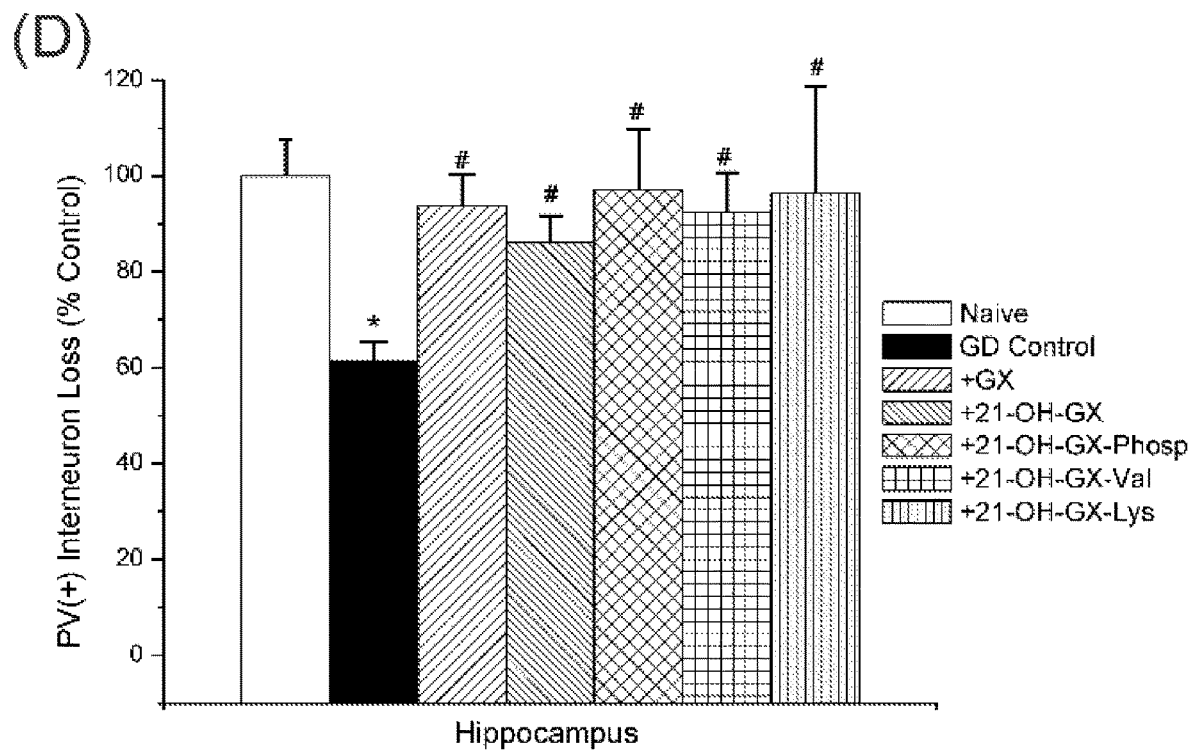

Neurosteroid analogs were tested for neuroprotectant efficacy in the nerve agent soman model in rats. Test compounds were given intramuscularly (im) 40 min after soman. The brains were perfused and processed for histology 24 h after soman exposure. In untreated control group, soman caused extensive neuronal injury in the hippocampus and other brain regions as revealed by FJB staining. Neurosteroid analogs significantly reduced neuronal injury assessed by FJB(+) stereology counts in the hippocampus (FIG. 24A). They produced significant protection against soman-induced neuroinflammation as assessed by GFAP(+) immunostaining in the amygdala (FIG. 24B). These analogs almost completely prevented the loss of NeuN(+) principal neurons (FIG. 24C) and PV(+) interneurons (FIG. 24D) in the hippocampus as assessed by immunostaining and unbiased stereology quantification. These studies confirm the anticonvulsant and neuroprotectant efficacy of the neurosteroid analogs, indicating their potential for treatment of nerve agent exposure and benzodiazepine-resistant SE and brain injury.

Many of the neurosteroid derivatives of ganaxolone described herein are active with powerful protective activity in multiple seizure models. The neurosteroid derivatives produced a rapid and dose-dependent suppression of behavioral and electrographic seizures, with nearly complete seizure protection within 15-min after administration. The anticonvulsant ED50 doses were comparable to that of ganaxolone. Since ganaxolone is highly effective in organophosphate (OP) models, these neurosteroid derivatives were determined to be similarly active in the DFP and Sarin model. Thus, these compounds are clinically useful for epilepsy, chemical neurotoxicity and other brain disorders.

While the preferred embodiment of the disclosure has been illustrated and described, it will be appreciated that various changes can be made therein without departing from the spirit and scope of the disclosure.

Example 2. Methods for Making Neurosteroid Derivatives $^1$H NMR was recorded on a Varian Utility 300 or 400 MHz spectrometer, in deuterated chloroform (CDCl$_3$) or dimethylsulfoxide (DMSO-d$_6$) solvent. Chemical shifts were reported as ppm from solvent reference. Coupling constants (J values) were measured in hertz. Low resolution electrospray mass spectra (ES-MS) were collected on a Finnigan liquid chromatography quadrupole (LCQ) Duo liquid chromatography tandem mass spectrometer (LC-MS-MS) (Thermoquest). Crude products were purified by column chromatography and recrystallization. Purity was assessed by HPLC and $^1$H NMR. HPLC method used a reverse phase XBridge C18 5 m 4.6×250 mm column from Waters running a binary gradient with water (with 0.1% TFA) and acetonitrile (with 0.1% TFA). Peaks were detected using the wavelength MAX reading from a photodiode array detector scanning from 200-600 nm on a 20 min gradient running from 10% to 95% acetonitrile/TFA in H$_2$O/TFA at 1 mL/min on a Waters Alliance HPLC.

In one aspect, the present disclosure provides methods for making neurosteroid derivatives.

In an embodiment, the disclosure provides a method for using pregnenolone to make 21-OH ganaxolone and other intermediary compounds which are useful for preparing neurosteroid derivatives. The method of making 21-OH ganaxolone is shown below in Route 1.

Route 1

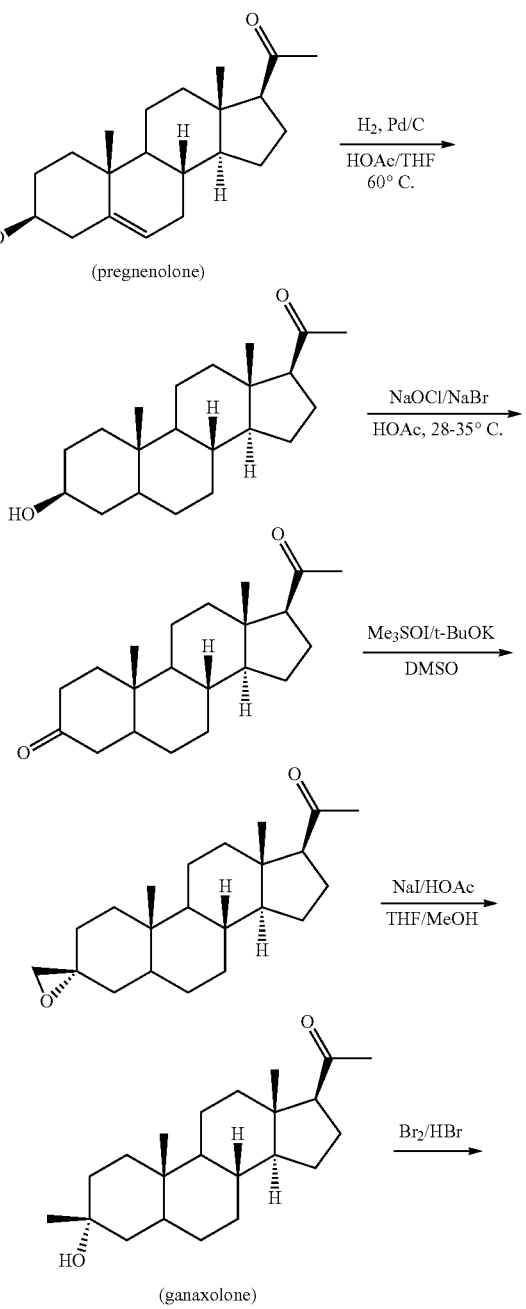

-continued

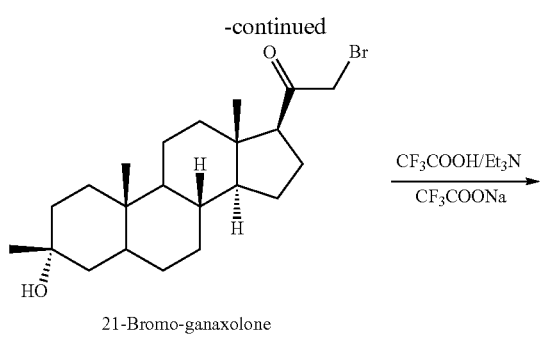

21-Bromo-ganaxolone

CF₃COOH/Et₃N / CF₃COONa →

21-Hydroxy-ganaxolone

Referring to Route 1, Synthesis of 1-((3S,8R,10S, 13S,14S,17S)-3-hydroxy-10,13-dimethylhexadecahydro-1H-cyclopenta[a]phenanthren-17-yl)ethenone

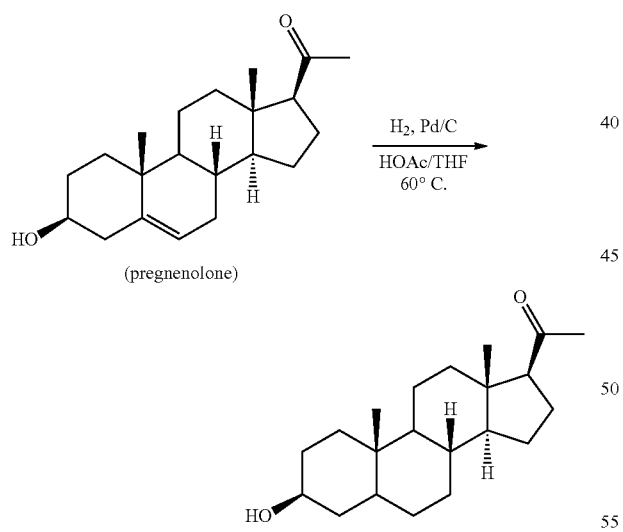

(pregnenolone)

H₂, Pd/C / HOAc/THF 60° C. →

Pregnenolone (3.17 g, 10 mmol) was dissolved in 30 mL of THF and 5 mL of acetic acid. To it, 10% Pd/C (0.3 g) was added. The resulting mixture was shaken under 60 psi hydrogen at 60° C. overnight. It was filtered through a CELITE® pad and concentrated to give 3.2 g of the desired product (100%). ¹H NMR (400 MHz, CDCl3) δ 3.58 (tt, J=11.0, 4.8 Hz, 1H), 2.50 (t, J=9.0 Hz, 1H), 2.19-2.11 (m, 2H), 2.09 (s, 3H), 2.06-1.93 (m, 2H), 1.85-1.75 (m, 1H), 1.74-1.50 (m, 6H), 1.47-1.04 (m, 9H), 1.04-0.82 (m, 2H), 0.79 (s, 3H), 0.72-0.61 (m, 1H), 0.58 (d, J=2.4 Hz, 3H).

Synthesis of (8R,10S,13S,14S,17S)-17-acetyl-10,13-dimethyltetradecahydro-1H-cyclopenta[a]phenanthren-3(2H)-one

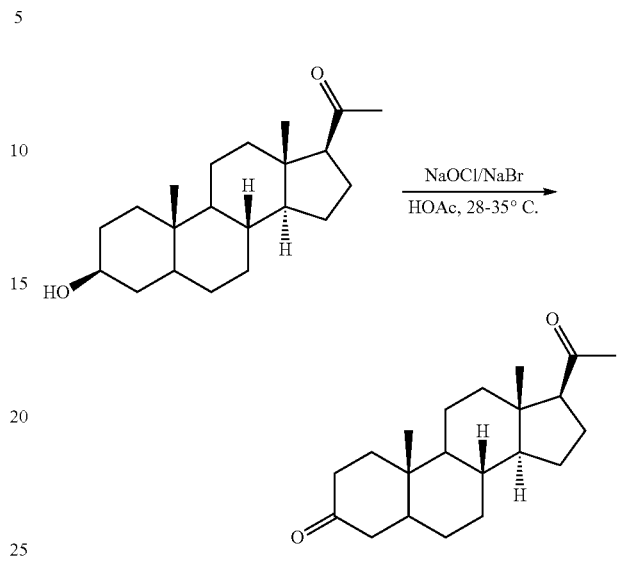

NaOCl/NaBr / HOAc, 28-35° C. →

To a solution of the above product (1-((3S,8R,10S,13S,14S,17S)-3-hydroxy-10,13-dimethylhexadecahydro-1H-cyclopenta[a]phenanthren-17-yl)ethanone, 3.2 g, 10 mmol) in 40 mL of THF and 10 mL of acetic acid was added NaBr (1.03 g, 0.1 eq.). It was cooled in an ice bath and was followed by the dropwise addition of NaOCl (82 mL, 10-15%, 18 eq.) at such a rate that the internal temperature was maintained <40° C. After addition, it was stirred at room temperature for 2 h. Thin layer chromatography (TLC) indicated it was complete. The mixture was diluted with dichloromethane and layers were separated. The organic layer was washed with Na₂S₂O₃ (10% aq.), H₂O, NaHCO₃ (sat.) and NaCl (sat.). Drying over Na₂SO₄ and concentration afforded 3.8 g of the crude product, which was recrystallized from CH₂Cl₂/Hex to give 2.57 g of the desired product (81%). ¹H NMR (400 MHz, CDCl3): 2.51 (t, 1H), 2.2-2.4 (m, 3H), 2.1-2.2 (m, 1H), 2.10 (s, 3H), 1.98-2.01 (m, 2H), 1.6-1.7 (m, 4H), 1.55-1.6 (m, 1H), 1.3-1.4 (m, 7H), 1.1-1.2 (m, 2H), 0.99 (s, 3H), 0.95-0.98 (m, 1H), 0.75-0.78 (m, 1H), 0.62 (s, 3H).

Synthesis of 1-((2'R,8R,10S,13S,14S,17S)-10,13-dimethylhexadecahydrospiro[cyclopenta[a]phenanthrene-3,2'-oxiran]-17-yl)ethanone

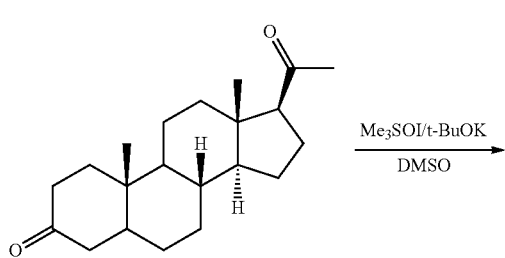

Me₃SOI/t-BuOK / DMSO →

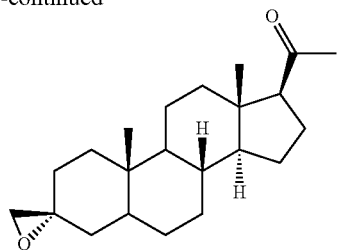

Under argon, trimethylsulfoxonium iodide (2.6 g, 1.7 eq.) and sodium t-butoxide (1.18 g, 1.75 eq.) in DMSO (20 mL) was heated at 65° C. for 2 h. After it was cooled to RT, the above di-ketone ((8R,10S,13S,14S,17S)-17-acetyl-10,13-dimethyltetradecahydro-1H-cyclopenta[a]phenanthren-3(2H)-one, 2.2 g, 7 mmol) was added scoop-wise so that the internal temperature was maintained between 25-35° C. The resulting mixture was stirred at RT for 2 h. After TLC indicated it was complete, it was quenched with 30 mL of $H_2O$, stirred for 10 min and was kept in fridge overnight. The precipitate was filtered, washed with 20 mL of (4:1 of $H_2O$/MeOH), dried to give 94% of the desired product (W=2.17 g). $^1$H NMR (400 MHz, CDCl3) δ 2.63 (s, 2H), 2.53 (t, J=8.9 Hz, 1H), 2.20-2.13 (m, 1H), 2.11 (s, 3H), 2.10-1.95 (m, 2H), 1.87 (dd, J=13.9, 13.1 Hz, 1H), 1.76-1.59 (m, 4H), 1.58-1.48 (m, 1H), 1.48-1.24 (m, 5H), 1.24-1.07 (m, 3H), 1.02-0.87 (m, 2H), 0.86 (dd, J=3.7, 2.2 Hz, 1H), 0.84 (s, 3H), 0.81-0.74 (m, 1H), 0.61 (s, 3H).

Synthesis of 1-((3R,8R,10S,13S,14S,17S)-3-hydroxy-3,10,13-trimethylhexadecahydro-1H-cyclopenta[a]phenanthren-17-yl)ethanone (ganaxolone)

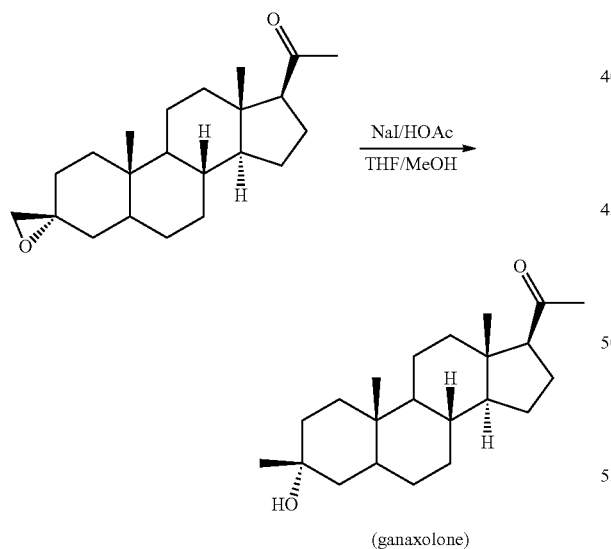

To a solution of the above epoxide (1.5 g, 4.56 mmol) in 15 mL of THF and 15 mL of MeOH were added NaI (1.02 g, 1.5 eq.) and HOAc (0.6 mL, 2.2 eq.). The resulting mixture was heated at 65° C. for 2 h. After TLC indicated that the epoxide was completely converted to an iodo compound, it was cooled to RT. Sodium acetate (1.02 g, 2.7 eq.) and 150 mg of 10% Pd/C were added and the mixture was transferred to a hydrogenation bottle with the aid of MeOH (10 mL) and was hydrogenated under 50 psi hydrogen over the weekend. It was filtered through CELITE® and the filtrate was concentrated. The residue was then partitioned between dichloromethane and water. The aqueous solution was extracted twice with $CH_2Cl_2$ and the combined organic layers were washed with brine, dried over $Na_2SO_4$ and concentrated. The Biotage flash purification with 10-35% EtOAc in hexane to give 0.5 g of the desired product (33%).

The synthesis was repeated with 1.1 g of the epoxide and 1 g of the product was obtained (90%).

Both lots of product were combined and recrystallized with $CH_2Cl_2$ and hexane to give 0.522 g of the product with 96.6% purity by HPLC. $^1$H NMR (400 MHz, Chloroform-d) δ 2.51 (t, J=8.9 Hz, 1H), 2.18-2.10 (m, 1H), 2.09 (s, 3H), 2.01-1.93 (m, 1H), 1.72-1.57 (m, 4H), 1.57-1.41 (m, 5H), 1.41-1.30 (m, 3H), 1.30-1.20 (m, 3H), 1.18 (s, 3H), 1.17-1.09 (m, 2H), 1.00-0.85 (m, 1H), 0.78 (ddd, J=10.6, 7.7, 5.4 Hz, 1H), 0.73 (d, J=0.6 Hz, 3H), 0.58 (s, 3H). UV: Absorbances at 206.2 nm. TLC: (Silica Gel plates) 20% EtOAc/Hexane; Rf=0.50. HPLC: Sunfire C18 5µ 250×4.6 mm; flow 1.0 mL/min; Waters 996 PDA detection at 210 nm; solvent 80% Acetonitrile in $H_2O$ (0.1% formic acid) over 30 min; retention time 8.24 min; 96.6%.

Synthesis of 2-bromo-1-((3R,8R,10S,13S,14S,17S)-3-hydroxy-3,10,13-trimethylhexadecahydro-1H-cyclopenta[a]phenanthren-17-yl)ethan-1-one (21-Bromo-ganaxolone)

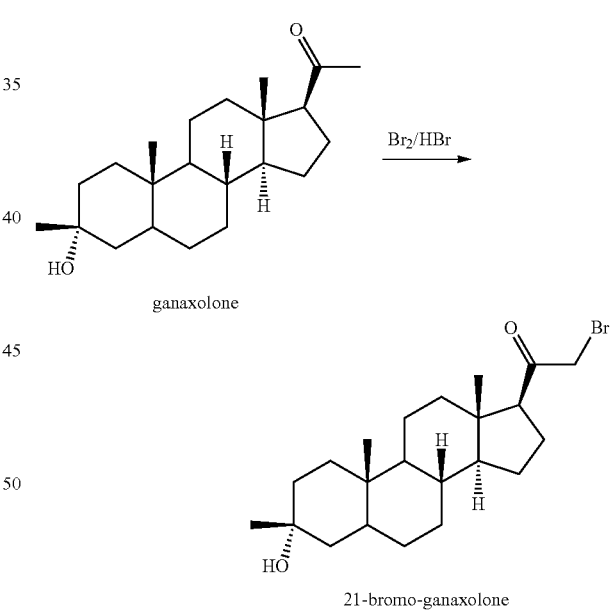

To a solution of ganaxolone (0.33 g, 1 mmol) in 20 mL of methanol were added 2 drops of HBr (48% in $H_2O$) and 0.13 mL of bromine (2.5 eq.) dropwise. The resulting mixture was stirred at RT for 1.25 h, during which precipitate formed. TLC indicated the complete consumption of the starting material. The mixture was poured into icy water and the product was extracted with dichloromethane. The organic layer was washed with $Na_2S_2O_3$ (10% aqueous solution), $H_2O$, NaCl (saturated) and dried ($Na_2SO_4$). Evaporation of solvents gave 0.4 g of the desired product (100% yield). $^1$H NMR (400 Hz, CDCl3): δ 3.89 (d, J=3.0

Hz, 2H), 2.80 (t, J=8.9 Hz, 1H), 2.21-2.10 (m, 1H), 1.89 (dt, J=11.8, 3.4 Hz, 1H), 1.79-1.58 (m, 4H), 1.57-1.43 (m, 5H), 1.42-1.30 (m, 2H), 1.30-1.20 (m, 4H), 1.18 (s, 3H), 1.16-1.11 (m, 2H), 0.94 (qd, J=12.2, 5.6 Hz, 1H), 0.78 (ddd, J=12.9, 10.6, 4.5 Hz, 1H), 0.73 (s, 3H), 0.61 (s, 3H).

Synthesis of 2-hydroxy-1-((3R,8R,10S,13S,14S, 17S)-3-hydroxy-3,10,13-trimethylhexadecahydro-1H-cyclopenta[a]phenanthren-17-yl)ethan-1-one (21-OH-ganaxolone)

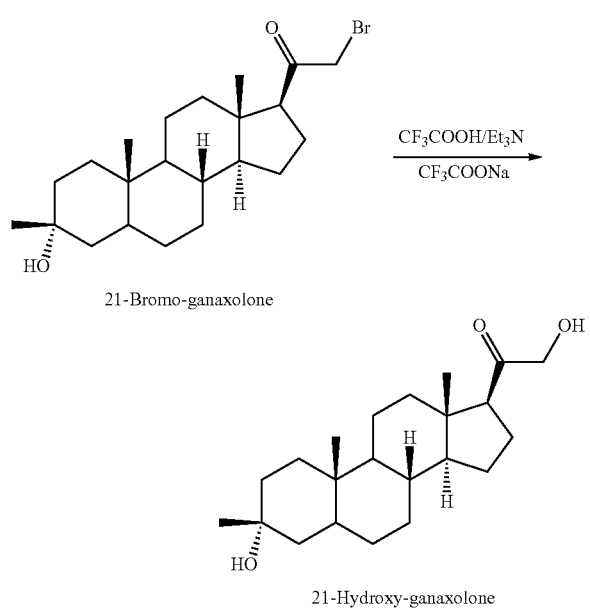

To a solution of trimethylamine (13.2 mL, 95 mmol, 13 eq.) in 180 mL of acetone at 0° C. was added trifluoroacetic acid (5.4 mL, 73 mmol, 10 eq.). The mixture was stirred at RT after the addition for 10 min. To this mixture was then added 21-bromo-ganaxolone (3.0 g, 7.3 mmol). After the resulting mixture was heated in 65° C. oil bath for 1 hour, CF$_3$COONa (15 eq. 109 mmol, 14.9 g) was added. The mixture was heated at 65° C. overnight. It was cooled to RT and was concentrated. The residue was partitioned between dichloromethane and water. The aqueous layer was extracted with DCM. The combined organic layers were washed with brine and dried over MgSO$_4$. The product was purified on a Biotage column with 5-80% EtOAc in hexane to give 2.09 g of the desired product (82% yield). $^1$H NMR (400 MHz, DMSO-d6) δ 4.87 (dd, J=5.9, 0.7 Hz, 1H), 4.01 (d, J=5.9 Hz, 2H), 3.83 (s, 1H), 2.55 (t, J=8.8 Hz, 1H), 2.00 (dd, J=21.0, 10.3 Hz, 1H), 1.80 (d, J=12.5 Hz, 1H), 1.66-1.42 (m, 6H), 1.39-1.24 (m, 4H), 1.24-1.07 (m, 9H), 1.04 (s, 3H), 0.97-0.78 (m, 1H), 0.67 (s, 3H), 0.50 (s, 3H). UV: 201, 280 nM. TLC: (Silica Gel plates) 20% EtOAc/Hexane; Rf=0.25. HPLC: Sunfire C18 5 250×4.6 mm; flow 1.0 mL/min; Waters 996 PDA detection at 210 nm; solvent 50% Acetonitrile in H$_2$O (0.1% TFA) over 30 min; retention time 14.36 min; 98.84%.

In another embodiment, the disclosure provides a method for using 21-Bromo ganaxolone to make 21-OH Ganaxolone Valine. The method of making 21-OH Ganaxolone Valine from 21-Bromo Ganaxolone is shown below in Route 2.

Route 2

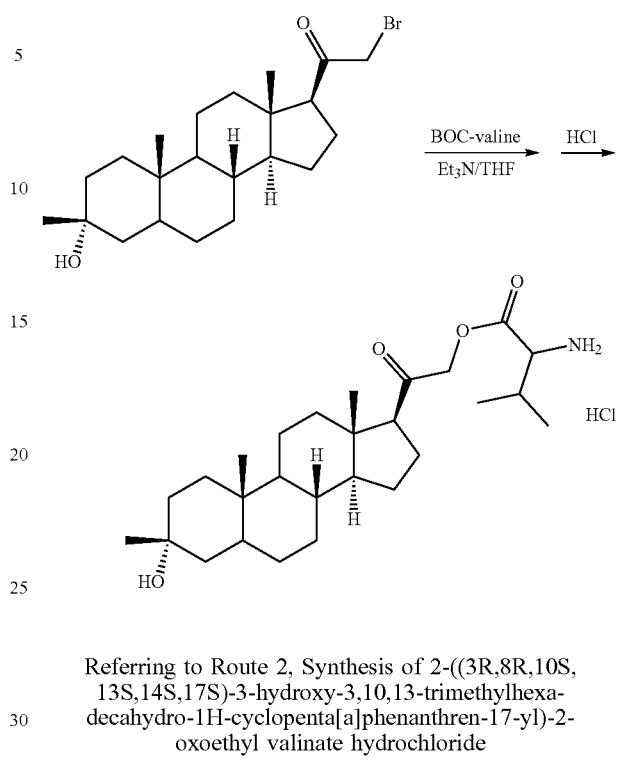

Referring to Route 2, Synthesis of 2-((3R,8R,10S, 13S,14S,17S)-3-hydroxy-3,10,13-trimethylhexadecahydro-1H-cyclopenta[a]phenanthren-17-yl)-2-oxoethyl valinate hydrochloride To a suspension of 21-Bromo-ganaxolone (5.0 g, 12.2 mmol) and BOC L-valine (26.5 g, 10 eq.) in 500 mL of acetone was added trimethylamine (20 mL, 13 eq.). The resulting mixture was heated at 65° C. for 5.5 h. It was then cooled to RT and was concentrated. The residue was partitioned between dichloromethane and water. The aqueous layer was extracted twice with dichloromethane. The combined organic layer was washed with brine, dried over Na$_2$SO$_4$ and concentrated. Biotage purification 20-80% EtOAc in hexane provided 5.59 g of the desired product (84% yield).

The above product was dissolved in 200 mL of methanol and 34 mL of 3N HCl in methanol was added. The mixture was stirred at RT for 72 h and was concentrated. The product was purified by reverse phase Biotage C-18 column with 10-90% CH$_3$CN in 0.1% TFA in H$_2$O. Pure fractions were collected and 7 mL of 3N HCl in MeOH was added. Lyophilization afforded 3.46 g of 2-((3R,8R,10S,13S,14S, 17S)-3-hydroxy-3,10,13-trimethylhexadecahydro-1H-cyclopenta[a]phenanthren-17-yl)-2-oxoethyl valinate hydrochloride. $^1$H NMR (400 MHz, CD3OD): δ 5.00 (d, J=17.0 Hz, 1H), 4.76 (d, J=16.9 Hz, 1H), 4.02 (d, J=4.4 Hz, 1H), 2.60 (t, J=8.8 Hz, 1H), 2.37 (pd, J=7.0, 4.4 Hz, 1H), 2.13 (q, J=11.6, 10.7 Hz, 1H), 2.06-1.97 (m, 1H), 1.80-1.58 (m, 4H), 1.58-1.28 (m, 5H), 1.22 (dd, J=10.8, 3.2 Hz, 4H), 1.15 (d, J=4.2 Hz, 3H), 1.14 (t, J=2.1 Hz, 7H), 1.10-0.78 (m, 1H), 0.76 (s, 4H), 0.62 (s, 3H). MS: M+1, 448.32; 2M+1, 895.13. UV: 201, 280 nM. HPLC: Sunfire C18 5 250×4.6 mm; flow 1.0 mL/min; Waters 996 PDA detection at 210 nm; solvent 40% Acetonitrile in H$_2$O (0.1% TFA) over 30 min; retention time 6.31 min; 94.4% pure. Solubility: 2 mg/mL in pH=7 phosphate buffer.

In another embodiment, the disclosure provides a method for using 21-Bromo ganaxolone to make 21-OH Ganaxolone Lysine. The method of making 21-OH Ganaxolone Lysine from 21-Bromo Ganaxolone is shown below in Route 3.

Route 3

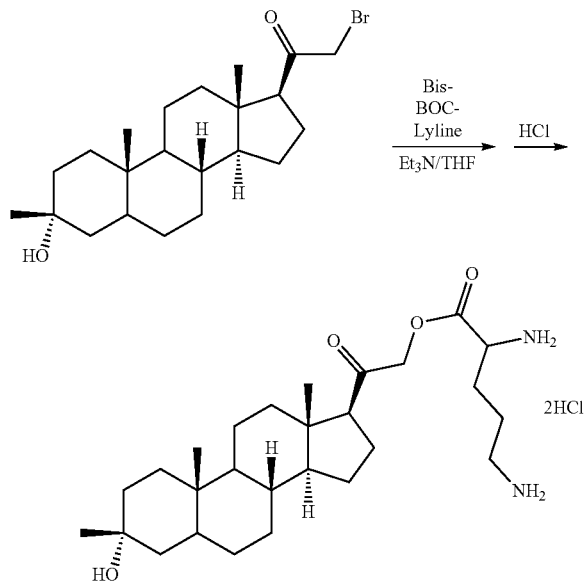

Referring to Route 3, Synthesis of 2-((3R,8R,10S, 13S,14S,17S)-3-hydroxy-3,10,13-trimethylhexadecahydro-1H-cyclopenta[a]phenanthren-17-yl)-2-oxoethyl 2,5-diaminopentanoate dihydrochloride To a suspension of 21-Bromo-ganaxolone (5.5 g, 13.4 mmol) and bis-BOC L-lysine (23.4 g, 5 eq.) in 500 mL of acetone was added trimethylamine (11 mL, 6.5 eq.). The resulting mixture was heated at 65° C. for 3 h. It was then cooled to RT and was concentrated. The residue was partitioned between dichloromethane and water. The aqueous layer was extracted twice with dichloromethane. The combined organic layer was washed with brine, dried over $Na_2SO_4$ and concentrated. Biotage purification 20-80% EtOAc in hexane provided 8.8 g of the desired product (97% yield).

The above product was dissolved in 300 mL of methanol and 43 mL of 3N HCl in methanol (10 eq.) was added. The mixture was heated at 55° C. for 2.5 h. It was cooled and was concentrated. The product was purified by reverse phase Biotage C-18 column with 10-90% $CH_3CN$ in 0.1% TFA in $H_2O$. Pure fractions were collected and 9 mL of 3N HCl in MeOH was added. Lyophilization afforded 3.5 g (57%). NMR: 1H (400 MHz, Methanol-d4) δ 5.06 (d, J=17.3 Hz, 1H), 4.75 (d, J=17.3 Hz, 1H), 4.17 (t, J=6.2 Hz, 1H), 3.02-2.93 (m, 2H), 2.62 (t, J=8.7 Hz, 1H), 2.05 (dddd, J=29.6, 18.1, 13.1, 6.8 Hz, 4H), 1.84-1.60 (m, 8H), 1.60-1.27 (m, 5H), 1.22 (dt, J=12.4, 5.0 Hz, 4H), 1.14 (d, J=1.0 Hz, 3H), 1.06-0.92 (m, 1H), 0.83 (dd, J=14.5, 10.8 Hz, 1H), 0.76 (d, J=1.1 Hz, 3H), 0.61 (s, 3H). MS: M+1, 477.36; 2M+1, 953.08. UV: 201, 281 nM. HPLC: X-Bridge C18 5µ 250×4.6 mm; flow 1.0 mL/min; Waters 996 PDA detection at 207 nm; solvent 10-90% Acetonitrile in $H_2O$ (0.1% TFA) over 20 min; retention time 11.08 min; 96.1% pure. Solubility: 9.7 mg/mL. Stability: 75% prodrug remain after 24 h in PBS (pH=7) at the solubility (9.7 mg/mL) concentration.

In another embodiment, the disclosure provides a method for using 21-Bromo ganaxolone to make 21-OH Ganaxolone Phosphate Disodium. The method of making 21-OH Ganaxolone Phosphate Disodium from 21-Bromo Ganaxolone is shown below in Route 4.

Route 4

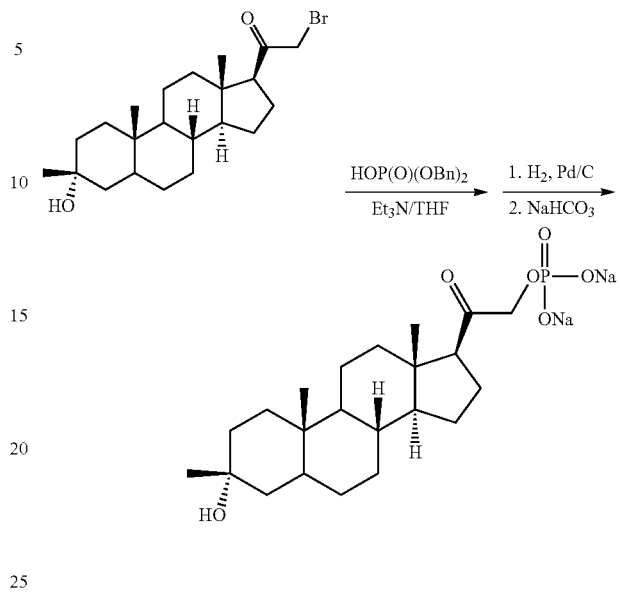

Referring to Route 4, Synthesis of bis-sodium 2-((3R,8R,10S,13S,14S,17S)-3-hydroxy-3,10,13-trimethylhexadecahydro-1H-cyclopenta[a]phenanthren-17-yl)-2-oxoethyl phosphate The mixture of 21-bromo-ganaxolone (0.82 g, 1.99 mmol), dibenzyl phosphate (1.66 g, 3 eq.) and trimethylamine (0.83 mL, 3.3 eq.) in 26 mL of THF was heated at 80° C. for 3 h. It was cooled and was concentrated. Biotage purification (10-80% EtOAc in hexane) afforded the desired product (0.675 g, 56% yield). LCMS (M+1, 609.38). 1H NMR (400 MHz, Chloroform-d3) δ 7.41-7.27 (m, 10H), 5.21-4.98 (m, 4H), 4.57-4.32 (m, 2H), 2.44 (t, J=8.8 Hz, 1H), 2.15 (q, J=11.6, 10.7 Hz, 1H), 1.81 (d, J=9.0 Hz, 1H), 1.66 (dd, J=11.4, 6.0 Hz, 3H), 1.52 (d, J=18.7 Hz, 7H), 1.42-1.22 (m, 3H), 1.20 (d, J=1.4 Hz, 3H), 1.18-1.01 (m, 1H), 0.94 (qd, J=11.7, 11.2, 5.0 Hz, 1H), 0.83-0.75 (m, 1H), 0.74 (s, 3H), 0.59 (s, 3H).

The above product (0.675 g, 1.11 mmol) was dissolved in 18 mL of MeOH and 10 mL of THF. To it was added 118 mg of 10% Pd/C (0.1 eq.). The mixture was degassed and was stirred under H2 balloon for 2.5 h at RT. It was filtered through CELITE®, washed with dichloromethane and concentrated to give 0.48 g of 2-((3R,8R,10S,13S,14S,17S)-3-hydroxy-3,10,13-trimethylhexadecahydro-1H-cyclopenta[a]phenanthren-17-yl)-2-oxoethyl phosphate, which was dissolved in 100 mL of MeOH and 30 mL of $H_2O$ and cooled in an ice bath. 2 eq. of NaHCO3 (0.19 g) in 10 mL was dropwise added and pH was monitored for the change of 3 to 7. It was stirred for 10 min after addition. Volatiles were evaporated and the aqueous solution was lyophilized to give 0.52 g of bis-sodium 2-((3R,8R,10S,13S,14S,17S)-3-hydroxy-3,10,13-trimethylhexadecahydro-1H-cyclopenta[a]phenanthren-17-yl)-2-oxoethyl phosphate. NMR: 1H (400 MHz, Methanol-d4) δ 4.53 (dd, J=20.1, 14.2 Hz, 2H), 2.57-2.75 (m, 1H), 2.22 2.07 (m, 1H), 2.02 (d, J=11.7 Hz, 1H), 1.77-1.59 (m, 5H), 1.59-1.27 (m, 7H), 1.23 (d, J=10.7 Hz, 6H), 1.14 (s, 3H), 1.00 (q, J=10.8, 9.6 Hz, 1H), 0.86-0.79 (m, 1H), 0.77 (s, 3H), 0.65 (d, J=1.8 Hz, 3H). MS: M−1, 427.27; 2M−1, 855.21; M+1, 429.11; 2M+1, 857.18. UV: 201, 280 nM. HPLC: Sunfire C18 5 250×4.6 mm; flow 1.0 mL/min; Waters 996 PDA detection at 210 nm; solvent 40% Acetonitrile in H$_2$O (0.1% TFA) over 60 min; retention time 8.3 min; 95% pure. Solubility: >10 mg/mL in PBS (pH=7.4). Stability: No decomposition observed at 26 h in PBS (pH=7.4).

In another embodiment, the disclosure provides a method for using 21-Bromo ganaxolone to make 21-OH Ganaxolone Succinate Sodium. The method of making 21-OH Ganaxolone Succinate Sodium from 21-Bromo Ganaxolone is shown below in Route 5.

Route 5

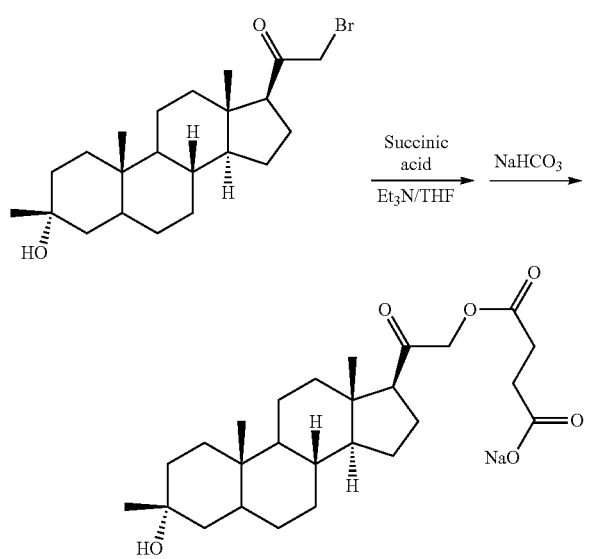

Referring to Route 5, synthesis of sodium 4-(2-((3R,8R,10S,13S,14S,17S)-3-hydroxy-3,10,13-trimethylhexadecahydro-1H-cyclopenta[a]phenanthren-17-yl)-2-oxoethoxy)-4-oxobutanoate 21-Bromoganaxolone (0.6 g, 1.46 mmol) and succinic acid (2.76 g, 16 eq.) were suspended in 65 mL of acetone and 2.4 mL of triethyl amine (13 eq.). The mixture was heated at 65° C. for 2 h. Volatiles were removed and the residue was partitioned between water and DCM. The aqueous layer was extracted twice and the combined organic layer was washed with brine and dried (Na$_2$SO$_4$). Biotage purification with 1-10% MeOH in (45% EtOAc in DCM) provided 0.44 g of product (96% pure), which was dissolved in 20 mL of methanol at 0° C. To it was added 0.079 g of NaHCO$_3$ in 5 mL of H$_2$O also cooled at 0° C. dropwise until pH reached to 7. Freeze-dry afforded 0.39 g of sodium 4-(2-((3R,8R,10S,13S,14S,17S)-3-hydroxy-3,10,13-trimethylhexadecahydro-1H-cyclopenta[a]phenanthren-17-yl)-2-oxoethoxy)-4-oxobutanoate.

NMR: 1H (400 MHz, Methanol-d4) δ 4.75 (dd, J=17.1, 0.9 Hz, 1H), 4.56 (dd, J=17.0, 1.7 Hz, 1H), 2.68-2.58 (m, 2H), 2.46 (dd, J=7.6, 6.5 Hz, 2H), 2.16-1.97 (m, 2H), 1.66 (ddt, J=18.3, 14.5, 4.6 Hz, 5H), 1.58-1.26 (m, 9H), 1.20 (td, J=9.2, 8.1, 2.7 Hz, 5H), 1.13 (s, 3H), 0.98 (ddd, J=23.4, 18.5, 10.7 Hz, 1H), 0.83-0.78 (m, 1H), 0.76 (s, 3H), 0.61 (s, 3H).

MS: Negative ion mode: 2M−1, 895.44; positive ion mode: M−18+1, 431.12; 2M+23, 919.18. UV: 201, 280 nM. HPLC: Sunfire C18 5 250×4.6 mm; flow 1.0 mL/min; Waters 996 PDA detection at 210 nm; solvent 50% Acetonitrile in H$_2$O (0.1% TFA) over 60 min; retention time 15.5 min; 94% pure. Solubility: 0.96 mg/mL. Stability: 98% remaining after 24 h in pH=7 phosphate buffer.

In another embodiment, the disclosure provides a method for using 21-Bromo ganaxolone to make 21-OH Ganaxolone Malic Acid. The method of making 21-OH Ganaxolone Malic Acid from 21-Bromo Ganaxolone is shown below in Route 6.

Route 6

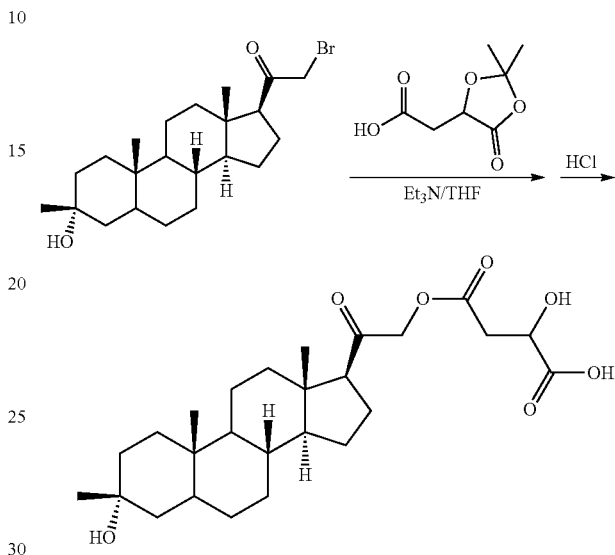

Referring to Route 6, synthesis of 2-hydroxy-4-(2-((3R,8R,10S,13S,14S,17S)-3-hydroxy-3,10,13-trimethylhexadecahydro-1H-cyclopenta[a]phenanthren-17-yl)-2-oxoethoxy)-4-oxobutanoic acid The mixture of 21-bromoganaxolone (300 mg, 0.73 mmol), (R)-(−)-2,2-dimethyl-5-oxo-1,3-dioxolane-4-acetic acid (1.3 g, 7.3 mmol, 10 eq.) and triethyl amine (1.2 mL, 13 eq.) in 30 mL of acetone was heated at 65° C. for 3 h. It was then concentrated and partitioned between water and DCM. The aqueous layer was extracted with DCM three times and the combined organic layer was washed with brine and dried (Na$_2$SO$_4$). Biotage purification with 20-80% EtOAc in hexane afforded 345 mg of the protected product, which was dissolved in 20 mL of HOAc, 5 mL of THF and 10 mL of water. The resulting mixture was heated at 45 degree for 5 h. Volatiles were removed and water was evaporated by freeze-drying. Purification on a reverse phase Biotage with MeCN and 0.1% TFA in H$_2$O gave 251 mg of the final product.

NMR: 1H (400 MHz, Methanol-d4) δ 4.83 (d, J=17.1 Hz, 1H), 4.63 (d, J=17.1 Hz, 1H), 4.52 (dd, J=8.0, 4.1 Hz, 1H), 2.95 (dd, J=16.1, 4.0 Hz, 1H), 2.78 (dd, J=16.0, 7.9 Hz, 1H), 2.63 (t, J=8.9 Hz, 1H), 2.14 (q, J=11.0, 10.3 Hz, 1H), 2.03 (dt, J=12.1, 3.3 Hz, 1H), 1.68 (ddd, J=21.9, 10.2, 4.0 Hz, 5H), 1.60-1.27 (m, 8H), 1.22 (td, J=9.5, 7.7, 2.8 Hz, 5H), 1.15 (s, 3H), 1.06-0.87 (m, 1H), 0.82 (dd, J=11.7, 4.1 Hz, 1H), 0.78 (s, 3H), 0.63 (s, 3H).

MS: M+NH4, 482.22; 2M+1, 929.17.
UV: 205, 284 nM
HPLC: X-Bridge C18 5μ 250×4.6 mm; flow 1.0 mL/min; Waters 996 PDA detection at 207 nm; solvent 10-90% Acetonitrile in H$_2$O (0.1% TFA) over 20 min; retention time 16.5 min; 96.6% pure for batch 1 & 96.0% for batch 2.

Solubility: 0.406 mg/mL in PBS (pH=7.4). Stability: 100% remaining after 24 h in PBS (pH=7.4).

In another embodiment, the disclosure provides a method for using 21-Bromo ganaxolone to make 21-OH Ganaxolone Piperdine Diol. The method of making 21-OH Ganaxolone Piperdine Diol from 21-Bromo Ganaxolone is shown below in Route 7.

Route 7

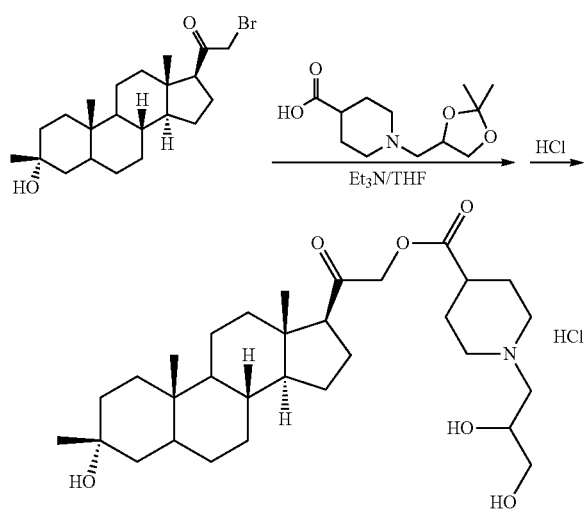

Referring to Route 7, synthesis of 2-((3R,8R,10S, 13S,14S,17S)-3-hydroxy-3,10,13-trimethylhexadecahydro-1H-cyclopenta[a]phenanthren-17-yl)-2-oxoethyl 1-(2,3-dihydroxypropyl)piperidine-4-carboxylate hydrochloride Synthesis of lithium 1-((2,2-dimethyl-1,3-dioxolan-4-yl)methyl)piperidine-4-carboxylate was accomplished in two steps. Step 1: to a solution of (2,2-dimethyl-1,3-dioxolan-4-yl)methanol (2.84 g, 21.5 mmol) in 50 mL of dichloromethane and 5.4 mL of triethylamine (2 eq.) at 0 degree was added methanesulfonyl chloride (1.2 eq. 2 mL). The resulting mixture was stirred at 0° C. for 5 min and at RT for 1 h. Volatiles were removed and the residue was dissolved in 30 mL of MeCN. To this solution were also added triethylamine (5.4 mL, 39 mmol) and ethyl 4-piperidinecarboxylate (3 mL, 19.5 mmol). The resulting mixture was heated at 80 degree for 2 h 15 min. It was cooled to RT and concentrated. Ethyl 1-((2,2-dimethyl-1,3-dioxolan-4-yl)methyl)piperidine-4-carboxylate was purified on a Biotage column using 2-20% (10% NH4OH in MeOH) in DCM to afford 2.57 g (49% overall yield); Step 2: 2.57 g of ethyl 2-(2,2-dimethyl-5-oxo-1,3-dioxolan-4-yl)acetate (9.5 mmol) was stirred with LiOH—H$_2$O (250 mg, 1.1 eq.) in 6 mL of THF, 6 mL of water and 3 mL of MeOH at RT for 5 h. Volatiles were removed and the residue was dried under high vacuum to give 2.8 g of lithium 1-((2,2-dimethyl-1,3-dioxolan-4-yl)methyl)piperidine-4-carboxylate.

21-Bromoganaxolone (590 mg, 1.44 mmol) and 1.75 g (5 eq.) of lithium 1-(2,2-dimethyl-1,3-dioxolan-4-yl)methyl)piperidine-4-carboxylate were dissolved in 30 mL of acetone and heated at 65° C. for 10 h. Volatiles were removed and the residue was partitioned between water and ethyl acetate. The aqueous layer was extracted with ethyl acetate and the combined organic layer was washed with brine and dried over Na$_2$SO$_4$. Purification with 1-10% MeOH in DCM on a Biotage column afforded 481 mg of the desired product, 2-((3R,8R,10S,13S,14S,17S)-3-hydroxy-3,10,13-trimethylhexadecahydro-1H-cyclopenta[a]phenanthren-17-yl)-2-oxoethyl 1-((2,2-dimethyl-1,3-dioxolan-4-yl)methyl)piperidine-4-carboxylate. 481 mg of the above product, 2-((3R,8R,10S,13S,14S,17S)-3-hydroxy-3,10,13-trimethylhexadecahydro-1H-cyclopenta[a]phenanthren-17-yl)-2-oxoethyl 1-((2,2-dimethyl-1,3-dioxolan-4-yl)methyl)piperidine-4-carboxylate (0.84 mmol) was dissolved in 60 mL of MeOH. To it was added p-toluenesulfonic acid (2 eq. 319 mg). The resulting mixture was heated at 40° C. for 2 h. The mixture was neutralized with NaHCO$_3$ (2 eq.) and was concentrated. Purification on a Biotage column with 2-10% MeOH in 1% NH$_4$OH in DCM gave 384 g of 2-((3R,8R,10S,13S,14S,17S)-3-hydroxy-3,10,13-trimethylhexadecahydro-1H-cyclopenta[a]phenanthren-17-yl)-2-oxoethyl 1-(2,3-dihydroxypropyl)piperidine-4-carboxylate, which was mixed with 2 eq. 3N HCl in methanol and concentrated under vacuum. The final product, 2-((3R,8R,10S,13S,14S,17S)-3-hydroxy-3,10,13-trimethylhexadecahydro-1H-cyclopenta[a]phenanthren-17-yl)-2-oxoethyl 1-(2,3-dihydroxypropyl)piperidine-4-carboxylate hydrochloride, 410 mg was obtained in 97.4% purity.

NMR: 1H (400 MHz, Methanol-d4) δ 7.77-7.65 (m, 4H), 7.23 (d, J=8.1 Hz, 4H), 4.68 (d, J=17.1 Hz, 1H), 4.58 (s, 2H), 4.01 (dtd, J=10.1, 5.1, 3.2 Hz, 1H), 3.60-3.36 (m, 2H), 3.24-2.97 (m, 3H), 2.81 (s, 1H), 2.61 (t, J=8.9 Hz, 1H), 2.37 (s, 5H), 2.24-1.97 (m, 6H), 1.79-1.58 (m, 4H), 1.58-1.28 (m, 6H), 1.24 (dt, J=10.6, 2.7 Hz, 4H), 1.15 (s, 3H), 0.98 (dt, J=17.7, 11.6 Hz, 1H), 0.83 (dd, J=13.0, 8.7 Hz, 1H), 0.78 (s, 3H), 0.63 (s, 3H). MS: M+1, 534.5 for free base parent compound. UV: 204, 282 nM. HPLC: X-Bridge C18 5µ 250×4.6 mm; flow 1.0 mL/min; Waters 996 PDA detection at 207 nm; solvent 10-90% Acetonitrile in H$_2$O (0.1% TFA) over 20 min; retention time 13.5 min; 97.4%. Solubility: 0.48 mg/mL in pH=7 phosphate buffer. Stability: 100% remaining after 24 h in pH=7 phosphate buffer.

In another embodiment, the disclosure provides a method for using 21-Bromo ganaxolone to make 21-OH Ganaxolone methyl phosphite sodium salt. The method of making 21-OH Ganaxolone methyl phosphite sodium salt from 21-Bromo Ganaxolone is shown below in Route 8.

Route 8

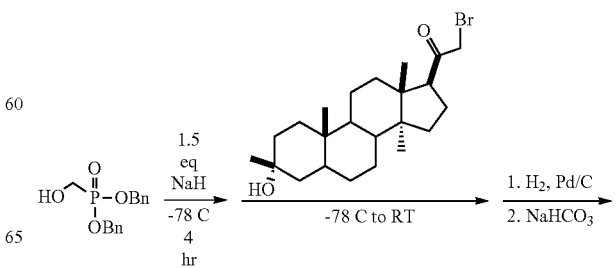

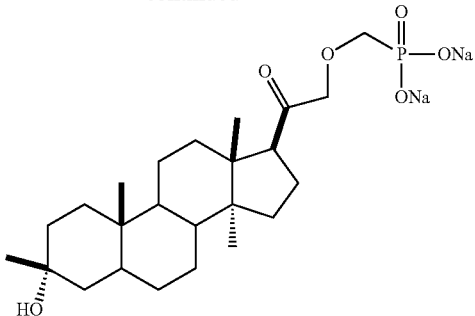

Referring to Route 8, synthesis of dibenzyl ((2-((3R,10S,13S,17S)-3-hydroxy-3,10,13-trimethyl-hexadecahydro-1H-cyclopenta[a]phenanthren-17-yl)-2-oxoethoxy)methyl)phosphonate The mixture of dibenzyl phosphite (4.11 g, 15.7 mmol), paraformaldehyde (0.517 g, 1.1 eq.) and triethyl amine (0.2 mL, 0.1 eq.) was heated in a capped vial at 130° C. for 25 min. The mixture was then cooled and purified on a Biotage column with 5-70% EtOAc in DCM to give 3.27 g of dibenzyl (hydroxymethyl)phosphonate (71% yield).

Dibenzyl (hydroxymethyl)phosphonate (0.99 g, 3.39 mmol) was dissolved in 7 mL of THF and cooled to −75° C. NaH (60% in oil, 203 mg, 1.5 eq.) was added and the mixture was stirred at −75° C. for 4 h. 21-Bromoganaxolone (2.79 g, 6.78 mmol, 2 eq.) was then added. The mixture was allowed to warm to RT slowly overnight while stirring. The reaction was quenched with NH₄Cl (sat.) and was diluted with EtOAc. The organic layer was washed with brine and was dried over Na₂SO₄. Biotage purification with 2-80% EtOAc in hexane gave 1 g of the product, dibenzyl ((2-((3R,10S,13S,17S)-3-hydroxy-3,10,13-trimethylhexadecahydro-1H-cyclopenta[a]phenanthren-17-yl)-2-oxoethoxy)methyl)phosphonate (47%).

$^1$H NMR (400 MHz, DMSO-d6) δ 7.33 (q, J=3.9, 3.4 Hz, 10H), 5.13-4.94 (m, 4H), 4.27-4.04 (m, 2H), 4.04-3.90 (m, 2H), 3.84 (s, 1H), 2.51 (d, J=9.0 Hz, 1H), 2.02-1.86 (m, 1H), 1.76 (d, J=11.7 Hz, 1H), 1.64-1.39 (m, 6H), 1.38-1.04 (m, 13H), 1.02 (s, 3H), 0.91-0.68 (m, 1H), 0.64 (s, 3H), 0.44 (s, 3H).

LCMS: M+1, 623.32.

Synthesis of bis-sodium ((2-((3R,10S,13S,17S)-3-hydroxy-3,10,13-trimethylhexadecahydro-1H-cyclopenta[a]phenanthren-17-yl)-2-oxoethoxy)methyl) phosphonate Dibenzyl ((2-((3R,10S,13S,17S)-3-hydroxy-3,10,13-trimethylhexadecahydro-1H-cyclopenta[a]phenanthren-17-yl)-2-oxoethoxy)methyl)phosphonate (0.627 g, 1 mmol) was stirred under H2 balloon in 11 mL of MeOH and 107 mg of 10% Pd/C (0.1 eq.) at RT for 2 h. The mixture was diluted with MeOH and filtered through CELITE®. The filtrate was concentrated to give 417 mg of white solid, which was dissolved in 5 mL of MeOH and cooled in an ice bath. NaHCO₃ (0.1 M, 20 mL, 2 eq.) was dropwise added at 0° C. until pH=7. MeOH was removed under rotary evaporator and water was lyophilized to give 451 mg of the product was sodium salt.

NMR: 1H (400 MHz) (CD3OD): δ 4.26 (s, 2H), 3.52 (dd, J=9.2, 2.6 Hz, 2H), 3.31 (d, J=12.9 Hz, 1H), 2.55 (t, J=8.7 Hz, 1H), 2.12 (t, J=10.6 Hz, 1H), 1.92 (d, J=11.2 Hz, 1H), 1.78-1.15 (m, 17H), 1.13 (s, 3H), 0.83-0.71 (m, 1H), 0.97 (t, J=9.5 Hz, 1H), 0.76 (s, 3H), 0.69-0.51 (m, 1H), 0.63 (s, 3H). UV: Absorbances at 207 nm. MS: 443.1 (M+1) as free acid. HPLC: X-Bridge C18 5µ 250×4.6 mm; flow 1.0 mL/min; Waters 996 PDA detection at 212 nm; solvent 50% Acetonitrile in H₂O (0.1% formic acid) over 15 min; retention time 5.21 min in; 100% purity. Solubility: 7.3 mg/mL in pH=7.4 PBS. Stability: no decomposition observed over 24 h in pH=7.4 PBS.

In another embodiment, the disclosure provides a method for using 21-OH ganaxolone to make 21-OH Ganaxolone Carbamate. The method of making 21-OH Ganaxolone Carbamate from 21-OH Ganaxolone is shown below in Route 9.

Route 9

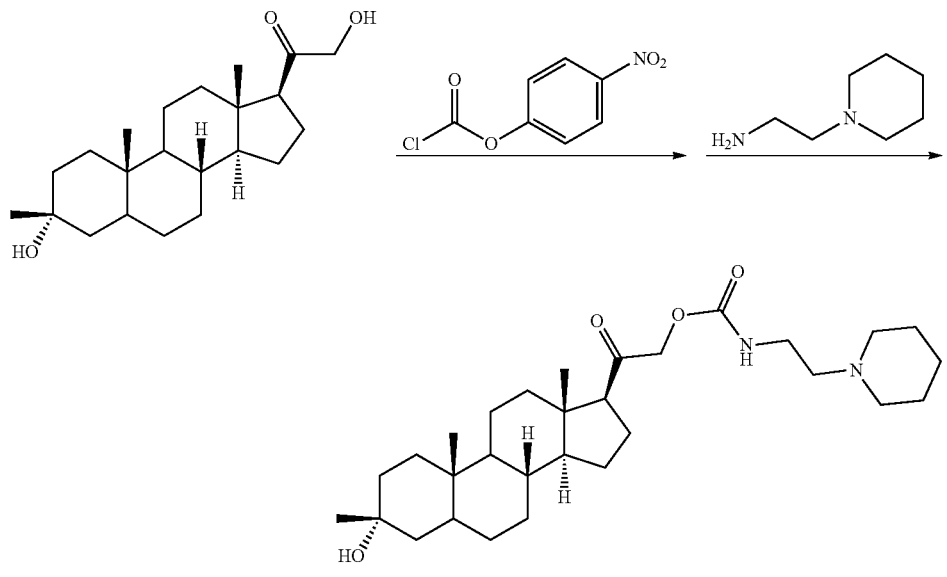

21-OH GX Carbamate

Referring to Route 9, Synthesis of 2-((3R,8R,10S,13S,14S,17S)-3-hydroxy-3,10,13-trimethylhexadecahydro-1H-cyclopenta[a]phenanthren-17-yl)-2-oxoethyl (4-nitrophenyl) carbonate

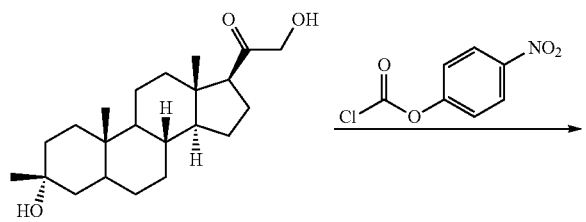

(Na$_2$SO$_4$). Biotage purification (20-80% EtOAc in hexane) gave 545 mg of the product (74% yield).

1H NMR (400 MHz, Chloroform-d) δ 8.40-8.16 (m, 2H), 7.49-7.35 (m, 2H), 4.85 (d, J=16.8 Hz, 1H), 4.69 (d, J=16.8 Hz, 1H), 2.51 (t, J=8.9 Hz, 1H), 2.28-2.15 (m, 1H), 2.02-1.93 (m, 1H), 1.78-1.59 (m, 3H), 1.59-1.43 (m, 8H), 1.43-1.32 (m, 2H), 1.32-1.22 (m, 3H), 1.20 (s, 3H), 1.19-1.10 (m, 2H), 1.03-0.90 (m, 1H), 0.85-0.76 (m, 1H), 0.74 (s, 3H), 0.66 (s, 3H).

Synthesis of 2-((3R,8R,10S,13S,14S,17S)-3-hydroxy-3,10,13-trimethylhexadecahydro-1H-cyclopenta[a]phenanthren-17-yl)-2-oxoethyl (2-(piperidin-1-yl)ethyl)carbamate

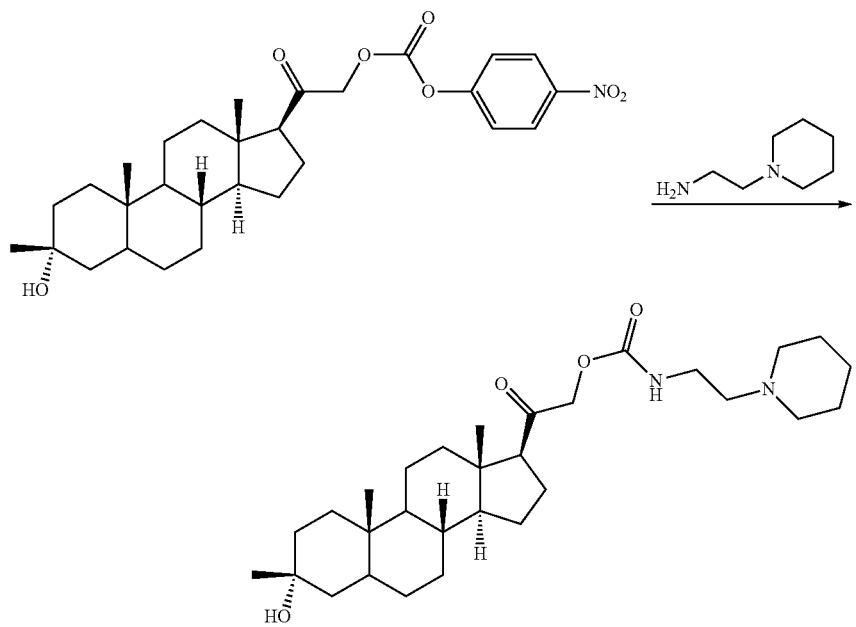

21-OH GX Carbamate

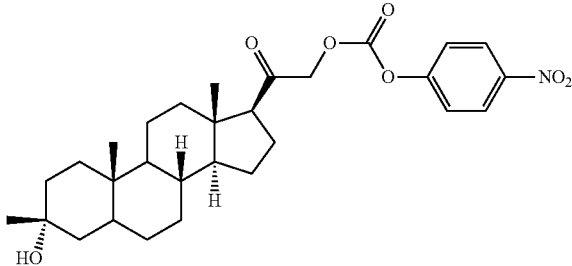

21-Hydroxyganaxolone (0.5 g, 1.49 mmol) was dissolved in 24 mL of THF. To it were added p-nitrophenol chloroformate (349 mg, 1.2 eq.) and DMAP (228 mg, 1.3 eq.). The resulting mixture was stirred at RT overnight and was quenched with water. EtOAc was used to extract and the organic layer was washed with water, brine and dried 2-((3R,8R,10S,13S,14S,17S)-3-hydroxy-3,10,13-trimethylhexadecahydro-1H-cyclopenta [a]phenanthren-17-yl)-2-oxoethyl (4-nitrophenyl) carbonate (300 mg, 0.585 mmol) and 1-(2-Aminoethyl)piperidine (0.25 mL, 3 eq.) were stirred in 15 mL of THF at RT for 2 h. Volatiles were removed and Biotage purification with 10% (10% NH$_4$OH in MeOH)) in DCM (isocratic) gave 220 mg of the product.

NMR: 1H (400 MHz) (CD3OD): δ 5.47 (s, 2H), 4.51 (d, J=9.6 Hz, 1H), 4.12 (d, J=10 Hz, 1H), 3.47 (d, J=16 Hz, 1H), 3.25 (m, 1H), 2.69 (br. 1H), 2.5 (m, 2H), 2.25-2.4 (m, 4H), 1.95 (t, J=9.6 Hz, 1H), 1.2-1.7 (m, 19H), 1.13 (s, 3H), 0.95 (m, 1H), 0.77 (s, 3H), 0.72 (s, 3H). MS: M+1, 503.45. UV: 202, 283 nM. HPLC: Sunfire C18 5µ 250×4.6 mm; flow 1.0 mL/min; Waters 996 PDA detection at 210 nm; solvent 40% Acetonitrile in H$_2$O (0.1% TFA) over 60 min; retention time 7.37 min; 100% pure. Solubility: 0.12 mg/mL at pH=7.4; 1.1 mg/mL at pH=6 of PBS. Stability: Decomposition at pH=6 was visible, but not quantified.

In one embodiment, the disclosure provides a method for using ganaxolone to make UCI-50027 and other intermediary compounds which are useful for preparing UCI-50027 derivatives. The method of making UCI-50027 is shown below in Route 10.

Route 10:

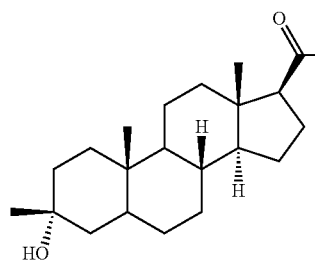

(ganaxolone)

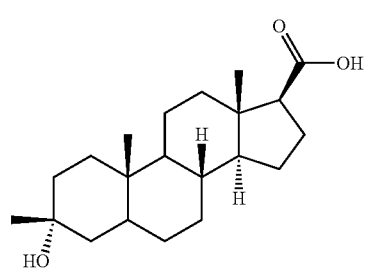

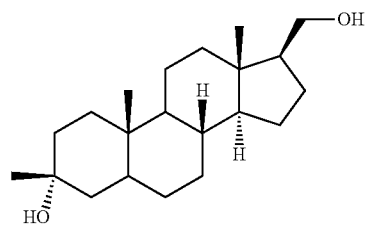

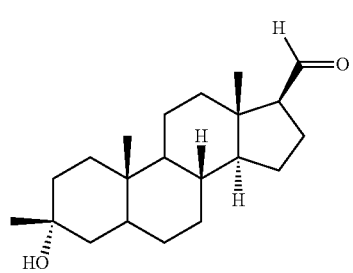

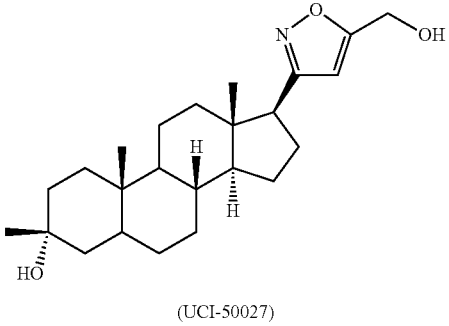

(UCI-50027)

Referring to Route 10, Synthesis of (3R,8R,10S,13S,14S,17S)-3-hydroxy-3,10,13-trimethylhexadecahydro-1H-cyclopenta[a]phenanthrene-17-carboxylic acid

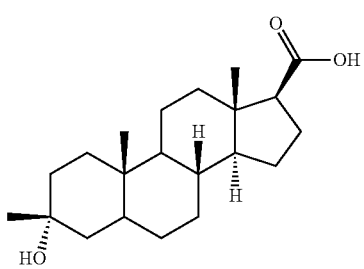

(21-OH-ganaxolone)

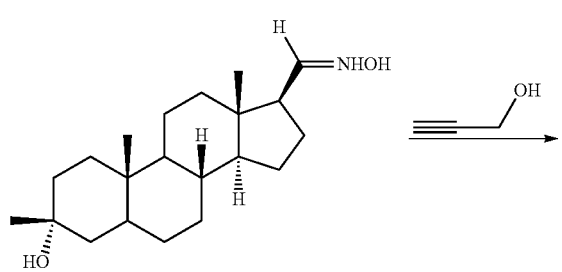

21-OH-ganaxolone (4.38 g, 12.6 mmol) and NaIO4 (13.44 g, 5 eq.) were heated in 47 mL of H$_2$O and 160 mL of THF at 50° C. for 18 h. It was acidified with 1 N HCl (160 mL) and the product was extracted with ethyl acetate three times. The organic layer was washed with brine and dried over Na$_2$SO$_4$. Concentration gave a yellow solid, which was washed with hexane and DCM. An off-white solid was obtained in 88% yield. 1H NMR (400 MHz, DMSO-d6) δ 11.85 (s, 1H), 3.83 (s, 1H), 2.24 (t, J=9.2 Hz, 1H), 1.98-1.83 (m, 2H), 1.73-1.40 (m, 4H), 1.40-1.05 (m, 14H), 1.03 (s, 3H), 0.96-0.78 (m, 1H), 0.73-0.62 (m, 1H), 0.68 (s, 3H), 0.59 (s, 3H).

Synthesis of (3R,8R,10S,13S,14S,17S)-17-(hydroxymethyl)-3,10,13-trimethylhexadecahydro-1H-cyclopenta[a]phenanthren-3-ol

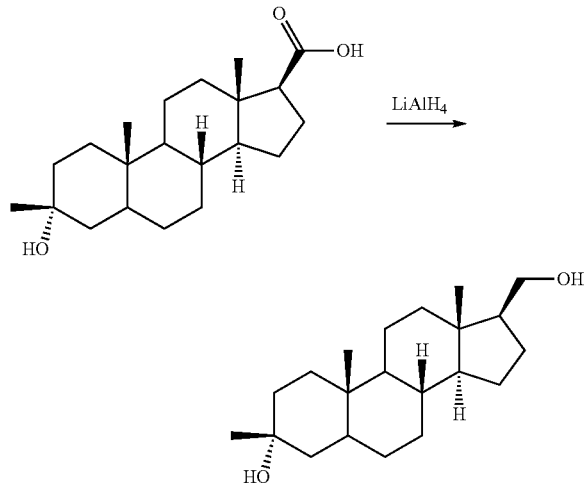

To a solution of (3R,8R,10S,13S,14S,17S)-3-hydroxy-3,10,13-trimethylhexadecahydro-1H-cyclopenta[a]phenanthrene-17-carboxylic acid (3.70 g, 11.1 mmol) in 220 mL of THF at 0° C. was added LAH (0.842 g, 22.2 mmol, 2 eq.) slowly. The mixture was stirred and was allowed to warm to RT, then was heated at 65° C. for 3 h. After it was cooled to RT, the reaction was quenched by adding 0.84 mL of H₂O, 0.84 mL of 15% NaOH and 2.52 mL of H₂O. The resulting suspension was diluted with EtOAc and stirred at RT for 30 min. It was filtered through a CELITE® pad and washed with EtOAc. The filtrate was concentrated to give quantitative amount of (3R,8R,10S,13S,14S,17S)-17-(hydroxymethyl)-3,10,13-trimethylhexadecahydro-1H-cyclopenta[a]phenanthren-3-ol (3.68 g).

1H NMR (400 MHz, DMSO-d6) δ 4.19-4.09 (m, 1H), 3.82 (s, 1H), 3.48-3.36 (m, 1H), 3.29-3.19 (m, 1H), 1.86-1.77 (m, 1H), 1.77-1.63 (m, 1H), 1.63-1.38 (m, 5H), 1.38-1.05 (m, 14H), 1.03 (d, J=0.9 Hz, 3H), 1.00-0.76 (m, 1H), 0.74-0.61 (m, 1H), 0.68 (s, 3H), 0.54 (s, 3H).

Synthesis of (3R,8R,10S,13S,14S,17S)-3-hydroxy-3,10,13-trimethylhexadecahydro-1H-cyclopenta[a]phenanthrene-17-carbaldehyde

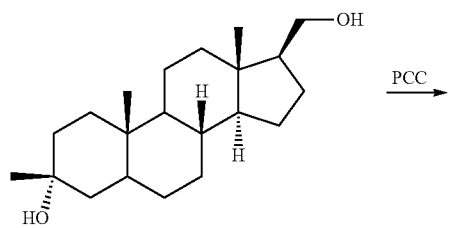

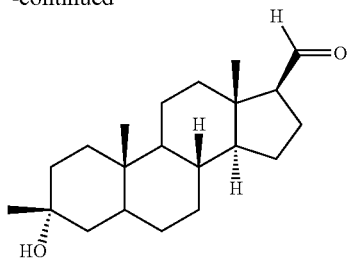

(3R,8R,10S,13S,14S,17S)-17-(hydroxymethyl)-3,10,13-trimethylhexadecahydro-1H-cyclopenta[a]phenanthren-3-ol (0.64 g, 2 mmol) was dissolved in 30 mL of DCM. To it were added PCC (0.646 g, 1.5 eq.) and 2 g of CELITE®. After the resulting mixture was stirred at RT for 3 h, it was filtered through a silica-gel pad and washed with DCM and EtOAc. The filtrate was concentrated to give 0.623 g of (3R,8R,10S,13S,14S,17S)-3-hydroxy-3,10,13-trimethylhexadecahydro-1H-cyclopenta[a]phenanthrene-17-carbaldehyde in 98% yield.

1H NMR (399 MHz, Chloroform-d) δ 9.76 (s, 1H), 2.29 (t, J=8.9 Hz, 1H), 2.16-1.90 (m, 2H), 1.79-1.32 (m, 11H), 1.33-1.07 (m, 7H), 1.20 (s, 3H), 1.07-0.88 (m, 1H), 0.86-0.76 (m, 1H), 0.75 (s, 3H).

Synthesis of (3R,8R,10S,13S,14S,17S)-17-(5-(hydroxymethyl)isoxazol-3-yl)-3,10,13-trimethylhexadecahydro-1H-cyclopenta[a]phenanthren-3-ol (UCI-50027)

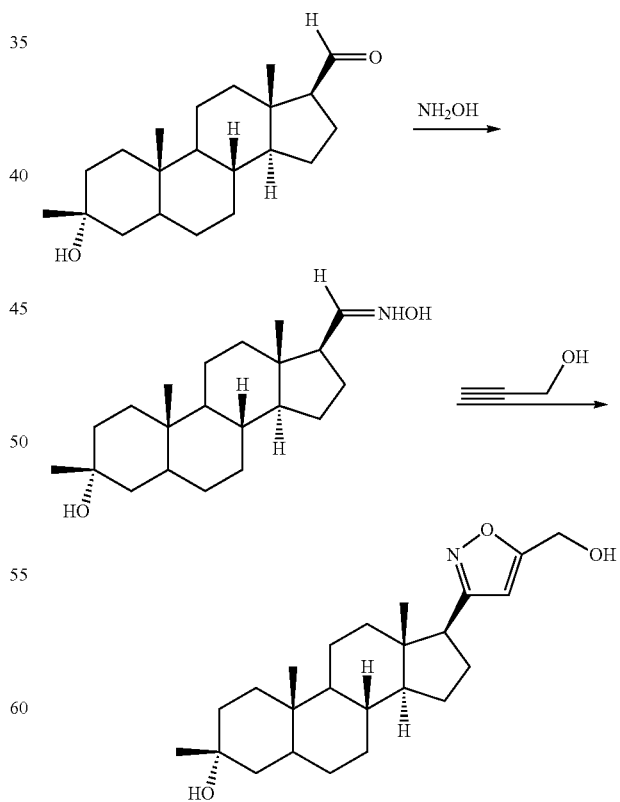

(UCI-50027)

The mixture of (3R,8R,10S,13S,14S,17S)-3-hydroxy-3,10,13-trimethylhexadecahydro-1H-cyclopenta[a]phenanthrene-17-carbaldehyde (0.623 g, 1.96 mmol), Na$_2$CO$_3$ (1.5 eq. 312 mg) and NH$_2$OH—HCl (204 mg, 1.5 eq.) in 30 ml of EtOH and 10 ml of H$_2$O were stirred at RT overnight. The mixture was then partitioned between water and EtOAc. The organic layer was washed with brine and dried over Na$_2$SO$_4$. Concentration gave 0.584 g of solid, (E)-3-hydroxy-3,10,13-trimethylhexadecahydro-1H-cyclopenta[a]phenanthrene-17-carbaldehyde oxime in 89%.

The mixture of (E)-3-hydroxy-3,10,13-trimethylhexadecahydro-1H-cyclopenta[a]phenanthrene-17-carbaldehyde oxime (1.69 g, 5.07 mmol), NCS (N-Chlorosuccimide, 0.71 g, 1.05 eq.) and pyridine (20 drops) in 100 mL of DCM was stirred at RT for 1.5 h. Propyargyl alcohol (1.6 mL, 5.4 eq.) and diisopropylethylamine (0.97 mL 1.1 eq.) were then added. The resulting mixture was stirred at RT overnight. The reaction mixture was diluted with DCM, washed with NaHCO$_3$ (sat.), brine and dried over Na$_2$SO$_4$. Biotage purification with 0-80% EtOAc in hexane gave (3R,8R,10S,13S,14S,17S)-17-(5-(hydroxymethyl)isoxazol-3-yl)-3,10,13-trimethylhexadecahydro-1H-cyclopenta[a]phenanthren-3-ol (UCI-50027) 1.13 g of in 58% yield.

1H NMR (400 MHz, DMSO-d6) δ 6.20 (d, J=0.8 Hz, 1H), 5.54 (tt, J=6.0, 0.9 Hz, 1H), 4.49 (dd, J=6.0, 0.8 Hz, 2H), 3.84 (s, 1H), 2.65 (t, J=9.7 Hz, 1H), 2.07-1.97 (m, 1H), 1.96-1.84 (m, 1H), 1.66 (dd, J=15.8, 10.8 Hz, 4H), 1.52 (d, J=13.3 Hz, 2H), 1.33 (t, J=7.0 Hz, 4H), 1.30-1.08 (m, 8H), 1.04 (s, 3H), 0.91 (dt, J=21.4, 11.2 Hz, 1H), 0.78-0.71 (m, 1H), 0.68 (s, 3H), 0.47 (s, 3H). UV: Absorbances at 214.2 nm.

TLC: (Silica Gel plates) 40% EtOAc/Hexane; Rf=0.35. HPLC: X-Bridge C18 5μ 250×4.6 mm; flow 1.0 mL/min; Waters 996 PDA detection at 210 nm; solvent 55% Acetonitrile in H$_2$O (0.1% formic acid) over 30 min; retention time 12.45 min; 99.6%. Solubility: <1 μg/mL In one embodiment, the disclosure provides a method for using UCI-50027 to make UCI-50027 Valine Citric salt. The method of making UCI-50027 Valine Citric salt is shown below in Route 11.

Route 11:

Referring to Route 11, synthesis of (3-((3R,8R,10S,13S,14S,17S)-3-hydroxy-3,10,13-trimethylhexadecahydro-1H-cyclopenta[a]phenanthren-17-yl) isoxazol-5-yl)methyl L-valinate 2-hydroxypropane-1,2,3-tricarboxylic acid To a solution of (3R,8R,10S,13S,14S,17S)-17-(5-(hydroxymethyl)isoxazol-3-yl)-3,10,13-trimethylhexadecahydro-1H-cyclopenta[a]phenanthren-3-ol (UCI-50027) (285 mg, 0.735 mmol) in 8 mL of THF and triethyl amine (0.15 mL, 1.5 eq.) at 0° C. was added methanesulfonyl chloride (0.063 mL, 1.1 eq.). After the resulting mixture was stirred at 0° C. for 1 h, it was diluted with EtOAc. The organic layer was washed with brine and dried over Na$_2$SO$_4$. The residue after concentration was dissolved in 8 mL of acetone. To it were added BOC-L-valine (1.60 g, 10 eq.) and triethyl amine (1.33 mL, 13 eq.). The resulting mixture was heated at 65° C. for 2.5 h. It was cooled and the volatiles were removed. The residue was diluted with DCM and was washed with brine and dried over Na$_2$SO$_4$. Biotage purification with 0-60% EtOAc in hexane gave 316 mg of (3-((3R,8R,10S,13S,14S,17S)-3-hydroxy-3,10,13-trimethylhexadecahydro-1H-cyclopenta[a]phenanthren-17-yl) isoxazol-5-yl)methyl (tert-butoxycarbonyl)-L-valinate (73%).

The above product (316 mg) was stirred with 3M of HCl in 5 mL of MeOH (10 eq.) at RT for 24 h. The mixture was purified on a C18 reverse phase Biotage column with 0-50% and 50-100% MeOH in 0.1% HCOOH in H$_2$O to give 161 mg of (3-((3R,8R,10S,13S,14S,17S)-3-hydroxy-3,10,13-trimethylhexadecahydro-1H-cyclopenta[a]phenanthren-17-yl)isoxazol-5-yl)methyl L-valinate, which was dissolved in 2 mL of MeOH and mixed with 1 eq. of 2M citric acid solution (0.166 ml). Lyophilization provided 208 mg of (3-((3R,8R,10S,13S,14S,17S)-3-hydroxy-3,10,13-trimethylhexadecahydro-1H-cyclopenta[a]phenanthren-17-yl) isoxazol-5-yl)methyl L-valinate 2-hydroxypropane-1,2,3-tricarboxylic acid. 1H NMR (400 MHz, DMSO-d6) δ 6.48 (s, 1H), 5.38 (d, J=13.6 Hz, 1H), 5.30 (d, J=13.7 Hz, 1H), 3.87 (d, J=4.7 Hz, 1H), 3.84 (s, 1H), 2.69 (t, J=9.7 Hz, 1H), 2.62 (d, J=15.3 Hz, 2H), 2.53 (d, J=15.3 Hz, 2H), 2.12-1.97

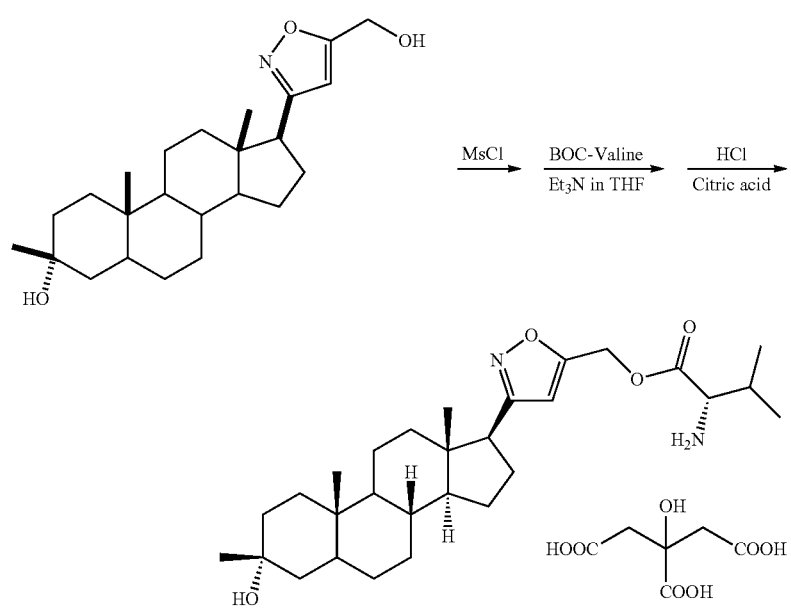

(m, 2H), 1.97-1.80 (m, 1H), 1.76-1.58 (m, 4H), 1.58-1.41 (m, 3H), 1.40-1.07 (m, 8H), 1.04 (s, 3H), 0.99-0.76 (m, 5H), 0.89 (dd, J=8.9, 6.9 Hz, 6H), 0.85-0.78 (m, 1H), 0.68 (s, 3H), 0.45 (s, 3H). UV: Absorbances at 213 nm. MS: 487.44 (M+1), 973.29 (2M+1). HPLC: X-Bridge C18 5µ 250×4.6 mm; flow 1.0 mL/min; Waters 996 PDA detection at 222 nm; solvent 50% Acetonitrile in $H_2O$ (0.1% formic acid) over 16 min; retention time 8.10 min in; 99.9% purity. Solubility: 58 µg/mL. Stability: 100% parent remaining after 24 h in PBS (pH=7.4).

In one embodiment, the disclosure provides a method for using UCI-50027 to make UCI-50027 Lysine bis-citric acid salt. The method of making UCI-50027 Lysine bis-citric acid salt is shown below in Route 12.

Route 12:

brine and dried over $Na_2SO_4$. Biotage purification with 0-60% EtOAc in hexane gave 639 mg of (3-((3R,8R,10S,13S,14S,17S)-3-hydroxy-3,10,13-trimethylhexadecahydro-1H-cyclopenta[a]phenanthren-17-yl)isoxazole-5-yl)methyl N2,N6-bis(tert-butoxycarbonyl)-L-lysinate (88%).

The above product (639 mg) was stirred with 3M of HCl in 15 mL of MeOH (50 eq.) at RT for 24 h. The mixture was purified on a C18 reverse phase Biotage column with 0-50% and 50-100% MeOH in 0.1% HCOOH in $H_2O$ to give 110 mg of (3-((3R,8R,10S,13S,14S,17S)-3-hydroxy-3,10,13-trimethylhexadecahydro-1H-cyclopenta[a]phenanthren-17-yl)isoxazol-5-yl)methyl L-lysinate, which was dissolved in 2 mL of MeOH and mixed with 2 eq. of 2M citric acid solution (0.181 ml). Lyophilization provided 144 mg of (3-((3R,8R,10S,13S,14S,17S)-3-hydroxy-3,10,13-trimethyl

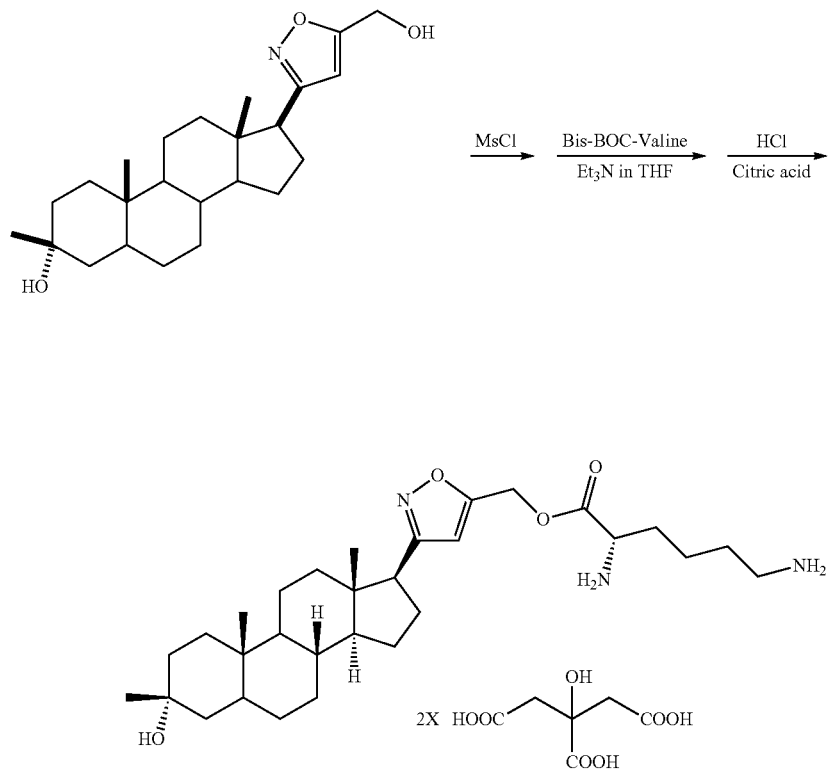

Referring to Route 12, synthesis of (3-((3R,8R,10S,13S,14S,17S)-3-hydroxy-3,10,13-trimethylhexadecahydro-1H-cyclopenta[a]phenanthren-17-yl)isoxazol-5-yl)methyl L-lysinate bis-2-hydroxypropane-1,2,3-tricarboxylic acid To a solution of (3R,8R,10S,13S,14S,17S)-17-(5-(hydroxymethyl)isoxazol-3-yl)-3,10,13-trimethylhexadecahydro-1H-cyclopenta[a]phenanthren-3-ol (UCI-50027) (392 mg, 1.01 mmol) in 10 mL of THF and triethyl amine (0.21 mL, 1.5 eq.) at 0° C. was added methanesulfonyl chloride (0.086 mL, 1.1 eq.). After the resulting mixture was stirred at 0° C. for 1 h, it was diluted with EtOAc. The organic layer was washed with brine and dried over $Na_2SO_4$. The residue after concentration was dissolved in 10 mL of acetone. To it were added bis-BOC-L-lysine (3.50 g, 10 eq.) and triethyl amine (1.8 mL, 13 eq.). The resulting mixture was heated at 65° C. for 3 h. It was cooled and the volatiles were removed. The residue was diluted with DCM and was washed with hexadecahydro-1H-cyclopenta[a]phenanthren-17-yl)isoxazol-5-yl)methyl L-lysinate bis-2-hydroxypropane-1,2,3-tricarboxylic acid. NMR: 1H NMR (400 MHz, DMSO-d6) δ 6.50 (s, 1H), 5.32 (d, J=1.7 Hz, 2H), 3.95 (d, J=6.6 Hz, 1H), 3.85 (s, 1H), 2.75-2.67 (m, 3H), 2.62 (d, J=15.2 Hz, 4H), 2.53 (d, J=15.2 Hz, 4H), 2.10-1.82 (m, 3H), 1.80-1.59 (m, 6H), 1.57-1.43 (m, 4H), 1.43-1.07 (m, 13H), 1.04 (s, 3H), 1.00-0.69 (m, 2H), 0.68 (s, 3H), 0.46 (s, 3H). UV: Absorbances at 214 nm. MS: 516.47 (M+1). HPLC: X-Bridge C18 5µ 250×4.6 mm; flow 1.0 mL/min; Waters 996 PDA detection at 222 nm; solvent 38% Acetonitrile in $H_2O$ (0.1% formic acid) over 15 min; retention time 6.14 min in; 100% purity. Solubility: 5.2 mg/mL. Stability: 94.5% prodrug remaining after 24 h in PBS (pH=7) at RT.

In one embodiment, the disclosure provides a method for using ganaxolone to make UCI-50027 MethylPhosphite Disodium. The method of making UCI-50027 MethylPhosphite Disodium is shown below in Route 13.

Route 13:
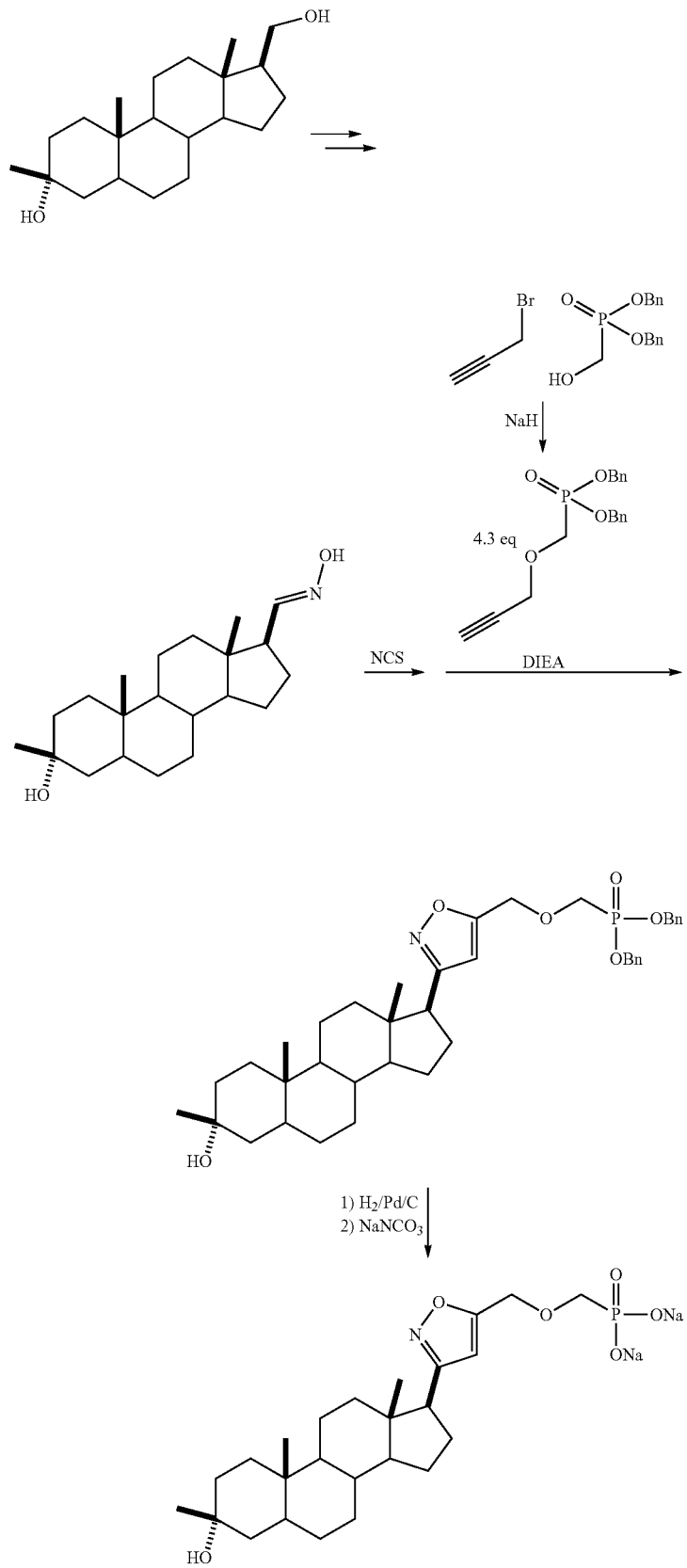

Referring to Route 13, synthesis of dibenzyl (((3-((3R,10S,13S,17S)-3-hydroxy-3,10,13-trimethyl-hexadecahydro-1H-cyclopenta[a]phenanthren-17-yl)isoxazol-5-yl)methoxy)methyl)phosphonate

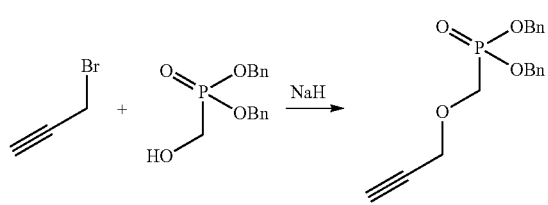

To a suspension of NaH (567 mg, 14.2 mmol) in 8 mL of THF at −78° C. was added dibenzyl (hydroxymethyl)phosphonate (2.76 g, 9.44 mmol) in 3 mL of THF dropwise. The resulting mixture was stirred at −78° C. for 5 h. Propargyl bromide (80% in toluene, 2.4 mL, 3 eq.) was then added and the mixture was stirred and was allowed to warm to RT overnight. It was quenched with NH4Cl (sat.) and diluted with EtOAc and water. The organic layer was washed with brine, dried over Na$_2$SO$_4$ and concentrated. Biotage purification with 0-80% EtOAc in hexane gave 1.49 g of dibenzyl ((prop-2-yn-1-yloxy)methyl)phosphonate in 48% yield.

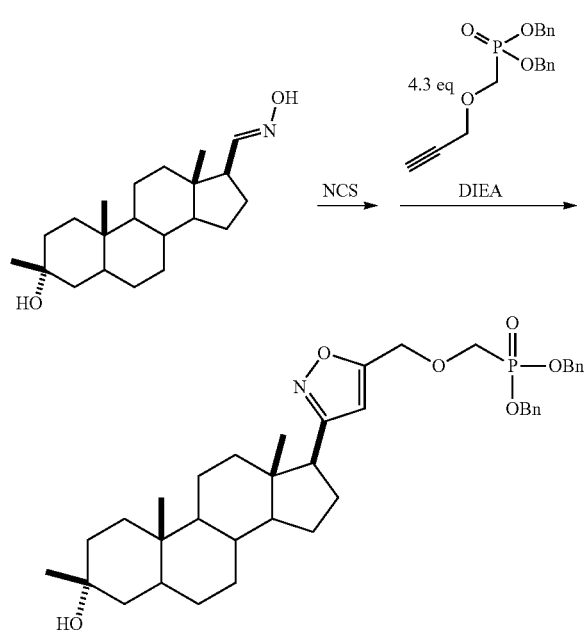

The mixture of (E)-3-hydroxy-3,10,13-trimethylhexadecahydro-1H-cyclopenta[a]phenanthrene-17-carbaldehyde oxime (346 mg, 1.04 mmol), NCS (N-Chlorosuccimide, 146 mg, 1.05 eq.) and pyridine (5 drops) in 21 mL of DCM was stirred at RT for 1 h. Dibenzyl ((prop-2-yn-1-yloxy)methyl)phosphonate (1.49 g, 4.3 eq. in 2 mL of DCM) and diisopropylethylamine (0.2 mL 1.1 eq.) were then added. The resulting mixture was stirred at RT overnight. The reaction mixture was diluted with DCM, washed with NaHCO$_3$ (sat.), brine and dried over Na$_2$SO$_4$. Biotage purification with 0-80% EtOAc in hexane gave 318 mg of dibenzyl (((3-((3R,10S,13S,17S)-3-hydroxy-3,10,13-trimethylhexadecahydro-1H-cyclopenta[a]phenanthr en-17-yl)isoxazol-5-yl)methoxy)methyl)phosphonate in 46% yield. 1H NMR (400 MHz, DMSO-d6) δ 7.44-7.17 (m, 10H), 6.33 (s, 1H), 5.09-4.97 (m, 4H), 4.64 (s, 2H), 3.96 (d, J=8.5 Hz, 2H), 3.84 (s, 1H), 2.66 (t, J=9.6 Hz, 1H), 2.06-1.98 (m, 1H), 1.90 (dd, J=9.7, 5.5 Hz, 1H), 1.64 (dd, J=18.8, 8.4 Hz, 4H), 1.50 (d, J=12.1 Hz, 3H), 1.39-1.06 (m, 11H), 1.04 (s, 3H), 1.00-0.70 (m, 2H), 0.68 (s, 3H), 0.43 (s, 3H).

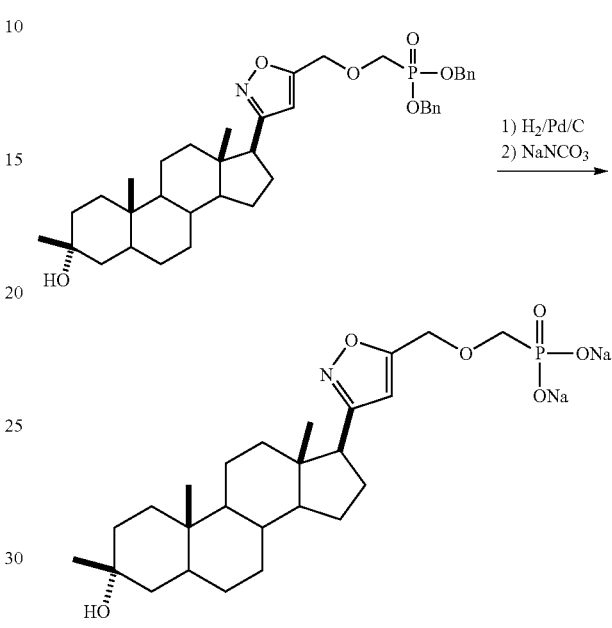

Dibenzyl (((3-((3R,10S,13S,17S)-3-hydroxy-3,10,13-trimethylhexadecahydro-1H-cyclopenta[a]phenanthren-17-yl)isoxazol-5-yl)methoxy)methyl)phosphonate (318 mg, 0.481 mmol) was dissolved in 7 mL of THF. To it was added 10% Pd/C (51 mg, 0.1 eq.). The mixture was degassed under vacuum and flushed with H2. After it was stirred under H2 balloon for 2 h at RT, it was filtered through a CELITE® pad and washed with MeOH. The filtrate was concentrated and the residue was purified on a C18 reverse phase Biotage column using 0-100% MeOH in 0.1% formic acid water to give 216 mg (0.449 mL) of methylphosphonic acid, which was dissolved 2.5 mL of MeOH and cooled to 0° C. To it was added 2 eq. of NaHCO$_3$ (0.1 M, 9 mL) and stirred (pH=7). The final sodium salt was obtained by lyophilization (250 mg). NMR: 1H NMR (400 MHz, Methanol-d4) δ 6.41 (s, 1H), 4.68 (s, 2H), 3.60 (d, J=9.0 Hz, 2H), 2.71 (t, J=9.7 Hz, 1H), 2.20-1.91 (m, 2H), 1.66-1.18 (m, 18H), 1.15 (s, 3H), 1.09-0.80 (m, 2H), 0.78 (s, 3H), 0.57 (s, 3H). UV: Absorbances at 214 nm. MS: 468.23 (M+1); 935.29 (2M+1). HPLC: X-Bridge C18 5μ 250×4.6 mm; flow 1.0 mL/min; Waters 996 PDA detection at 222 nm; solvent 50% Acetonitrile in H$_2$O (0.1% formic acid) over 15 min; retention time 6.38 min in; 99.3% purity. Solubility: 4.3 mg/mL. Stability: 98.3% prodrug remaining after 23 h in PBS (pH=7) at room temperature.

In one embodiment, the disclosure provides a method for using ganaxolone to make UCI-50027 Diisopropyl Carbonate. The method of making UCI-50027 Diisopropyl Carbonate is shown below in Route 14.

Route 14:

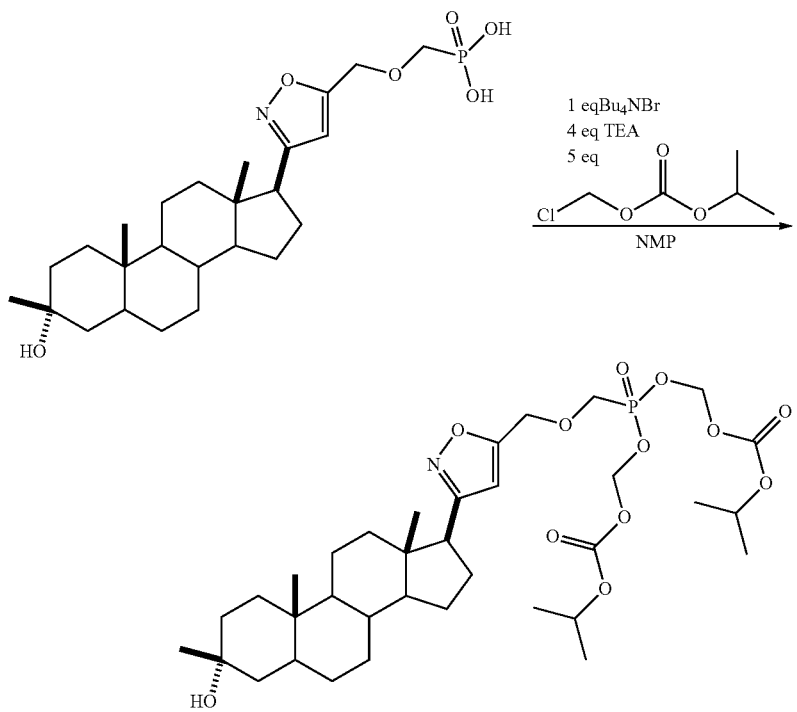

Referring to Route 14, Synthesis of (((((3-((3R,10S, 13S,17S)-3-hydroxy-3,10,13-trimethylhexadeca-hydro-1H-cyclopenta[a]phenanthren-17-yl)isoxazol-5-yl)methoxy)methyl)phosphoryl)bis(oxy))bis(methylene) diisopropyl bis(carbonate)

The mixture of (((3-((3R,10S,13S,17S)-3-hydroxy-3,10, 13-trimethylhexadecahydro-1H-cyclopenta[a]phenanthren-17-yl)isoxazol-5-yl)methoxy)methyl)phosphonic acid (260 mg, 0.54 mmol), tetrn-butylammonium bromide (174 mg, 1 eq.), triethyl amine (0.3 mL, 4 eq.) and chloromethyl isopropyl carbonate (0.34 mL, 5 eq.) in 0.64 mL of NMP was heated at 60° C. for 3 h. After it was cooled to RT, it was diluted with EtOAc and was washed with brine and dried over $Na_2SO_4$. Biotage purification with 0-70% EtOAc in hexane gave the desired product, (((((3-((3R,10S,13S,17S)-3-hydroxy-3,10,13-trimethylhexadecahydro-1H-cyclopenta[a]phenanthren-17-yl)isoxazol-5-yl)methoxy)methyl)phosphoryl)bis(oxy))bis(m ethylene) diisopropyl bis(carbonate), 342 mg, 63%. NMR: 1H NMR (400 MHz, DMSO-d6) δ 6.38 (s, 1H), 5.58 (dd, J=12.6, 2.4 Hz, 4H), 4.79 (q, J=6.2 Hz, 2H), 4.64 (s, 2H), 3.99 (dd, J=16.6, 8.1 Hz, 2H), 3.83 (s, 1H), 2.65 (t, J=9.4 Hz, 1H), 2.07-1.77 (m, 2H), 1.74-1.26 (m, 8H), 1.26-1.20 (m, 10H), 1.21 (d, J=6.4 Hz, 12H), 1.02 (s, 2H), 0.98-0.62 (m, 2H), 0.66 (s, 3H), 0.44 (s, 3H). UV: Absorbances at 210 nm. MS: 714.31 (M+1). HPLC: X-Bridge C18 5μ 250×4.6 mm; flow 1.0 mL/min; Waters 996 PDA detection at 212 nm; solvent 10%-100% Acetonitrile in $H_2O$ (0.1% formic acid) over 20 min; retention time 13.4 min in; 97.1% purity. Solubility: 6.6 μg/mL in pH=7.4 buffer. Stability: cannot be accurately measured due to the extremely low intensity of the peak, which is the result of extremely low solubility in PBS.

In one embodiment, the disclosure provides a method for using ganaxolone to make UCI-50027 MethylPhosphite Disodium. The method of making UCI-50027 MethylPhosphite Disodium is shown below in Route 15.

Route 15

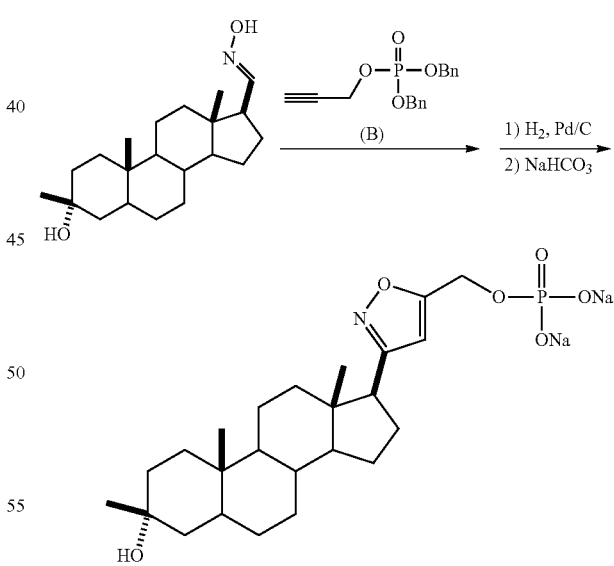

Referring to Route 15, Synthesis of bis-sodium (3-((3R,10S,13S,17S)-3-hydroxy-3,10,13-trimethyl-hexadecahydro-1H-cyclopenta[a]phenanthren-17-yl) isoxazol-5-yl)methyl phosphate Dibenzyl phosphonate (1.72 g, 6.56 mmol) and NCS (N-chlorosuccinimide, 0.963 g, 1.1 eq.) were stirred together in 35 mL of toluene at RT for 2.5 h. It was filtered and the filtrate was concentrated to give 2.15 g of dibenzyl phosphorochloridate in quantitative yield. It was used in the next step without any further purification.

At 0° C., dibenzyl phosphorochloridate (1.94 g, 6.56 mmol, 1.3 eq.) was added to a solution of propargyl alcohol (0.29 mL, 5.05 mmol) and DMAP (81 mg, 0.1 eq.) in 65 mL of DCM. It was followed by the addition of triethyl amine (1.1 mL, 1.2 eq.). The mixture was stirred and was allowed to warm to RT overnight. It was then quenched with NH4Cl (sat.) and was diluted with DCM. The organic layer was washed with brine and dried ($Na_2SO_4$). Biotage purification with 0-60% EtOAc in hexane gave 0.553 g of dibenzyl prop-2-yn-1-yl phosphate (B) in 19% yield.

The mixture of (E)-3-hydroxy-3,10,13-trimethylhexadecahydro-1H-cyclopenta[a]phenanthrene-17-carbaldehyde oxime (181 mg, 0.543 mmol), NCS (N-Chlorosuccimide, 76 mg, 1.05 eq.) and pyridine (3 drops) in 11 mL of DCM was stirred at RT for 1 h. Dibenzyl prop-2-yn-1-yl phosphate (B) (553 mg, 2.2 eq. in 3 mL of DCM) and diisopropylethyl-amine (0.1 mL 1.1 eq.) were then added. The resulting mixture was stirred at RT overnight. The reaction mixture was diluted with DCM, washed with $NaHCO_3$ (sat.), brine and dried over $Na_2SO_4$. Biotage purification with 0-70% EtOAc in hexane gave 240 mg of dibenzyl ((3-((3R,10S, 13S,17S)-3-hydroxy-3,10,13-trimethylhexadecahydro-1H-cyclopenta[a]phenanthren-17-yl)isoxazol-5-yl)methyl) phosphate in 68% yield.

The mixture of 240 mg of dibenzyl ((3-((3R,10S,13S, 17S)-3-hydroxy-3,10,13-trimethylhexadecahydro-1H-cyclopenta[a]phenanthren-17-yl)isoxazol-5-yl)methyl) phosphate (0.37 mmol) and 10% Pd/C (39 mg, 0.1 eq.) in 5 mL of MeOH was degassed under house vacuum and was flushed with hydrogen. After the mixture was stirred at RT under H2 balloon for 2 h, it was filtered through a CELITE® pad. The filtrate was concentrated to give 173 mg of dihydro-phosphate, which was converted to sodium salt by dissolving in 5 mL of MeOH and reacted with 2 eq. of $NaHCO_3$ (0.1M, 7.4 mL) at 0° C. Lyophilization afforded 188 mg of bis-sodium (3-((3R,10S,13S,17S)-3-hydroxy-3, 10,13-trimethylhexadecahydro-1H-cyclopenta[a] phenanthren-17-yl)isoxazol-5-yl)methyl phosphate. NMR: 1H NMR (400 MHz, DMSO-d6) δ 6.21 (s, 1H), 4.63 (d, J=6.6 Hz, 2H), 2.68-2.60 (m, 1H), 2.19-1.77 (m, 2H), 1.77-1.60 (m, 2H), 1.61-1.41 (m, 2H), 1.41-1.07 (m, 13H), 1.04 (s, 3H), 1.00-0.70 (m, 2H), 0.69 (s, 3H), 0.48 (s, 3H). UV: Absorbances at 214 nm. MS: 468.23 (M+1); 935.29 (2M+1). HPLC: X-Bridge C18 5µ 250×4.6 mm; flow 1.0 mL/min; Waters 996 PDA detection at 222 nm; solvent 50% Acetonitrile in $H_2O$ (0.1% formic acid) over 15 min; retention time 6.38 min in; 99.3% purity. Solubility: 4.3 mg/mL. Stability: 98.3% prodrug remaining after 23 h in PBS (pH=7) at room temperature.

The following tables summarizes the amount, the purity, solubility and stability of the compounds described in these routes of synthesis.

TABLE 2

| # | Name | Amount | Purity | Solubility |
|---|------|--------|--------|------------|
| 1 | Ganaxolone (GX) | 522 mg | 96.6% | <BQL* |
| 2 | 21-OH GX | 290 mg | 98.8% | <BQL* |
| 3 | UCI-50027 | 356 mg | 99.6% | <1 µg/mL |

*BQL = below the quantification level

TABLE 3

| # | Name | Amount | Purity | Solubility[1] | Stability[2] (24 h) |
|---|------|--------|--------|------------|---------------------|
| 1 | 21-OH Gx Phosphate Disodium | 545 mg | 95% | >10 mg/mL | 100% |
| 2 | 21-OH Gx Valine | 335 mg | 94.4% | 2 mg/mL | 75% (6 h) |
| 3 | 21-OH Gx Lysine | 305 mg | 96.1% | 9.7 mg/mL | 75% |
| 4 | 21-OH Gx Succinate Sodium | 268 mg | 94% | 0.96 mg/mL | 98% |
| 5 | 21-OH Gx Malic Acid | 300 mg | 96.0% | 0.41 mg/mL | 100% |
| 6 | 21-OH Gx Piperidine diol | 393 mg | 97.4% | 0.48 mg/mL | 100% |
| 7 | UCI-50027 Phosphate Disodium | 120 mg / 110 mg | 100% / 100% | 5 mg/mL | 100% |
| 8 | UCI-50027 Valine | 170 mg / 190 mg | 99.1% / 99.9% | 58 µg/mL | 100% |
| 9 | UCI-50027 Lysine | 211 mg | 100% | 5.2 mg/mL | 94.5% |
| 10 | UCI-50027 methylphosphite sodium | 210 mg | 99.3% | 4.3 mg/mL | 98.3% |
| 11 | UCI-50027 methylphosphite diisopropyl carbonate | 243 mg | 97.1% | 6.6 µg/mL | N.A.[3] |
| 12 | 21-OH GX methylphosphite sodium | 368 mg | 100% | 7.3 mg/mL | 100% |
| 13 | 21-OH GX carbamate | 201 mg | 100% | 118 µg/mL (pH = 7.4) | N.D.[4] |

[1] Solubility was measured in pH = 7 phosphate buffer.
[2] Stability was measured in pH = 7 phosphate buffer at room temperature over 24 h time period and percentage was reported as how much a drug was remaining in the buffer solution at 24 h time point or otherwise specified time point.
[3] Not available due to weak signal.
[4] Not determined.

It is apparent that comparison of Table 2 and Table 3 indicate that there is a significant improvement in solubility for the neurosteroid derivatives compared to GX, 21-OH GX and UCI-50027. Among all the compounds, bis-sodium phosphate or phosphite salts show the best solubility 4 to >10 mg/mL (entry 1, 7, 10). Lysine esters have good solubility as well, being associated with 2HCl in entry 3 or with 2 citric acid in entry 9, provided 9.7 mg/mL and 5.2 mg/mL solubility, respectively. Another case in point is entry #13 in Table 3. When the basic nitrogen was free base, the 21-OH GX carbamate has low solubility and the solubility increases by 10-fold when the nitrogen was protonated at pH=6.

In summary, novel compounds from the pharmacophore template described in Formula (A) were prepared in various multi-step reactions from easily accessible pregnenolone, 21-Bromo GX, and 21-OH GX. The 21-hydroxyl group allows for simple substituents, such as amino analogs, alkyl ether derivatives, and other functional groups. Additionally, the 21-bromo-GX derivative provides a variety of options for modifying GX.

It will be appreciated that the neurosteroid derivatives of the disclosure can be provided in the form of a base or an acid addition salt prepare from a pharmaceutically acceptable salt including those known in the art, or in the form of a hydrate or solvate.

All of the compositions and methods disclosed and claimed herein can be made and executed without undue experimentation in light of the present disclosure. While the compositions and methods of this disclosure have been described in terms of preferred embodiments, it will be apparent to those of skill in the art that variations may be applied to the compositions and methods and in the steps or in the sequence of steps of the methods described herein without departing from the concept, spirit and scope of the disclosure. More specifically, it will be apparent that certain agents which are both chemically related may be substituted for the agents described herein while the same or similar results would be achieved. All such similar substitutes and modifications apparent to those skilled in the art are deemed to be within the spirit, scope and concept of the disclosure as defined by the appended claims.

What is claimed is:

1. A method for treating epilepsy comprising administering to a subject in need thereof a therapeutically effective amount of a compound, a pharmaceutically acceptable salt of said compound, or a pharmaceutical composition comprising a pharmaceutically acceptable excipient and said compound, said compound or said pharmaceutically acceptable salt being selected from:

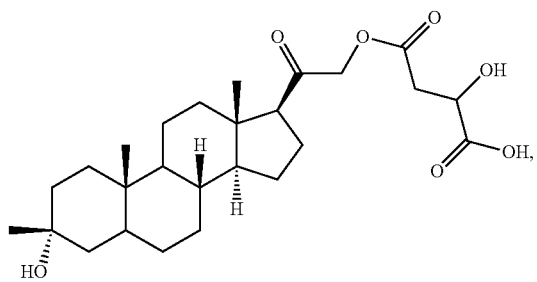

21-OH GX Malic Acid

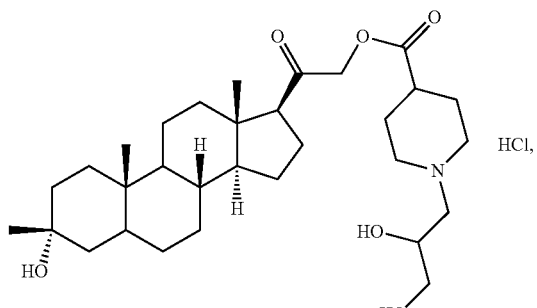

21-OH GX Piperidine Diol

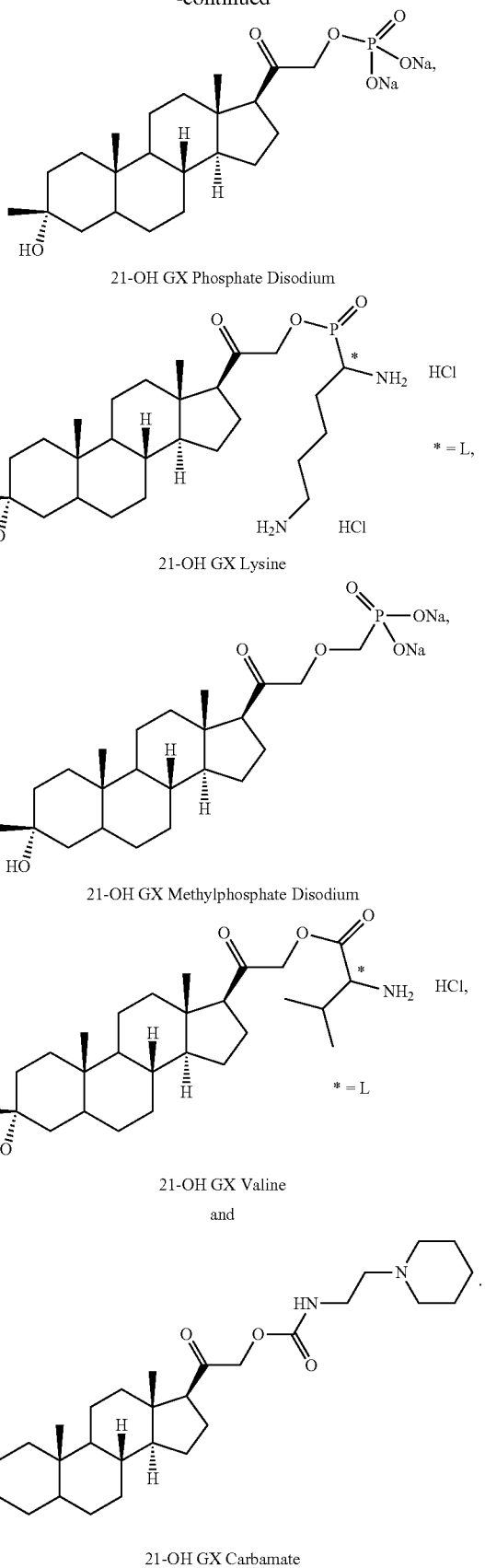

21-OH GX Phosphate Disodium

21-OH GX Lysine

21-OH GX Methylphosphate Disodium

21-OH GX Valine and

21-OH GX Carbamate

2. The method of claim 1, wherein the compound is administered to a patient by oral, parenteral, intravenous, transdermal, inhalation, intracerebral or topical administration in a suitable formulation.

3. A method for treating epilepsy comprising administering to a subject in need thereof a therapeutically effective amount of a compound, a pharmaceutically acceptable salt of said compound, or a pharmaceutical composition comprising a pharmaceutically acceptable excipient and said compound, said compound or pharmaceutically acceptable salt being selected from:

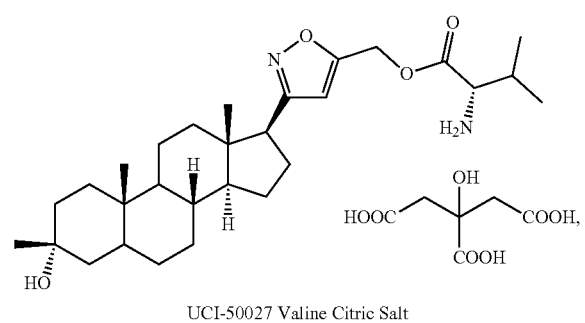

UCI-50027 Valine Citric Salt

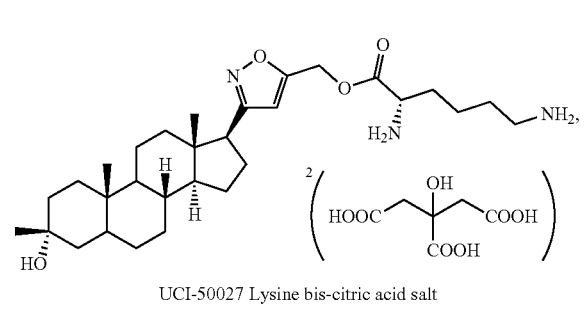

UCI-50027 Lysine bis-citric acid salt

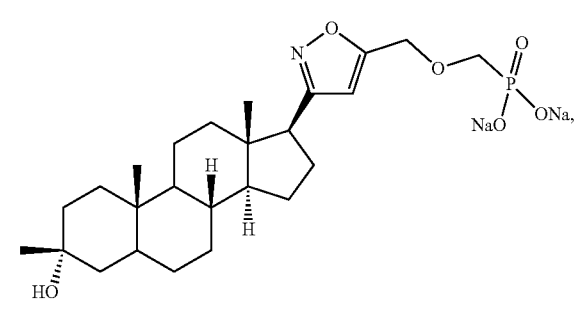

UCI-50027 MethylPhosphite Disodium

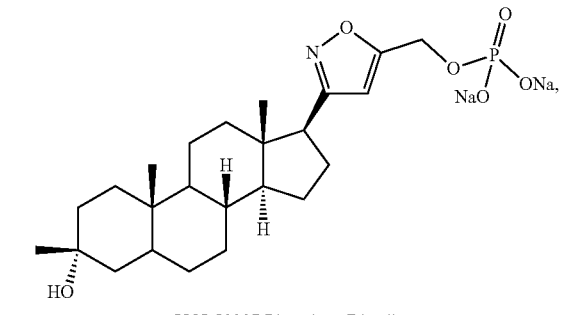

UCI-50027 Phosphate Disodium

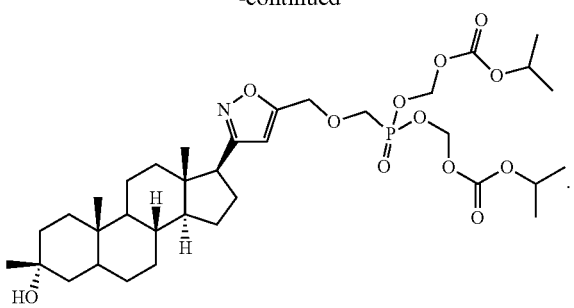

UCI-50027 Diisopropyl Carbonate

4. The method of claim 3, wherein the compound is given to a patient by oral, parenteral, intravenous, transdermal, inhalation, intracerebral or topical administration in a suitable formulation.

5. The method of claim 1, wherein said compound or said pharmaceutically acceptable salt is

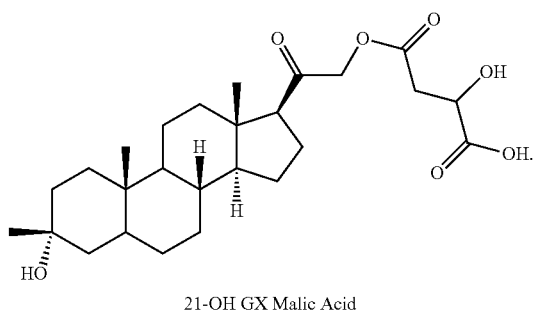

21-OH GX Malic Acid

6. The method of claim 1, wherein said compound or said pharmaceutically acceptable salt is

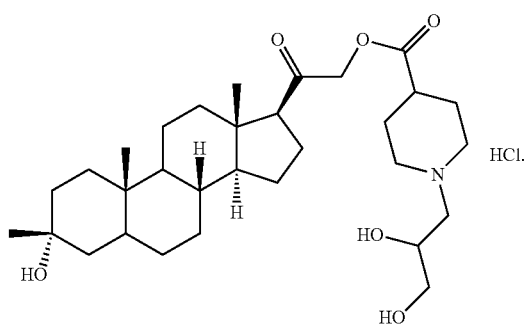

21-OH GX Piperidine Diol

7. The method of claim 1, wherein said compound or said pharmaceutically acceptable salt is

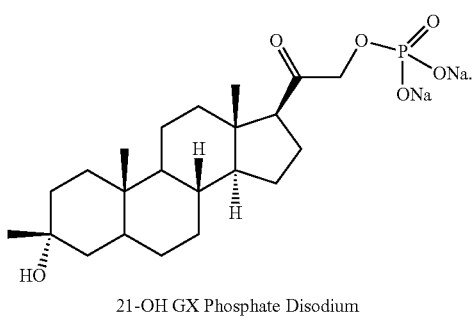

21-OH GX Phosphate Disodium

8. The method of claim 1, wherein said compound or said pharmaceutically acceptable salt is

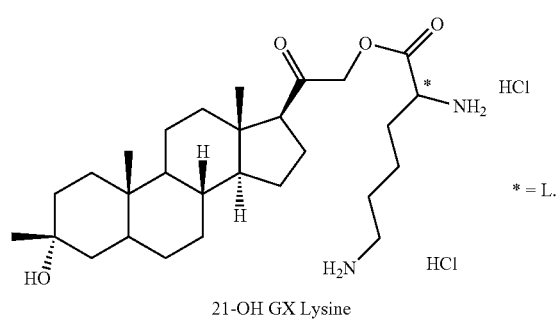

21-OH GX Lysine

9. The method of claim 1, wherein said compound or said pharmaceutically acceptable salt is

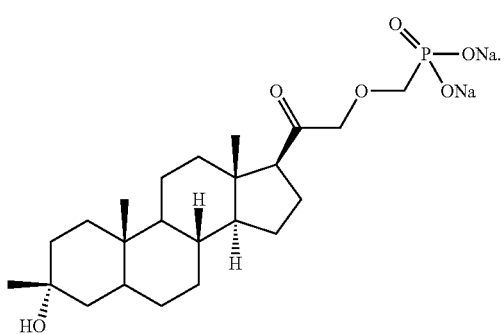

21-OH GX Methylphosphite Disodium

10. The method of claim 1, wherein said compound or said pharmaceutically acceptable salt is

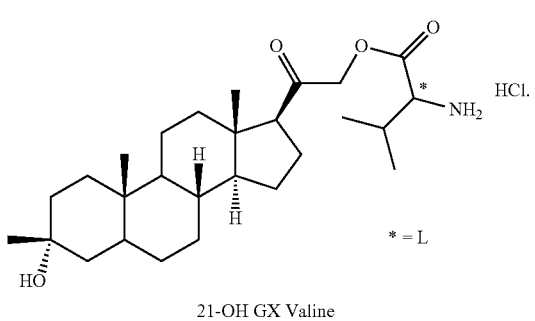

21-OH GX Valine

11. The method of claim 1, wherein said compound or said pharmaceutically acceptable salt is

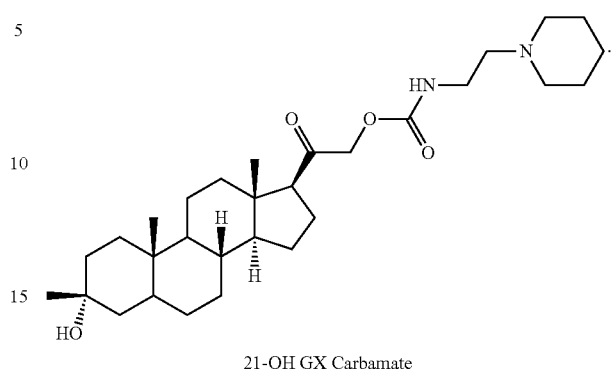

21-OH GX Carbamate

12. The method of claim 3, wherein said compound or said pharmaceutically acceptable salt is

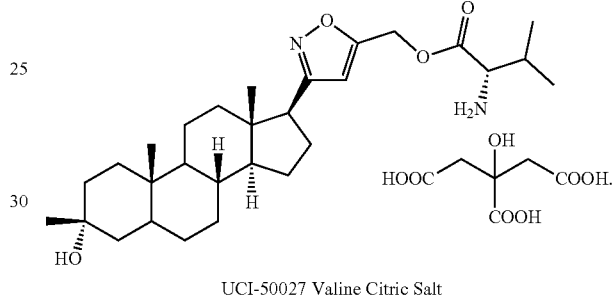

UCI-50027 Valine Citric Salt

13. The method of claim 3, wherein said compound or said pharmaceutically acceptable salt is

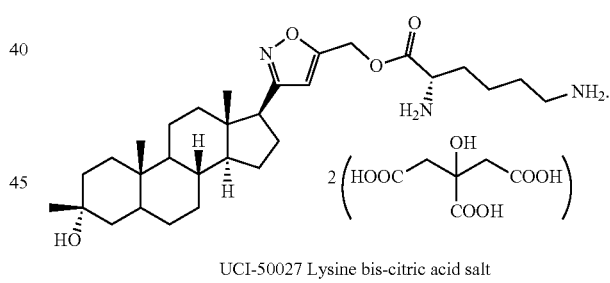

UCI-50027 Lysine bis-citric acid salt

14. The method of claim 3, wherein said compound or said pharmaceutically acceptable salt is

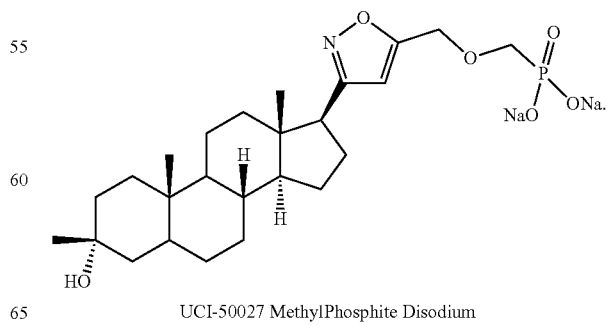

UCI-50027 MethylPhosphite Disodium

15. The method of claim 3, wherein said compound or said pharmaceutically acceptable salt is
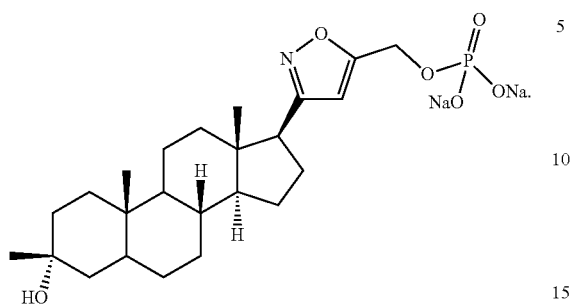
UCI-50027 Phosphate Disodium
16. The method of claim 3, wherein said compound or said pharmaceutically acceptable salt is
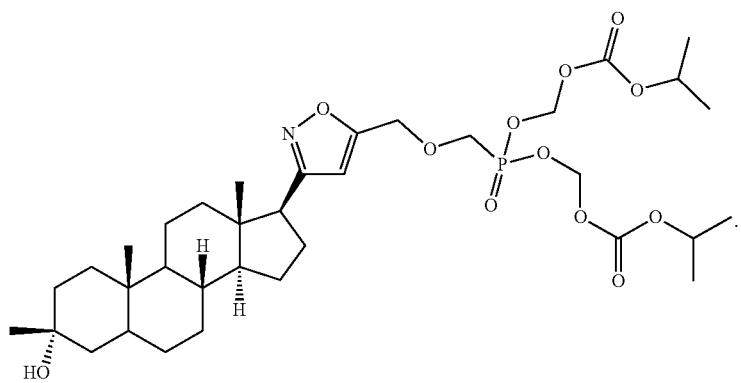
UCI-50027 Diisopropyl Carbonate
* * * * *